(12) United States Patent
Hanser et al.

(10) Patent No.: US 12,343,024 B2
(45) Date of Patent: Jul. 1, 2025

(54) SYSTEM, DEVICES AND METHODS FOR REMOVING OBSTRUCTIONS IN BODY LUMENS

(71) Applicant: Von Vascular, Inc., Weston, FL (US)

(72) Inventors: Manning J. Hanser, Weston, FL (US); David Castano Galindo, Fort Lauderdale, FL (US); Victor M. Gamez, Fort Lauderdale, FL (US); Alfonso Hermida, Miramar, FL (US); Ryan David Ortiz, Miramar, FL (US)

(73) Assignee: Von Vascular, Inc., Weston, FL (US)

( * ) Notice: Subject to any disclaimer, the term of this patent is extended or adjusted under 35 U.S.C. 154(b) by 0 days.

(21) Appl. No.: 18/949,280

(22) Filed: Nov. 15, 2024

(65) Prior Publication Data

US 2025/0064467 A1 Feb. 27, 2025

Related U.S. Application Data

(63) Continuation of application No. 18/596,868, filed on Mar. 6, 2024, now Pat. No. 12,220,139, which is a
(Continued)

(51) Int. Cl.
*A61B 17/22* (2006.01)
*A61B 17/00* (2006.01)
*A61B 90/00* (2016.01)

(52) U.S. Cl.
CPC ........ *A61B 17/22* (2013.01); *A61B 17/00234* (2013.01); *A61B 90/06* (2016.02);
(Continued)

(58) Field of Classification Search
CPC .............. A61B 17/22; A61B 17/00234; A61B 2017/00561; A61B 2017/22079;
(Continued)

(56) References Cited

U.S. PATENT DOCUMENTS 3,589,363 A 6/1971 Banko et al.
4,798,580 A 1/1989 DeMeo et al.
(Continued)

FOREIGN PATENT DOCUMENTS

EP 0777504 B1 10/1998
WO WO 2006/117207 A1 11/2006
(Continued)

OTHER PUBLICATIONS

Invitation to Pay Additional Fees for International Application No. PCT/US2024/015950, mailed May 28, 2024.
(Continued)

*Primary Examiner* — Katherine M Rodjom
(74) *Attorney, Agent, or Firm* — Mills IP Law, PLLC

(57) ABSTRACT

A method includes receiving at an aspiration module of a pump assembly an input associated with a catheter parameter of a catheter coupled to the pump assembly. An aspiration profile associated with the catheter parameter is selected via the aspiration module from a list of preset aspiration profiles associated with different catheters and include upper and lower pressure limits, an aspiration speed, and an infusion speed. A first signal is sent to actuate the pump based on the aspiration profile to operate the pump in a first mode. A pressure signal is received at the aspiration module and a second signal is sent to actuate the pump based on the aspiration profile to operate the pump in a second mode, in which the pump is cycled between the aspiration speed and the infusion speed such that the catheter pressure cycles between the upper pressure limit and the lower pressure limit.

27 Claims, 65 Drawing Sheets

Related U.S. Application Data continuation of application No. PCT/US2024/015950, filed on Feb. 15, 2024, and a continuation-in-part of application No. 18/373,955, filed on Sep. 27, 2023, which is a continuation-in-part of application No. 18/123,973, filed on Mar. 20, 2023.

(60) Provisional application No. 63/474,167, filed on Jul. 26, 2022, provisional application No. 63/335,168, filed on Apr. 26, 2022, provisional application No. 63/325,778, filed on Mar. 31, 2022, provisional application No. 63/321,706, filed on Mar. 20, 2022.

(52) U.S. Cl.
CPC ............... *A61B 2017/00022* (2013.01); *A61B 2017/00123* (2013.01); *A61B 2017/00137* (2013.01); *A61B 2017/00199* (2013.01); *A61B 2017/00292* (2013.01); *A61B 2017/00561* (2013.01); *A61B 2017/00778* (2013.01); *A61B 2017/22079* (2013.01); *A61B 2090/064* (2016.02); *A61B 2217/005* (2013.01); *A61B 2217/007* (2013.01)

(58) Field of Classification Search
CPC ........... A61B 2017/00123; A61B 2017/00137; A61B 2017/00199; A61B 2017/00292; A61B 2017/00778; A61B 2217/005; A61M 1/64; A61M 1/65; A61M 1/68
See application file for complete search history.

(56) References Cited

U.S. PATENT DOCUMENTS

| | | | |
|---|---|---|---|
| 4,832,685 A | 5/1989 | Haines |
| 4,921,477 A | 5/1990 | Davis |
| 4,930,997 A | 6/1990 | Bennett |
| 4,935,005 A | 6/1990 | Haines |
| 5,125,891 A | 6/1992 | Hossain et al. |
| 5,267,956 A | 12/1993 | Beuchat |
| 5,364,342 A | 11/1994 | Beuchat |
| 5,419,774 A | 5/1995 | Willard et al. |
| 5,460,490 A | 10/1995 | Carr et al. |
| 5,496,270 A | 3/1996 | Nettekoven |
| 5,827,229 A | 10/1998 | Auth et al. |
| 6,022,747 A | 2/2000 | Gherson et al. |
| 6,071,267 A | 6/2000 | Zamierowski |
| 6,115,860 A | 9/2000 | Vrzalik |
| D445,804 S | 7/2001 | Tsai |
| 6,306,163 B1 | 10/2001 | Fitz |
| 6,387,065 B1 | 5/2002 | Tumey |
| 6,468,237 B1 | 10/2002 | Lina |
| 6,517,513 B1 | 2/2003 | Covington |
| 6,547,756 B1 | 4/2003 | Greter et al. |
| 6,673,028 B1 | 1/2004 | Argenta et al. |
| 6,904,631 B2 | 6/2005 | Vrzalik et al. |
| 7,004,915 B2 | 2/2006 | Boynton et al. |
| D520,023 S | 5/2006 | Goto et al. |
| 7,108,683 B2 | 9/2006 | Zamierowski |
| 7,198,046 B1 | 4/2007 | Argenta et al. |
| 7,276,052 B2 | 10/2007 | Kobayashi et al. |
| 7,284,965 B2 | 10/2007 | Adahan |
| D573,609 S | 7/2008 | Bilger |
| 7,410,491 B2 | 8/2008 | Hopkins et al. |
| 7,662,109 B2 | 2/2010 | Hibner |
| 7,666,161 B2 | 2/2010 | Nash et al. |
| 7,713,235 B2 | 5/2010 | Torrance et al. |
| 7,717,853 B2 | 5/2010 | Nita |
| 7,828,748 B2 | 11/2010 | Hibner |
| 7,842,009 B2 | 11/2010 | Torrance et al. |
| 7,854,707 B2 | 12/2010 | Hibner et al. |
| 7,867,173 B2 | 1/2011 | Hibner et al. |
| 7,896,817 B2 | 3/2011 | Garrison |
| 7,918,804 B2 | 4/2011 | Monson et al. |
| 7,931,659 B2 | 4/2011 | Bose et al. |
| 7,938,786 B2 | 5/2011 | Ritchie et al. |
| 7,959,608 B2 | 6/2011 | Nash et al. |
| 7,981,049 B2 | 7/2011 | Ritchie et al. |
| 8,038,627 B2 | 10/2011 | Hibner |
| 8,070,735 B2 | 12/2011 | Koch et al. |
| 8,075,510 B2 | 12/2011 | Aklog et al. |
| 8,118,755 B2 | 2/2012 | Hibner et al. |
| 8,235,955 B2 | 8/2012 | Blott et al. |
| 8,251,916 B2 | 8/2012 | Speeg et al. |
| 8,333,796 B2 | 12/2012 | Tompkins |
| 8,337,475 B2 | 12/2012 | Christensen et al. |
| 8,366,735 B2 | 2/2013 | Bose et al. |
| 8,394,078 B2 | 3/2013 | Torrance et al. |
| 8,414,534 B2 | 4/2013 | Bandhauer et al. |
| 8,460,312 B2 | 6/2013 | Bose et al. |
| 8,465,467 B2 | 6/2013 | Gao |
| 8,480,595 B2 | 7/2013 | Speeg et al. |
| 8,506,512 B2 | 8/2013 | Aklog et al. |
| 8,591,453 B2 | 11/2013 | Stubkjaer et al. |
| 8,613,717 B2 | 12/2013 | Aklog et al. |
| 8,632,498 B2 | 1/2014 | Rimsa et al. |
| 8,657,785 B2 | 2/2014 | Torrance et al. |
| 8,679,150 B1 | 3/2014 | Janardhan et al. |
| 8,690,907 B1 | 4/2014 | Janardhan et al. |
| 8,702,623 B2 | 4/2014 | Parihar et al. |
| 8,715,314 B1 | 5/2014 | Janardhan et al. |
| 8,715,315 B1 | 5/2014 | Janardhan et al. |
| 8,715,316 B1 | 5/2014 | Janardhan et al. |
| 8,721,676 B1 | 5/2014 | Janardhan et al. |
| 8,721,677 B1 | 5/2014 | Janardhan et al. |
| 8,733,618 B1 | 5/2014 | Janardhan et al. |
| 8,734,374 B2 | 5/2014 | Aklog et al. |
| 8,737,017 B1 | 5/2014 | Abe |
| 8,747,432 B1 | 6/2014 | Janardhan et al. |
| 8,753,371 B1 | 6/2014 | Janardhan et al. |
| 8,758,315 B2 | 6/2014 | Chen et al. |
| 8,783,151 B1 | 7/2014 | Janardhan et al. |
| 8,789,452 B1 | 7/2014 | Janardhan et al. |
| 8,795,244 B2 | 8/2014 | Randolph et al. |
| 8,803,030 B1 | 8/2014 | Janardhan et al. |
| 8,816,247 B1 | 8/2014 | Janardhan et al. |
| D712,933 S | 9/2014 | DeOreo et al. |
| 8,852,219 B2 | 10/2014 | Wulfman et al. |
| 8,852,227 B1 | 10/2014 | Janardhan et al. |
| 8,859,934 B1 | 10/2014 | Janardhan et al. |
| 8,872,068 B1 | 10/2014 | Janardhan et al. |
| 8,882,797 B2 | 11/2014 | Janardhan et al. |
| 8,895,891 B2 | 11/2014 | Janardhan et al. |
| 8,904,914 B2 | 12/2014 | Janardhan et al. |
| 8,910,555 B2 | 12/2014 | Janardhan et al. |
| 8,911,487 B2 | 12/2014 | Bennett |
| 8,920,402 B2 | 12/2014 | Nash et al. |
| 8,932,320 B1 | 1/2015 | Janardhan et al. |
| 9,034,007 B2 | 5/2015 | Janardhan |
| 9,078,964 B2 | 7/2015 | Schuman |
| 9,095,326 B2 | 8/2015 | Ritchie et al. |
| 9,119,656 B2 | 9/2015 | Bose et al. |
| 9,125,731 B2 | 9/2015 | Ross et al. |
| 9,179,931 B2 | 11/2015 | Janardhan et al. |
| 9,179,995 B2 | 11/2015 | Janardhan et al. |
| 9,186,444 B2 | 11/2015 | Lonky et al. |
| 9,241,699 B1 | 1/2016 | Kume et al. |
| 9,265,512 B2 | 2/2016 | Garrison et al. |
| 9,314,324 B2 | 4/2016 | Janardhan et al. |
| 9,332,998 B2 | 5/2016 | Ray et al. |
| 9,332,999 B2 | 5/2016 | Ray et al. |
| 9,345,457 B2 | 5/2016 | Speeg et al. |
| 9,402,938 B2 | 8/2016 | Aklog et al. |
| RE46,135 E | 9/2016 | Hibner |
| 9,445,831 B2 | 9/2016 | Mark |
| 9,526,865 B2 | 12/2016 | Quick |
| 9,532,792 B2 | 1/2017 | Galdonik et al. |
| 9,561,129 B2 | 2/2017 | Ross et al. |
| 9,561,345 B2 | 2/2017 | Garrison et al. |
| 9,592,068 B2 | 3/2017 | Janardhan et al. |
| 9,615,832 B2 | 4/2017 | Bose et al. |
| 9,655,633 B2 | 5/2017 | Leynov et al. |
| 9,693,789 B2 | 7/2017 | Garrison et al. |

(56) References Cited

U.S. PATENT DOCUMENTS

| | | |
|---|---|---|
| 9,750,524 B2 | 9/2017 | Janardhan et al. |
| 9,820,761 B2 | 11/2017 | Garrison et al. |
| 9,833,251 B2 | 12/2017 | Janardhan et al. |
| 9,855,374 B2 | 1/2018 | Sherman et al. |
| 9,883,854 B2 | 2/2018 | Mak |
| 9,883,877 B2 | 2/2018 | Look et al. |
| 9,901,435 B2 | 2/2018 | Janardhan et al. |
| 9,915,674 B2 | 3/2018 | Zordan |
| 9,943,321 B2 | 4/2018 | Nita |
| 9,956,326 B2 | 5/2018 | Ramella et al. |
| 9,999,710 B2 | 6/2018 | Ross et al. |
| 10,219,814 B2 | 3/2019 | Feltyberger et al. |
| 10,238,789 B2 | 3/2019 | Kuntz et al. |
| 10,251,739 B2 | 4/2019 | Janardhan et al. |
| D847,864 S | 5/2019 | Janardhan et al. |
| D847,865 S | 5/2019 | Janardhan et al. |
| D847,866 S | 5/2019 | Janardhan et al. |
| D850,490 S | 6/2019 | Janardhan et al. |
| 10,335,260 B2 | 7/2019 | Janardhan et al. |
| 10,342,655 B2 | 7/2019 | Janardhan et al. |
| 10,390,926 B2 | 8/2019 | Janardhan et al. |
| 10,463,468 B2 | 11/2019 | Janardhan et al. |
| 10,517,617 B2 | 12/2019 | Aklog et al. |
| 10,531,883 B1 | 1/2020 | Deville et al. |
| 10,722,253 B2 | 7/2020 | Deville et al. |
| 10,751,159 B2 | 8/2020 | Janardhan et al. |
| D896,847 S | 9/2020 | Janardhan et al. |
| 10,799,669 B2 | 10/2020 | Chou et al. |
| 10,946,123 B2 | 3/2021 | Christensen et al. |
| 11,020,133 B2 | 6/2021 | Wilson et al. |
| 11,052,006 B2 | 7/2021 | Tanaka |
| 11,065,019 B1 | 7/2021 | Chou et al. |
| 11,071,812 B2 | 7/2021 | Raman et al. |
| 11,096,703 B2 | 8/2021 | Panian |
| 11,096,712 B2 | 8/2021 | Teigen et al. |
| 11,197,683 B1 | 12/2021 | Teigen et al. |
| 11,298,144 B2 | 4/2022 | Janardhan et al. |
| 11,337,712 B2 | 5/2022 | Teigen et al. |
| 11,337,855 B2 | 5/2022 | Bandhauer et al. |
| 11,406,402 B2 | 8/2022 | Deville et al. |
| 11,432,835 B2 | 9/2022 | Shaffer et al. |
| 11,436,806 B1 | 9/2022 | Katz et al. |
| 11,490,911 B2 | 11/2022 | Panian |
| 11,497,523 B2 | 11/2022 | Trosper et al. |
| 11,523,830 B2 | 12/2022 | Tompkins et al. |
| 11,547,426 B2 | 1/2023 | Deville et al. |
| 11,553,935 B2 | 1/2023 | Buck et al. |
| 11,586,276 B2 | 2/2023 | Winold et al. |
| 11,730,499 B1 | 8/2023 | Thio et al. |
| 11,759,219 B2 | 9/2023 | Teigen et al. |
| 11,890,024 B2 | 2/2024 | Panian |
| 11,918,240 B2 | 3/2024 | Deville et al. |
| 2003/0069549 A1 | 4/2003 | MacMahon et al. |
| 2005/0085769 A1 | 4/2005 | MacMahon et al. |
| 2005/0124969 A1 | 6/2005 | Fitzgerald et al. |
| 2006/0058837 A1 | 3/2006 | Bose et al. |
| 2007/0038100 A1 | 2/2007 | Nita |
| 2007/0135832 A1 | 6/2007 | Wholey et al. |
| 2007/0166180 A1 | 7/2007 | Adahan |
| 2007/0239261 A1 | 10/2007 | Bose et al. |
| 2007/0269321 A1 | 11/2007 | Adahan |
| 2008/0004545 A1 | 1/2008 | Garrison |
| 2008/0015478 A1 | 1/2008 | Bose |
| 2008/0051708 A1 | 2/2008 | Kumar et al. |
| 2008/0056915 A1 | 3/2008 | Adahan |
| 2008/0319355 A1 | 12/2008 | Nita |
| 2009/0005747 A1 | 1/2009 | Michaels et al. |
| 2009/0030400 A1 | 1/2009 | Bose et al. |
| 2009/0187131 A1 | 7/2009 | Fitzgerald et al. |
| 2009/0318892 A1 | 12/2009 | Aboytes et al. |
| 2010/0114017 A1 | 5/2010 | Lenker et al. |
| 2010/0191178 A1 | 7/2010 | Ross et al. |
| 2010/0204672 A1 | 8/2010 | Lockhart et al. |
| 2010/0217276 A1 | 8/2010 | Garrison et al. |
| 2010/0280434 A1 | 11/2010 | Raney et al. |
| 2011/0137231 A1 | 6/2011 | Sorensen et al. |
| 2011/0160621 A1 | 6/2011 | Nita |
| 2011/0160761 A1 | 6/2011 | Ferrera et al. |
| 2011/0184454 A1 | 7/2011 | Barry et al. |
| 2011/0213290 A1 | 9/2011 | Chin et al. |
| 2011/0213392 A1 | 9/2011 | Aklog et al. |
| 2011/0264133 A1 | 10/2011 | Hanlon et al. |
| 2011/0313328 A1 | 12/2011 | Nita |
| 2011/0319927 A1 | 12/2011 | Nita |
| 2012/0078140 A1 | 3/2012 | Nita |
| 2012/0078285 A1 | 3/2012 | Griffin |
| 2012/0150147 A1 | 6/2012 | Leynov et al. |
| 2012/0283563 A1 | 11/2012 | Moore et al. |
| 2012/0330196 A1 | 12/2012 | Nita |
| 2013/0304082 A1 | 11/2013 | Aklog et al. |
| 2013/0324882 A1 | 12/2013 | Mescher |
| 2014/0039343 A1 | 2/2014 | Mescher et al. |
| 2014/0128907 A1 | 5/2014 | Hui et al. |
| 2014/0180377 A1 | 6/2014 | Bose et al. |
| 2014/0271273 A1 | 9/2014 | Carpenter |
| 2014/0276897 A1 | 9/2014 | Rockley et al. |
| 2014/0277082 A1 | 9/2014 | Janardhan et al. |
| 2015/0028005 A1 | 1/2015 | Janardhan et al. |
| 2015/0032121 A1 | 1/2015 | Janardhan et al. |
| 2015/0032146 A1 | 1/2015 | Janardhan et al. |
| 2015/0032147 A1 | 1/2015 | Janardhan et al. |
| 2015/0196304 A1 | 7/2015 | Rabkin et al. |
| 2015/0238303 A1 | 8/2015 | Janardhan |
| 2015/0359666 A1 | 12/2015 | Zacharias |
| 2016/0058614 A1 | 3/2016 | Ross et al. |
| 2016/0166265 A1 | 6/2016 | Nita |
| 2017/0021072 A1 | 1/2017 | Forsell |
| 2017/0105743 A1 | 4/2017 | Vale et al. |
| 2017/0112981 A1 | 4/2017 | Friedman et al. |
| 2017/0136158 A1 | 5/2017 | Culhane et al. |
| 2017/0147765 A1 | 5/2017 | Mehta |
| 2017/0151032 A1 | 6/2017 | Loisel |
| 2017/0181760 A1 | 6/2017 | Look et al. |
| 2017/0181761 A1 | 6/2017 | Janardhan et al. |
| 2017/0333060 A1 | 11/2017 | Panian |
| 2017/0360469 A1 | 12/2017 | Janardhan et al. |
| 2018/0049921 A1 | 2/2018 | Sorensen et al. |
| 2018/0085136 A1 | 3/2018 | Janardhan et al. |
| 2018/0197633 A1 | 7/2018 | Mehta |
| 2018/0228502 A1 | 8/2018 | Shaffer et al. |
| 2018/0256797 A1 | 9/2018 | Schenck et al. |
| 2018/0263646 A1 | 9/2018 | Loisel |
| 2018/0338770 A1 | 11/2018 | Mogi et al. |
| 2018/0339130 A1 | 11/2018 | Ogle |
| 2019/0133745 A1 | 5/2019 | Janardhan et al. |
| 2019/0142567 A1 | 5/2019 | Janardhan et al. |
| 2019/0142568 A1 | 5/2019 | Janardhan et al. |
| 2019/0167406 A1 | 6/2019 | Janardhan et al. |
| 2020/0046368 A1 | 2/2020 | Merritt et al. |
| 2020/0297362 A1 | 9/2020 | Deville et al. |
| 2020/0397956 A1 | 12/2020 | Luxon et al. |
| 2020/0397957 A1* | 12/2020 | Teigen .............. A61B 17/22 |
| 2021/0099344 A1 | 4/2021 | Janardhan et al. |
| 2021/0137540 A1 | 5/2021 | Panian |
| 2021/0186534 A1 | 6/2021 | Hunt et al. |
| 2021/0378691 A1 | 12/2021 | Panian |
| 2022/0054151 A1 | 2/2022 | Shifflette |
| 2022/0168000 A1 | 6/2022 | Nagireiter et al. |
| 2022/0168001 A1 | 6/2022 | Nagireiter et al. |
| 2022/0168002 A1 | 6/2022 | Nagireiter et al. |
| 2022/0280171 A1 | 9/2022 | Teigen et al. |
| 2022/0296260 A1 | 9/2022 | Janardhan et al. |
| 2022/0296261 A1 | 9/2022 | Panian |
| 2022/0313288 A1 | 10/2022 | Janardhan et al. |
| 2022/0323096 A1* | 10/2022 | Naglreiter .............. A61B 17/22 |
| 2022/0330958 A1* | 10/2022 | Mobley .............. A61M 1/65 |
| 2022/0378449 A1 | 12/2022 | Look et al. |
| 2023/0000510 A1 | 1/2023 | Brady et al. |
| 2023/0026412 A1 | 1/2023 | Teigen et al. |
| 2023/0043096 A1 | 2/2023 | Panian |
| 2023/0063577 A1 | 3/2023 | Pons |
| 2023/0099283 A1 | 3/2023 | Deville et al. |
| 2023/0100426 A1 | 3/2023 | Deville et al. |
| 2023/0112635 A1 | 4/2023 | Panian |

(56) References Cited

U.S. PATENT DOCUMENTS

| | | |
|---|---|---|
| 2023/0181200 A1 | 6/2023 | Deville et al. |
| 2023/0240694 A1 | 8/2023 | Panian |
| 2024/0000469 A1 | 1/2024 | Teigen et al. |
| 2024/0138858 A1 | 5/2024 | Gamez et al. |
| 2024/0148957 A1 | 5/2024 | Brown et al. |
| 2024/0148958 A1 | 5/2024 | Reyes et al. |
| 2024/0285292 A1 | 8/2024 | Hanser et al. |

FOREIGN PATENT DOCUMENTS

| | | |
|---|---|---|
| WO | WO 2012/057881 A1 | 5/2012 |
| WO | WO 2014/151209 A1 | 9/2014 |
| WO | WO 2015/157330 A1 | 10/2015 |
| WO | WO 2016/018448 A1 | 2/2016 |
| WO | WO 2017/134462 A1 | 8/2017 |
| WO | WO 2023/220633 A2 | 11/2023 |
| WO | WO 2024/016004 A2 | 1/2024 |

OTHER PUBLICATIONS

International Search Report and Written Opinion for PCT/US2024/015950, mailed Aug. 7, 2024.

Office Action for U.S. Appl. No. 18/596,868, mailed Sep. 10, 2024.

U.S. Appl. No. 18/123,973, filed Mar. 20, 2023; Applicant: Von Vascular, Inc.

Mathews, S. Jay et al. "The Akura Thrombectomy Catheter System for the Treatment of VTE," Insert to Endovascular Today, vol. 23, No. 1, Jan. 2024 (4 pages).

* cited by examiner

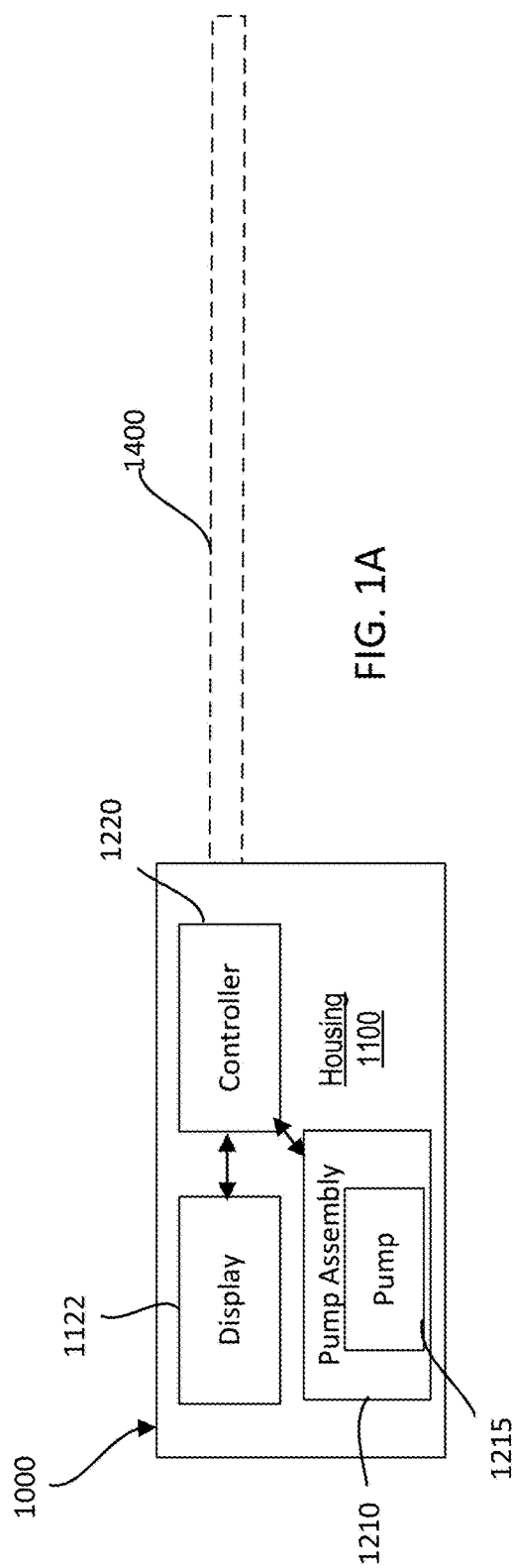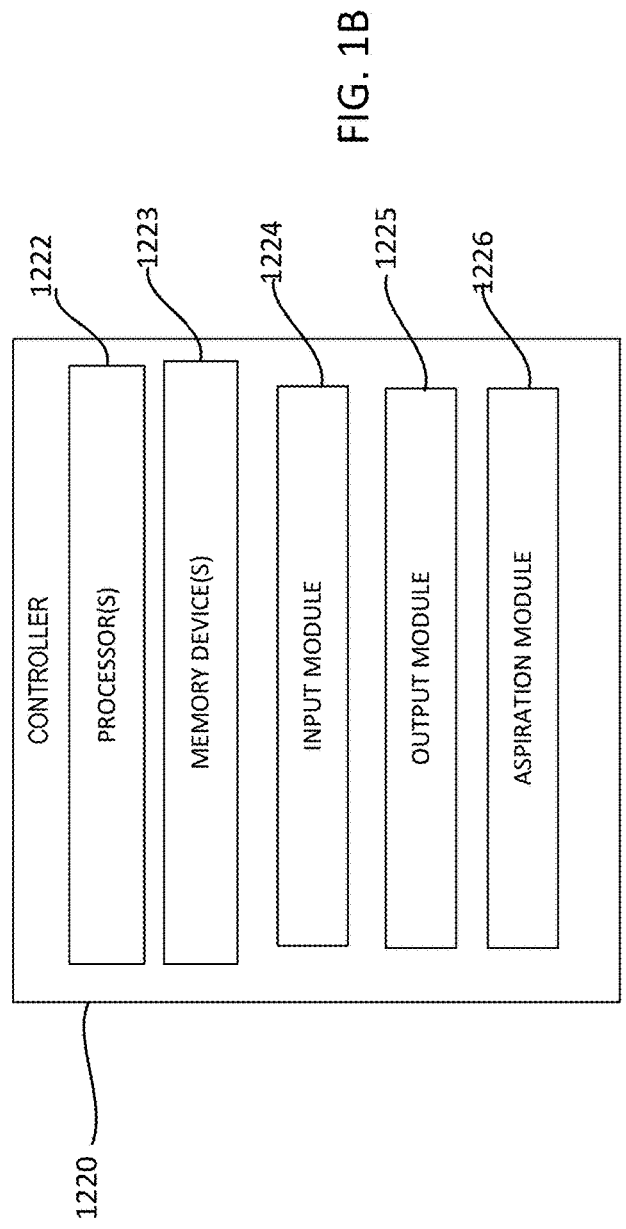

Select the inner diameter range (in)

Company:

| 0.032 - 0.039 | 0.040 - 0.045 | 0.046 - 0.052 |
| --- | --- | --- |
| 0.053 - 0.055 | 0.059 - 0.063 | 0.064 - 0.068 |
| 0.069 - 0.071 | 0.072 - 0.081 | 0.082 - 0.090 |
| 0.091 - 0.096 | 0.097 - 0.124 | 0.125 - 0.131 |

BACK

Proprietary marks are property of their respective owners.

FIG. 1F

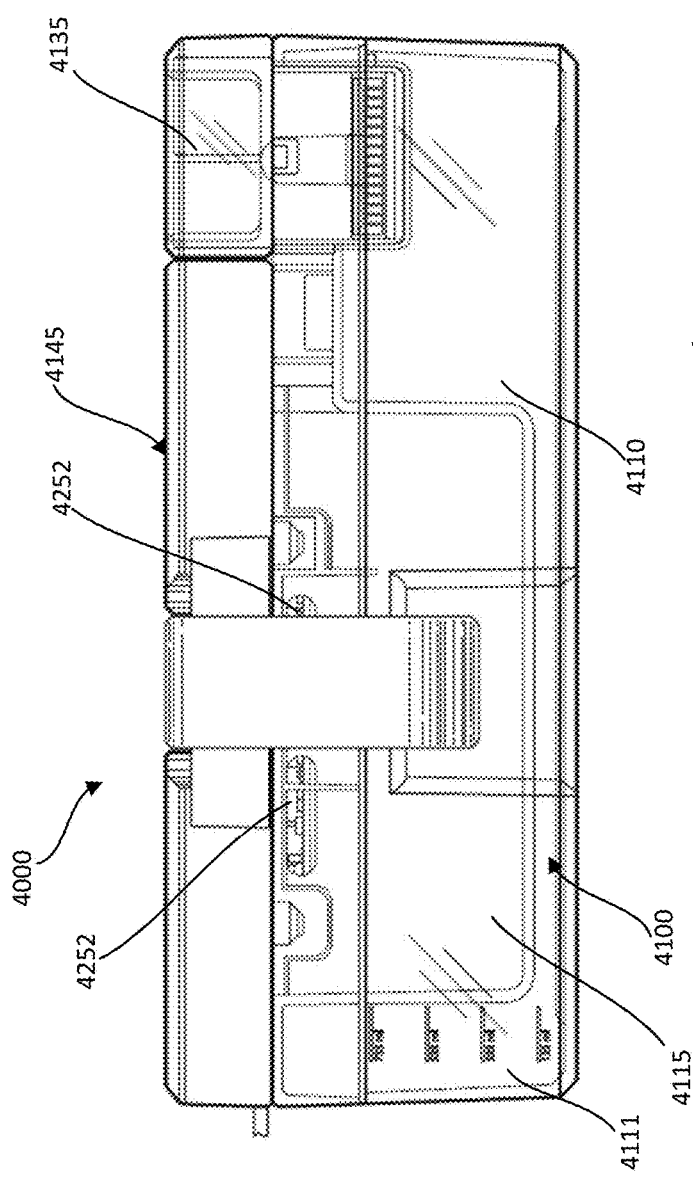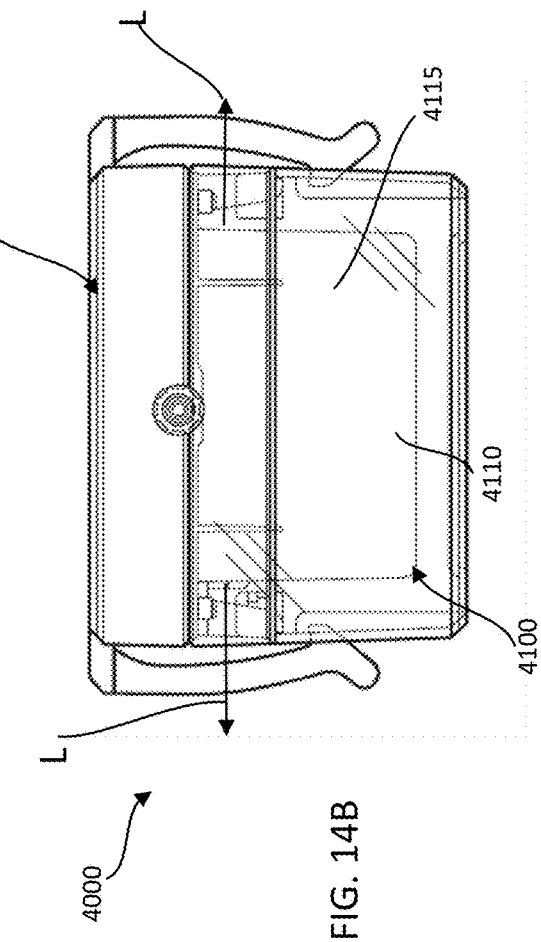

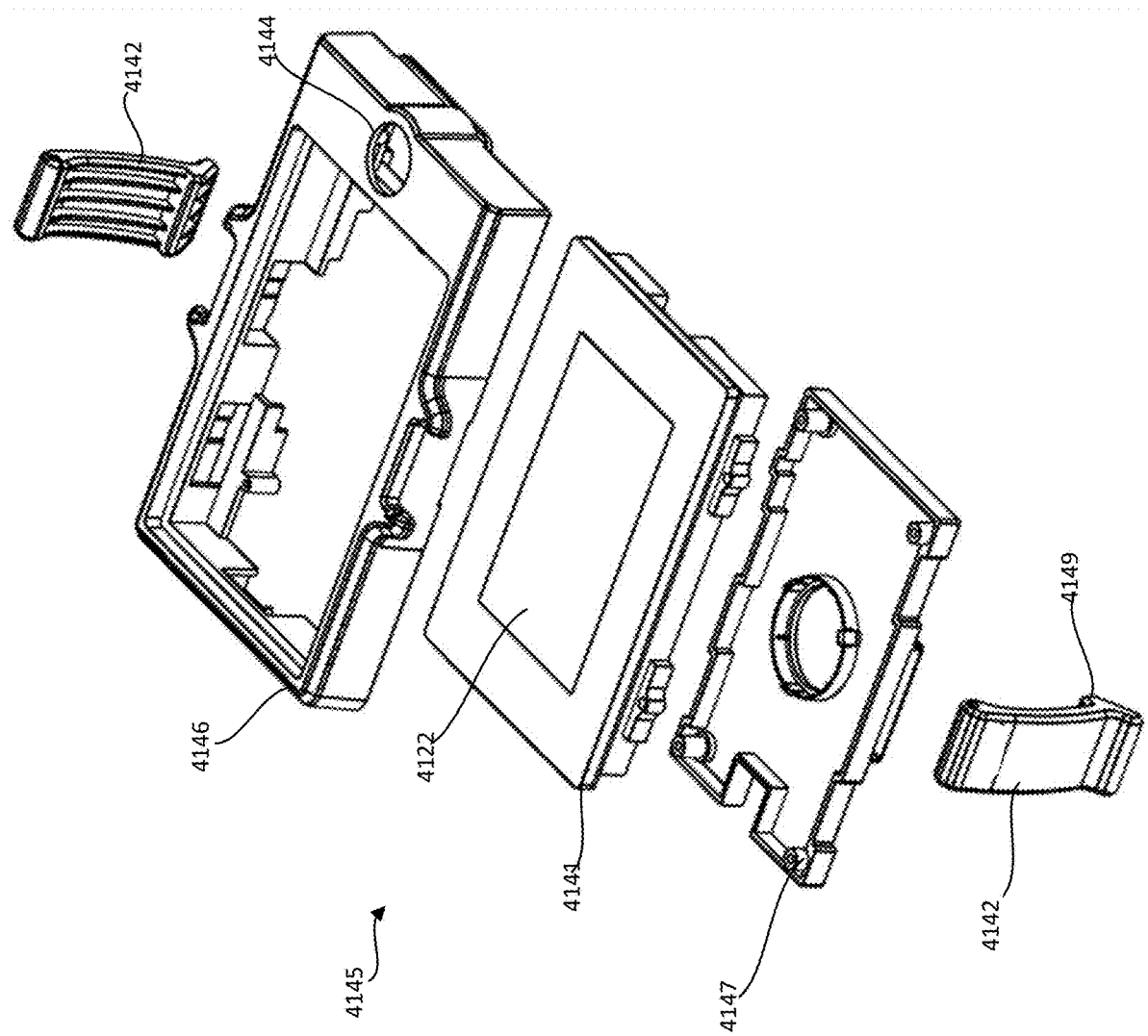

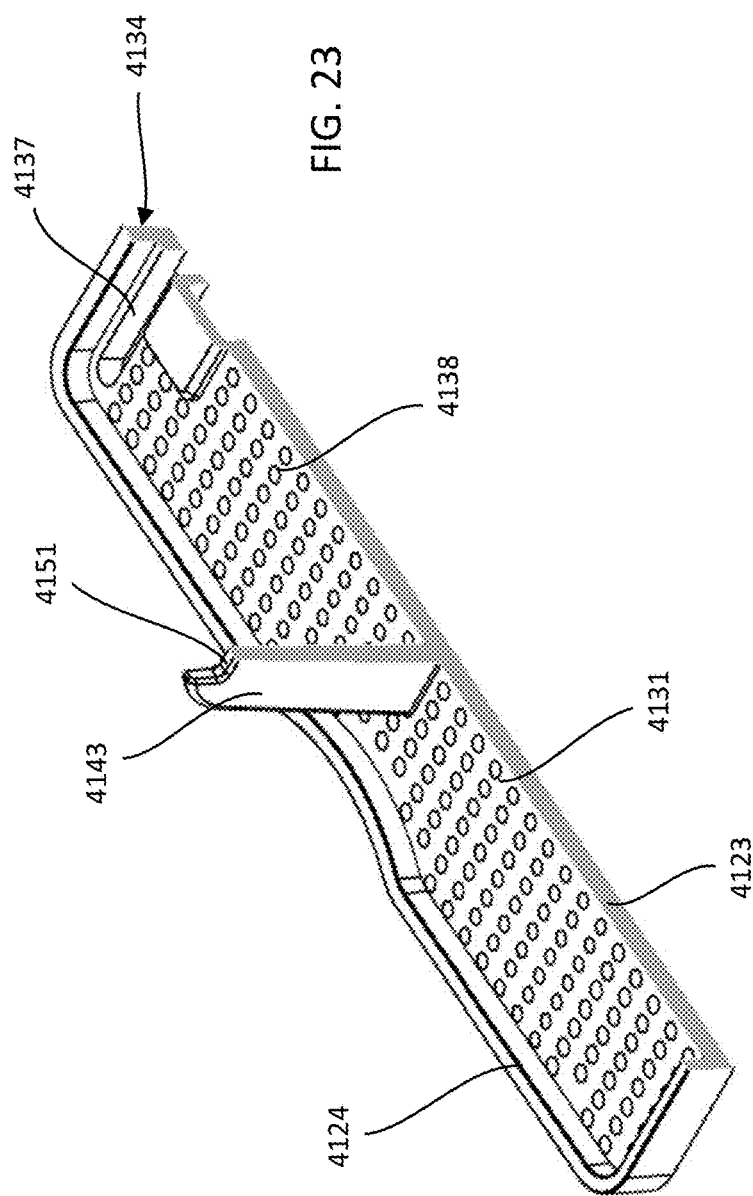
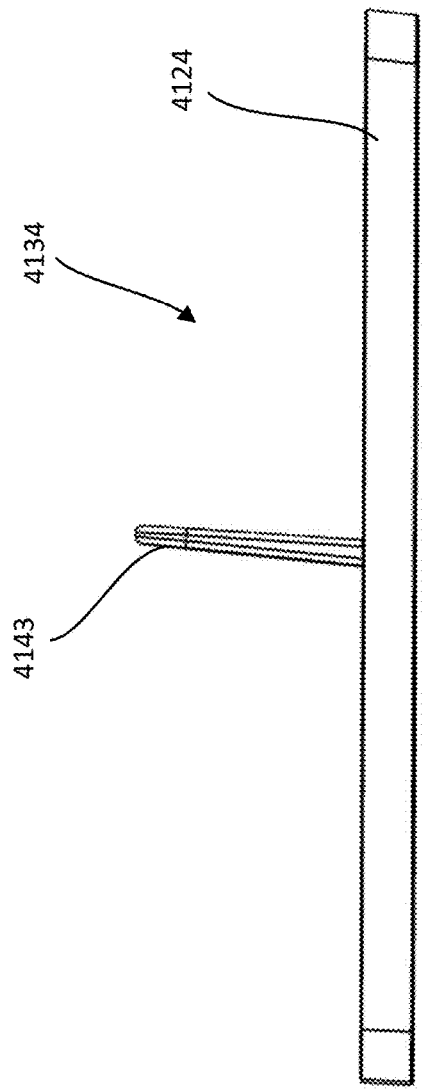
FIG. 23
FIG. 24

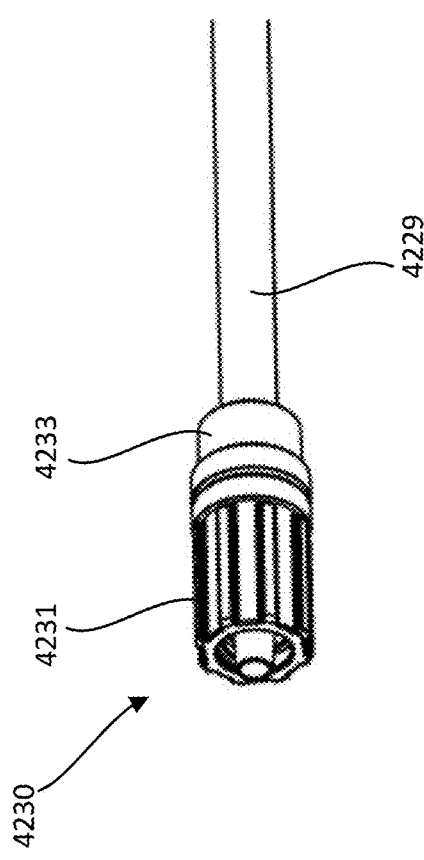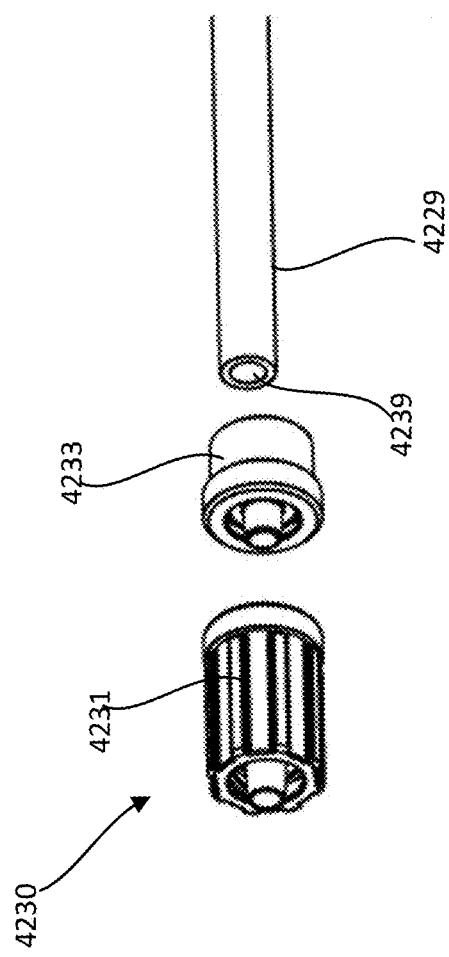

SYSTEM, DEVICES AND METHODS FOR REMOVING OBSTRUCTIONS IN BODY LUMENS

CROSS-REFERENCE TO RELATED APPLICATIONS

This application is a continuation of U.S. patent application Ser. No. 18/596,868, entitled "System, Devices and Methods for Removing Obstructions in Body Lumens," filed Mar. 6, 2024, which is a continuation of International Application No. PCT/US2024/015950, entitled "System, Devices and Methods for Removing Obstructions in Body Lumens," filed Feb. 15, 2024, and a continuation-in-part of U.S. patent application Ser. No. 18/373,955, entitled "Sterile Field Clot Catcher Device, Module and Methods," filed Sep. 27, 2023, which is a continuation-in-part of U.S. patent application Ser. No. 18/123,973, entitled "Adaptive Pressure-Cyclical Aspiration Device and Methods," filed Mar. 20, 2023, which claims priority to U.S. Provisional Application No. 63/321,706, entitled "Novel Enhanced Acute Ischemic Stroke Aspiration Energy Source," filed Mar. 20, 2022, U.S. Provisional Application No. 63/325,778, entitled "Novel Enhanced Acute Ischemic Stroke Aspiration Energy Source," filed Mar. 31, 2022, and U.S. Provisional Application No. 63/335,168, entitled "Novel Enhanced Aspiration Source," filed Apr. 26, 2022, and U.S. Provisional Application No. 63/474,167, entitled "Algorithms for Novel Enhanced Aspiration Source," filed Jul. 26, 2022, the disclosures of each of which are incorporated herein by reference in its entirety.

BACKGROUND

The embodiments described herein relate to medical instruments, and more specifically to medical instruments and methods related to improved acute ischemic event therapies, and devices and methods for implementing such therapies to effectively and efficiently remove an obstruction (e.g., blood clot) in a vessel.

Conventional thrombotic extraction procedures for removing a clot occluding a blood vessel have routinely applied static aspiration. In such conventional procedures, problems can arise from plugging of the catheter used to extract the clot, thereby rendering continued use of the catheter essentially ineffective.

For example, when trying to aspirate a clot that is larger than the catheter, the clot often plugs the catheter according to a static aspiration approach. In particular, the clot is pulled partially into the catheter along a length thereof. The longer this length, the greater the friction that is present between the clot and the inner diameter (ID) of the catheter. When the applied vacuum is alleviated or entirely discontinued, the clot expands slightly, but sufficiently to push outward on the ID of the catheter, resulting in a risk that the catheter will remain plugged and consequently rendered unable to effectively aspirate the clot if vacuum is restored.

By focusing upon static suction operating at or near full vacuum, for example, about −29.2 inHg (−98.9 kPa), without helpful or effective indication of tip activity, existing systems and devices have often lacked continuous feedback of conditions of the aspiration catheter. Although cyclic aspiration patterns have been used, such known systems can often have limitations and therefore be less effective.

Known systems that use constant, low vacuum can have negative patient outcomes due to, for example, aspiration of too much blood during the procedure, and/or use of high vacuum pressure that can cause larger thrombus to be lodged into the catheter, thus necessitating removal of the catheter from the patient to dislodge the clot. Removing the catheter can take valuable time and may require multiple catheter insertions to clear the blockage. Further, excessive vacuum pressure may cause catheter walls to collapse, thereby limiting the ability to aspirate the thrombus.

Some systems use cyclic pressure to perform aspiration and remove thrombus. Such systems often have limited control of the pressure cycles, which, in certain circumstances, can cause the thrombus to be inadvertently pushed further distal from the catheter resulting in undesired patient outcomes. Continued pressure cycling on the condition that the thrombus is lodged within the catheter can also expend unnecessary energy and/or cause the catheter wall to collapse. Moreover, if the tip is in proximity to a side wall of the vessel, systems having limited control can result in perforation of or other damage to the vessel side wall.

In addition, known systems may not be compatible with different catheters and instead may require the use of dedicated catheter tubing sets. For example, the use of thinner walled/more compliant catheters with a system that is calibrated for use with thicker walled/more rigid catheters may result in the catheter collapsing inward due to excessive pressure cycling, thereby falsely indicating that the catheter is plugged with the target thrombus. Thus, such known systems can limit the ability of the surgeon to use a variety of different catheters that may be appropriate for the specific circumstances. Moreover, some conventional aspiration systems employ dedicated catheter tubing sets sold and packaged separately. An additional drawback resides in the fact that the prior art clot extraction approaches are not compatible with neurovascular revascularization stent retrievers.

Moreover, some known systems include a pump that is configured for use outside of the sterile field with tubing and accessories that extend into the sterile field. Such pumps are often relatively large and require A/C power and are therefore not easily configured to be situated near the patient or easily moved during a procedure. Accordingly, the use and control of such known pumps is cumbersome and inefficient.

It would therefore be desirable to provide acute ischemic event therapies and optional wider functional applications which address and overcome these and other drawbacks of prior art approaches.

In addition, known extraction systems can also provide for the containment of the extracted clot, blood and other biological material. In some such systems, however, the container that receives the clot is located outside of the sterile field and remote from the patient during an extraction procedure. Moreover, some known clot receiving containers do not provide for effective viewing of the interior contents of the container by the user. Such systems make it difficult for the user to view and examine the clot and/or other biological material during the extraction procedure. Such information can be useful to the user, for example, to assist in making adjustments to the treatment during the procedure.

Some known clot aspiration systems typically have clot retrieval/collection devices disposed in-line with the suction path. This requires the user to stop the suction pump to retrieve the clot. With such approaches, clot retrieval for observation, examination and identification requires a stoppage of the clot removal aspiration process. This results in critical delay in time sensitive therapeutic procedures often to the determent of the patient being treated.

Thus, a need exists for improved systems and methods for removing obstructions from vessels, including systems and methods with control of pressure cycling and the ability to operate with different catheters. It is also desirable to create a system and method which can allow a user to view and examine a clot within a clot waste container during an extraction procedure without having to halt the pump or the procedure. It would also be desirable to have a clot waste container that is easily removable from the pump assembly to allow for easy disposal of the material within the clot waste container.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, a method is provided for aspirating a thrombus from a body lumen via a catheter coupled to a pump assembly that includes a pump. The method includes receiving at an aspiration module of the pump assembly an input associated with a catheter parameter associated with the catheter coupled to the pump assembly. The aspiration module is implemented in at least one of a memory or a processor operably coupled to the pump assembly. An aspiration profile associated with the catheter parameter is selected via the aspiration module from a list of a plurality of preset aspiration profiles. Each aspiration profile from the list of preset aspiration profiles is associated with a different catheter. The aspiration profile includes an upper pressure limit, a lower pressure limit, an aspiration speed, and an infusion speed. A first plurality of signals is sent to actuate the pump based on the aspiration profile to operate the pump in a first mode. A pressure signal associated with a catheter pressure from a sensor of the pump assembly is received at the aspiration module. A second plurality of signals to actuate the pump based on the aspiration profile to operate the pump in a second mode is sent via the aspiration module. In the second mode the pump is cycled between the aspiration speed and the infusion speed such that the catheter pressure cycles between the upper pressure limit and the lower pressure limit.

In some embodiments, the aspiration speed is different than the infusion speed. In some embodiments, the infusion speed is less than the aspiration speed. In some embodiments, the infusion speed is between 40% and 90% of the aspiration speed.

In some embodiments, an apparatus includes a thrombectomy pump assembly including a pump disposed within a housing and a display coupled to the housing. An aspiration controller is coupled within the housing and includes an input module and an aspiration module. The input module is implemented in at least one of a memory or a processor of the aspiration controller and is configured to receive a first input. The first input is associated with a catheter parameter associated with a catheter to be coupled to the pump assembly. The aspiration module is configured to (1) select an aspiration profile associated with the catheter parameter from a list of a plurality of preset aspiration profiles each associated with a different catheter. The aspiration profile includes an upper pressure limit, a lower pressure limit, an aspiration speed, and an infusion speed. The aspiration module is configured to (2) send a first plurality of signals based on the aspiration profile to the thrombectomy pump assembly to operate the thrombectomy pump assembly in a first mode, and (3) receive a pressure signal associated with a catheter pressure from a sensor of the thrombectomy pump assembly. The aspiration module is configured to (4) send a second plurality of signals based on the aspiration profile to the thrombectomy pump assembly to operate the thrombectomy pump assembly in a second mode. During the second mode the pump is cycled between the aspiration speed and the infusion speed such that the catheter pressure cycles between the upper pressure limit and the lower pressure limit.

In some embodiments, the aspiration controller is further configured to receive the input associated with the catheter parameter from a list of selectable catheters. In some embodiments, the catheter parameter includes at least one of an inner diameter of the catheter, a compliance of the catheter, a tip configuration of the catheter, or a length of the catheter.

In some embodiments, the aspiration controller is configured to receive, after the sending the second plurality of signals to the pump assembly to operate the pump assembly in the second mode, a second pressure signal associated with a second catheter pressure from the sensor of the pump assembly. The aspiration control is configured to send a third plurality of signals to the pump assembly to operate the pump assembly in a third mode based on the selected aspiration profile, the third mode includes operating the pump at the aspiration speed.

In some embodiments, a non-transitory storage medium that stores a program causing a processor to execute a method of aspirating a thrombus from a body lumen via a catheter coupled to a pump assembly including a pump, includes receiving at an aspiration module of the pump assembly an input associated with a catheter parameter associated with the catheter coupled to the pump assembly. An aspiration profile associated with the catheter parameter is selected via the aspiration module from a list of a plurality of preset aspiration profiles. The list of preset aspiration profiles each being associated with a different catheter. The aspiration profile includes an upper pressure limit, a lower pressure limit, an aspiration speed, and an infusion speed. A first plurality of signals is sent to actuate the pump based on the aspiration profile to operate the pump in a first mode. A pressure signal associated with a catheter pressure from a sensor of the pump assembly is received as the aspiration module. A second plurality of signals to actuate the pump based on the aspiration profile to operate the pump in a second mode is sent via the aspiration module. In the second mode the pump is cycled between the aspiration speed and the infusion speed such that the catheter pressure cycles between the upper pressure limit and the lower pressure limit.

In some embodiments, a method of removing a thrombus from a body lumen via a catheter coupled to a pump assembly, the pump assembly including a pump, includes selecting, via an aspiration module, an aspiration profile including an upper pressure limit, a lower pressure limit, an aspiration speed, and an infusion speed. A first plurality of signals is sent via the aspiration module to the pump assembly to operate the pump assembly in a first mode based on the aspiration profile. The first mode includes operating the pump at the aspiration speed. A first pressure signal associated with a catheter pressure is received from a sensor of the pump assembly. A second plurality of signals is sent in response to the first pressure signal and via the aspiration module to the pump assembly to operate the pump assembly in a second mode based on the aspiration profile. During the second mode, the pump is cycled between the aspiration speed and the infusion speed such that the catheter pressure cycles between the upper pressure limit and the lower pressure limit. A second pressure signal associated with a second catheter pressure is received from the sensor of the pump assembly. A third plurality of signals is sent in response to the first pressure signal and to the pump assembly to operate the pump assembly in a third mode based on the aspiration profile. The third mode including operating the pump at the aspiration speed.

In some embodiments, a method of removing a thrombus from a body lumen via a catheter coupled to a pump assembly, the pump assembly including a pump, includes sending, via an aspiration module operably coupled to the pump assembly, a set of signals to the pump assembly to operate the pump assembly in a cycling extraction mode. In the cycling extraction mode the pump is cycled between an aspiration speed and an infusion speed for a set of cycles such that a catheter pressure cycles between an upper pressure limit and a lower pressure limit. A cycle time ratio of an aspiration time to an infusion time for each cycle of the plurality of cycles is determined at the aspiration module. A notification to reposition a tip of the catheter on a condition that the cycle time ratio is within a ratio range over a threshold number of cycles of the set of cycles is sent.

In some embodiments, the notification indicates that a tip of the catheter may be in contact with a side wall of the body lumen. The method further includes displaying a user input prompt on a display screen, the user input prompt soliciting a user input after the tip of the catheter is repositioned.

In some embodiments, the set of signals is a first set of signals and the notification is a first notification. The method further includes receiving at the aspiration module the user input associated with the tip of the catheter being repositioned. A second set of signals is sent to operate the pump in an aspiration mode in response to the user input. A pressure signal associated with a catheter pressure from a sensor of the pump assembly is received at the aspiration module. A second notification indicating that the tip of the catheter was likely in contact with the side wall of the body lumen is sent on a condition that the pressure signal is above a pressure threshold.

In some embodiments, a method of removing a thrombus from a body lumen via a catheter coupled to a pump assembly, the pump assembly including a pump, includes advancing a tip of the catheter into proximity with one of the thrombus within the body lumen or a side wall of the body lumen such that the pump operates in a cycling extraction mode. In the cycling extraction mode the pump is cycled between an aspiration speed and an infusion speed for a set of cycles. A catheter pressure cycles between an upper pressure limit and a lower pressure limit when the pump is operating in the cycling extraction mode. A notification to reposition the tip of the catheter is received at a display screen operably coupled to the pump. The notification is received on a condition that a cycle time ratio of an aspiration time to an infusion time for each cycle of the set of cycles is within a ratio range over a threshold number of cycles.

In some embodiments, the notification includes an image showing the catheter pressure as a function of time.

In some embodiments, a method of aspirating a thrombus from a body lumen via a catheter coupled to a pump assembly, the pump assembly including a pump, includes sending, via an aspiration module operably coupled to the pump assembly, a set of signals to the pump assembly to operate the pump assembly in a cycling extraction mode. In the cycling extraction mode the pump is cycled between an aspiration speed and an infusion speed for a set of cycles such that the catheter pressure cycles between an upper pressure limit and a lower pressure limit. A period for each cycle of the plurality of cycles is determined at the aspiration module. A change in the period between each successive cycle of the set of cycles is determined at the aspiration module. The method includes sending a notification on a condition that the change in the period exceeds a period limit over a threshold number of cycles of the set of cycles.

In some embodiments, the notification prompts a user to check a catheter connection to the pump assembly. The method can further include displaying a user input prompt on a display screen. The user input prompt solicits a user input after the catheter connection has been checked.

In some embodiments, the period limit is a 20 percent change in the period between an average period of a first subset of cycles within the set of cycles and an average period of a second subset of cycles within the set of cycles.

In some embodiments, a method of removing a thrombus from a body lumen includes advancing a tip of a catheter into proximity with the thrombus within the body lumen while the catheter is coupled to a pump assembly operating in an aspiration mode. A first notification indicating that the thrombus is in a plugged state within the tip of the catheter is received at a display screen operably coupled to the pump assembly. The tip of the catheter and the thrombus is withdrawn in response to receiving the first notification. A second notification indicating that the plugged state of the thrombus is compromised is received at a display screen operably coupled to the pump assembly. The method further includes stopping withdrawal of the tip of the catheter in response to receiving the second notification.

In some embodiments, the method includes injecting, after the stopping withdrawal, a contrast solution associated with an angiographic imaging system via the catheter within the body lumen. The injecting can include decoupling the pump assembly from the catheter and coupling the catheter to a source of the contrast solution.

In some embodiments, the display screen is a first display screen. The method further includes receiving, at a second display screen, an angiographic image of body lumen. The tip of a catheter is advanced within the body lumen in response to the receiving the angiographic image.

In some embodiments, the first notification is produced on condition that a catheter pressure measured by the pump assembly is below a preset pressure limitation indicating the plugged state. In some embodiments, the first notification is produced on condition that a time period of operating the pump assembly in a pressure cycling mode has exceeded a time threshold, indicating the plugged state. In some embodiments, the preset pressure limitation is a first preset pressure limitation. The second notification is produced on condition that the catheter pressure measured by the pump assembly rises above a second preset pressure limitation.

In some embodiments, a method of removing a thrombus from a body lumen via a catheter coupled to a pump assembly includes sending, via an aspiration module operably coupled to the pump assembly, a first set of signals to the pump assembly to operate the pump assembly in a cycling extraction mode. In the cycling extraction mode the pump is cycled between an aspiration speed and an infusion speed for a set of cycles such that a catheter pressure cycles between an upper pressure limit and a lower pressure limit. A first notification indicating that the thrombus is in a plugged state within the tip of the catheter is sent to a display screen operably coupled to the pump assembly. The first notification prompts the user to withdraw the catheter tip from the body lumen on condition that a time period of operating the pump assembly in the cycling extraction mode has exceeded a time threshold. A second plurality of signals is sent to operate the pump in an aspiration mode. A pressure signal associated with a catheter pressure from a sensor of the pump assembly is received at the aspiration module. A second notification indicating that the plugged state of the thrombus is compromised is sent to the display screen on condition that the catheter pressure rises above a preset pressure limitation.

In some embodiments, an apparatus includes a housing including a pump cavity and a waste volume. The pump cavity is configured to receive a thrombectomy pump. A clot retainer is removably coupled to the housing within the waste volume. The clot retainer has a surface with a first portion defining a plurality of openings sized to allow liquid to flow through the surface and into the waste volume, and a second portion defining a bypass opening. A lid is removably coupled to the housing to cover the clot retainer and includes a transparent portion to allow viewing of the clot retainer through the lid.

In some embodiments, the housing has a base surface. The first portion of the surface of the clot retainer is disposed at a first distance from the base surface of the housing and the second portion of the surface of the clot retainer is disposed at a second distance from the base surface of the housing. The second distance is greater than the first distance. In some embodiments, the housing defines an outlet port in a side wall of the housing between the pump cavity and the waste volume at a third distance from the base surface. The third distance is greater than the first distance. The outlet port is in fluid communication with the waste volume of the housing. In some embodiments, a centerline of the outlet port extends parallel with the bottom surface of the clot retainer.

In some embodiments, an apparatus includes a housing including a first housing portion defining a pump cavity and a second housing portion defining a waste volume. The waste volume is at least partially surrounding the first housing portion. A pump assembly is disposed within the pump cavity and includes an inlet port configured to be coupled to a catheter and an output port in fluid communication with the waste volume. The pump assembly includes a pump, a motor to drive the pump, a sensor, and a controller. A cover is coupled to the first housing portion and encloses the pump cavity and a display screen is coupled to the cover and operably coupled to the controller.

In some embodiments, the apparatus includes a switch coupled to the pump assembly. The switch is configured to send an indication to the controller when the pump assembly has been decoupled from the housing. The controller is configured to automatically shut off the pump assembly based on the receipt of the indication.

In some embodiments a method of removing a thrombus from a body lumen of a patient during a thrombectomy procedure on the patient includes advancing a catheter into the body lumen and actuating a thrombectomy pump system coupled to the catheter to apply a suction pressure to aspirate the thrombus from the body lumen via the catheter. The thrombectomy pump system being within a sterile field during the thrombectomy procedure. The thrombectomy pump system includes a pump assembly including a pump coupled within a housing, a waste volume defined by the housing, and a clot retainer removably coupled to the housing within the waste volume. The method further includes viewing the thrombus captured on the clot retainer via a transparent lid removably coupled to the housing and covering the waste volume.

In some embodiments, a method of aspirating a thrombus from a body lumen via a catheter coupled to a pump assembly including a pump includes selecting, via an aspiration module, an aspiration profile. The aspiration profile including an upper pressure limit, a lower pressure limit, an aspiration speed, and an infusion speed. A first plurality of signals is sent via the aspiration module to the pump assembly to operate the pump assembly in a first mode based on the aspiration profile. The first mode includes operating the pump at the aspiration speed. A first pressure signal is received at the aspiration module and is associated with a catheter pressure from a sensor of the pump assembly. A second plurality of signals is sent via the aspiration module to the pump assembly to operate the pump assembly in a second mode based on the aspiration profile. During the second mode the pump is cycled between the aspiration speed and the infusion speed such that the catheter pressure cycles between the upper pressure limit and the lower pressure limit. A second pressure signal is received at the aspiration module and is associated with a second catheter pressure from the sensor of the pump assembly. A third plurality of signals is sent via the aspiration module to the pump assembly to operate the pump assembly in a third mode based on the aspiration profile. The third mode including operating the pump at the aspiration speed.

BRIEF DESCRIPTION OF THE DRAWINGS

FIG. 1A is schematic illustration of a thrombectomy pump system, according to an embodiment.

FIG. 1B is a schematic illustration of a controller of the thrombectomy pump system of FIG. 1A.

FIGS. 1E-1F are each a graphic depiction of one or more user input menus that can be provided to a display of the thrombectomy pump system of FIG. 1A.

FIGS. 2G-2I are plots showing catheter pressure as a function of time for example operation cycles for a thrombectomy pump system according to various embodiments.

FIG. 14A is a front view of the thrombectomy pump system of FIG. 7 shown with a transparent waste container and the lid to the waste container shown transparent.

FIG. 14B is an end view of the thrombectomy pump system of FIG. 7 illustrating a direction of illumination of lights.

FIG. 20 is an exploded view of the cover assembly of FIG. 19.

FIG. 23 is a cross-sectional view of the clot retainer of FIG. 22.

FIG. 24 is a side view of the clot retainer of FIG. 22.

FIG. 29B is an enlarged view of the catheter connector and a portion of the aspiration tube of the pump assembly of FIG. 26.

FIG. 29C is an exploded view of the catheter connector and a portion of the aspiration tube of the pump assembly of FIG. 29B.

DETAILED DESCRIPTION

Figure 1C:
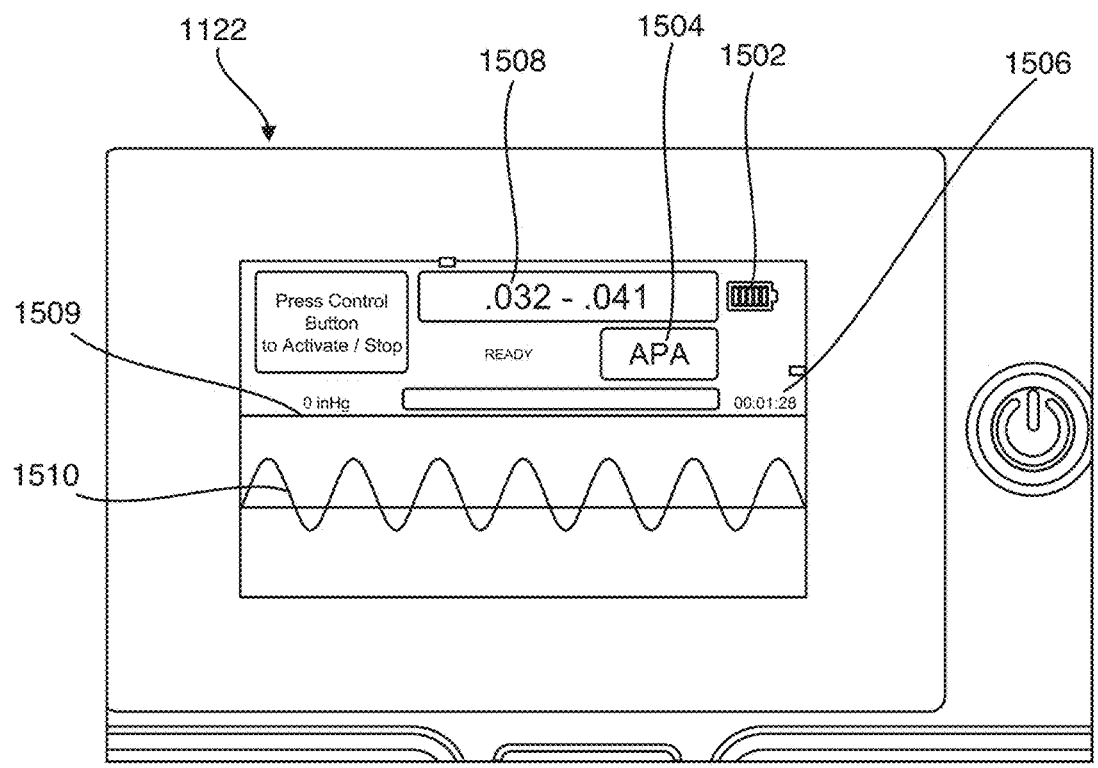
FIGS. 1C-1D are each a graphic depiction of one or more notifications that can be provided to a display of the thrombectomy pump system of FIG. 1A.

As described herein systems, devices and methods are provided for use in the extraction of thrombus from a body lumen via a compact system that can be operated within the sterile field. Such systems can be battery-powered and can be easily monitored, manipulated, moved, and repositioned during operation due to their compact nature and lack of tether to external equipment. Thus, the systems and methods described herein facilitate more efficient and faster thrombus removal procedures. Moreover, the direct connection of the catheter to the pump results in making possible shorter tubing lengths compared with convention aspiration pump systems. Additionally, for example, some systems employ catheter tubing sets sold and packaged separately. In accordance with embodiments of the present invention, the pump system can be supplied with its own connected, sterile tubing.

Embodiments of the present invention optionally provide audiovisual feedback during a thrombotic extraction procedure (i.e., via a video screen). Audio and visually displayed information within the user's reach and line of sight advantageously allows rapid response by the surgeon/operator in selecting operational changes as needed. A speaker can optionally verbally indicate to the operator conditions at the tip of the catheter, and can also give prompts.

Embodiments described herein can include a built-in clot retainer. The clot retainer can be integrated into the pump system, included inside the tubing, or otherwise couplable to the pump. The clot retainer can be positioned within the sterile field for convenient and rapid evaluation of the materials removed. In some embodiments, the system includes an easily removable clot retainer, on-board lighting, and a transparent lid to facilitate rapid inspection of the retrieved materials.

Such systems can also extract the clots via pressure cycling while using minimum energy (i.e., pressure and flow of fluids into and out of the body lumen). In this manner, the energy applied to the body lumen can be tailored to be an effective amount for macerating, disrupting and removing the thrombus, which can limit potential damage or undesired outcomes that can be associated with the use of excessive energy or cycling, such as damage to the vessel wall, undesired collapsing of the catheter wall, and undesired movement of the thrombus downstream (i.e., away from the catheter tip). Limiting the energy expended during thrombus removal can also reduce the amount of blood that is aspirated (e.g., by reducing the aspiration flow rate), which can improve patient outcomes. Limiting the energy expended during thrombus removal can also increase battery life and allow for the procedure to be completed by a battery-powered system.

The thrombotic pump systems described herein can provide the option of applying cyclic aspiration effective for fatiguing a clot occluding a vessel. For example, the pump can be activated to operate in either in a cycling extraction mode (Smart Mode) or continuous aspiration mode (Static Mode) as described in more detail below. Systems, devices and methods are also described in copending U.S. patent application Ser. No. 18/123,973, filed Mar. 20, 2023, and U.S. patent application Ser. No. 18/373,955, filed Sep. 27, 2023, each of the disclosures of which are incorporated herein by reference in its entirety.

In some embodiments, the thrombotic systems can provide pumps able to interface with known and later developed catheters, making them universally smart catheter systems, with optional touchscreen, WiFi, and/or Bluetooth controls for thrombus aspiration and treatment. Similarly stated, the system, devices and methods described herein are adaptable for use with multiple different catheter types and sizes. For example, the system provides for selection of the catheter to be used and provides a predetermined aspiration program corresponding to that selected catheter. In this manner, the systems described herein are compatible with third-party thrombectomy catheters and/or stent retrievers. The pump system is advantageously configured as a sterile, single-use, battery-powered unit that is compatible with aspiration indicated catheters.

The unit advantageously comprises in combination three components in one integrated device, including the components of tubing, a collection canister (reservoir), and an aspiration pump. A pump system according to embodiment of the current invention is advantageously agnostic to a specific catheter, controlled by software developed based upon features of current commercially available aspiration catheters. Thus, the systems described herein can operate as a vacuum/aspiration pump with a compact footprint, and can allow a physician to extract thrombus through their choice of an aspiration thrombectomy catheter or stent retriever catheters adapted to use of aspiration. Specifically, in some embodiments, any of the systems and methods herein are optionally compatible with neurovascular revascularization Stent Retrievers (e.g., for use in an "SR mode").

Briefly stated, the systems and methods described herein employ energy sources with touchscreen enabled control of changes in cyclic forces to efficiently remove thrombus. In some embodiments, the systems and methods described herein include AI-based algorithms guided by human medical intervention to support universal aspiration catheter interfacing for acute stroke therapy. According to embodiments, universally interfaced cyclic algorithms drive use of any known or developed aspiration catheters to treat acute ischemic stroke by providing a novel enhanced energy source.

In some embodiments, an aspiration system comprises a pressure controllable pump system (conveniently in a form of an integrated pump device), including a peristaltic pump driven by a stepper motor. A sensor is advantageously included and is used to measure the fluid pressure in the catheter. The measured pressure value serves to provide feedback to control logic, which decides if the pump should generate positive or negative pressure to extract the clot. A combination of positive and negative pressures effectively forces the clot to reliably degrade and pass through the catheter. Specifically, the pressure sensor provides the measured information to a system microprocessor, which in turn instructs the pump to vary the amount and type of aspiration according to predetermined parameters. This feature advantageously mitigates patient blood loss, and provides a facilitated means for disrupting the morphology of the thrombus, resulting in effective thrombus removal and a decrease in catheter blockage.

In some embodiments, the system can automatically shut off when a clot is cleared resulting in less patient blood loss. The blood displacement when operating in the Static Mode can be monitored and thus the blood loss can be significantly less than in conventional aspiration systems.

In some embodiments, the control system determines the performance state of the pump and optionally instructs the pump to operate as a purely static aspiration device, or as a smart device that uses the pressure sensor to determine how to best remove a clot. In accordance with this optional embodiment, there are two operational modes. These include employment of a Smart Mode that uses an Adaptive Pulsative Algorithm (APA) and a Static Mode in which the pump aspirates at uniformly maintained vacuum with no (or limited) feedback from the provided pressure sensor. Similarly stated, the Smart Mode employs a pressure sensor output and a controller to adjust the operation of the pump, whereas the continuous aspiration mode (Static Mode) is consistent with the actions of single-mode commercially available static aspiration pumps. Embodiments according to the invention are capable of producing a vacuum pressure of at least full vacuum (e.g., −29.2 inHg; −98.9 kPa), and capable of being set to a steady vacuum in Static Mode (in addition to the cyclic Smart Mode that uses APA for particular selected catheter.

For example, in the case that the clot happens to plug the catheter, the algorithm produces instruction to the pump to switch to a purely negative pressure mode (uniform vacuum) for a given time. If the pressure sensor indicates that the plugged or corked condition has changed, then the logic reverts back to a cyclical pressure mode for extracting the clot, sending corresponding instructions to the peristaltic pump.

If the measured pressure remains below a specified value, the system assumes that the clot has fully corked the catheter, and a message screen directs the user to remove the catheter while the pump is in constant aspiration mode (negative pressure), for example, full vacuum as employed in conventional systems.

In one mode of operation (referred to a Smart Mode, a cycling extraction mode, or a cyclic mode), in which cycles of alternating pressure are applied, the clot is pulled towards or into the catheter under higher vacuum and released under lowered vacuum. In some embodiments, the pressure sensor constantly monitors the pressure in the catheter and controls the pump in accordance with a selected algorithm suited to the aspiration catheter being used and which is advantageously implemented by processor control to stay above a lower pressure limit (Plower) and below an upper limit (Pupper). This pressure cycle is repeated several times per second for an effective number of cycles. The cyclic strain on the clot causes it to break into fragments under the applied repetitive alternating stress. When a fragment of the clot is smaller than the ID of the catheter, the catheter is operated to aspirate the clot (and fragments thereof). When the fragments are small enough such that the catheter is not occluded (i.e., catheter pressure does not approach the lower pressure limit), the system can revert to the Static Mode during which the clot can be aspirated under a continuous negative pressure. In accordance with an embodiment of the invention, if the vessel is still occluded, the catheter is advanced to the face of the clot again which causes the pressure in the catheter to be reduced (i.e., approaching the lower pressure limit) indicating at least partial occlusion of the catheter, and the cyclic mode is resumed.

In some embodiments, when the device is activated, the pump aspirates blood out of the catheter and the pressure is monitored. If the pressure reaches the lower pressure limit of the desired range of aspiration pressures (referred to as "smart range"), the system can begin operating in the Smart Mode. For purposes herein, the term "smart range" refers to a selected and controlled lower and upper range of vacuum values (the terms "Plower" and "Pupper," respectively). Similarly, the term "Smart Mode" identifies an operational mode in which the pump is cycled to approach the lower and upper range without exceeding either, controlled by a selected algorithm suited to a particular catheter being used.

Specifically, the pump reverses direction and infuses blood into the catheter to raise the pressure. Similarly stated, the pump is operated at an infusion speed to raise the pressure within the catheter. When the rising pressure reaches the upper pressure limit of the smart range, the pump reverses and aspirates again. Similarly stated, the pump is operated at an aspiration speed to aspirate the contents from the vessel, which can cause reduction in the pressure within the catheter. In some embodiments, the infusion speed is lower than the aspiration speed. In some embodiments, the infusion speed is between 40% and 90% of the aspiration speed. In this manner, the flow rate that can exit the tip of the catheter can be lower flow rate that is being aspirated by the catheter. This can reduce the overall energy required to remove the thrombus and can also limit the likelihood that fragments of the thrombus will be urged downstream in the vessel (i.e., away from the catheter tip).

It has been found that higher frequencies break up a clot faster and more effectively than other approaches. The frequency of the cycling is dependent on how fast the pump can change the pressure. Parameters controlling frequency relate to software selectable parameters, hardware, and overall system considerations. For example, software parameters that affect frequency include predetermined selected upper and lower pressure limits (Pupper and Plower), speed and acceleration rates of the peristaltic pump rotor and sampling frequency of the pressure sensor.

Hardware parameters that can affect the frequency and/or pressures during cycling include compliance of tubing from sensor to catheter (stiffness and length), compliance of tubing from sensor to pump (stiffness and length), stiffness of pump tubing and volume per revolution of the pump rotor (tube ID and rotor diameter).

System parameters which also serve to determine cycle frequency include compliance of the catheter being used, compliance and characteristics of the particular clot being aspirated and amount of any air being present between the clot and the pump rotor. For example, some embodiments can produce pressure cycles for effective removal of different types of clot and/or for use with different catheter inner diameters. Positive and negative (vacuum) pressure cycle frequencies are adjustable for improved clot absorption/extraction (e.g., in the Smart Mode). The embodiments described herein provide methods and algorithms that are adjustable to different catheter sizes and styles.

Embodiments of algorithms of the invention customizable to be formulated for soft clots, organized clots, atherosclerotic clots, and dense/fibrous clots are described herein. For example, an accelerated clot removal setting can increase the intensity of the frequencies when tougher clots are encountered.

One parameter thought to have a particular impact on cyclic frequency, and thus performance of the inventive approach, is the amount of air in the system. Consequently, it is highly preferable that the system be fully primed before use and stay primed during subsequent operation. For example, a loose RHV (Rotating Hemostasis Valve) may allow air to enter the system under vacuum and adversely impact the effectiveness of the applied cyclic determining algorithm. In some embodiments, the pump can self-prime at the start of a procedure. According to this approach, once the user tracks the aspiration catheter, bring the tip near the location of the clot, the pump can be connected and primed. The connection between pump and catheter (or catheter RHV) can potentially introduce an air bubble into the tubing. But the distance from the bubble to the pump rotor is fixed and therefore the volume is known. The pump can be operated to aspirate this fixed volume (ideally including an added safety factor) to prime itself.

A thusly primed pump will operate at a relatively high cycling frequency. Any air introduced into the system will substantially reduce such frequency. The system can optionally and advantageously monitor the cycling frequency, and provide feedback to the user at any time reduced frequency is detected, indicating the likelihood that the system needs to be primed or if the connections (e.g., valves, connectors, etc.) need to be checked for leakage.

Since the system optionally uses a positive displacement pump, such as for example a peristaltic pump, the amount of blood pumped is proportional to the rotation(s) of the pump rotor and pressure. The pump can calculate and monitor the volume of blood pumped throughout the thrombotic extraction procedure. This volume can optionally be displayed to the user. The blood volume can be compared to a settable limit by the processor, which can optionally stop or slow the pump if this limit is reached. The user can then be alerted of this condition and may be presented with options for proceeding.

According to a particularly advantageous feature of the invention, the system can detect a plugged catheter by monitoring the pressure as the pump aspirates. If the pressure remains above the lower limit of the smart range, the catheter is not substantially occluded and the system is operating in the Static Mode (i.e., a continuous negative pressure is applied to aspirate fluids from the body lumen). In this condition, the user has not made enough contact with the clot to cause the catheter to experience reduced flow (and therefore reduced pressure that approaches or drops below Plower). If the pressure drops to the lower limit of the smart range and remains so, the catheter is determined as being plugged. The system can advantageously present this information to the user to give feedback on the presence of the clot.

In summary, it is believed that no one has heretofore combined positive and negative cycling pressure that can support longer and more flexible aspiration catheters with improved touchscreens to control the cycling patterns for all catheters on the market and being improved all of the time. By providing an optimized (as opposed to maximized) vacuum pressure/aspiration flow rate/thrombus removal force, the pressure system for the first time places all under interactive operator control.

Additionally, a system according to embodiment of the invention is advantageously provided in a form which is environmentally friendly. As envisioned, the housing is optionally and advantageously sourced from recycled materials and additionally, a clean take-apart process can optionally liberate and separate individual components for specialty material recycling and refurbishing. There is disclosed, inter alia, processes and methodologies regarding use of a recyclable pump constructed of sustainable materials for the purpose of aspirating thrombi, among other bodies, within blood vessels, particularly advantageously, those vessels within the human brain, and those associated with PV and/or STEMI, etc.

A user-friendly touch (or display) screen is advantageously provided, which allows for the operator/physician to be engaged with the status of the pump and choose to activate the pump in either a cycling Smart Mode (using APA) or a continuous aspiration Static mode. The touchscreen advantageously displays relevant conditions, such as for example, the battery level, status, operational mode, duration/time, pressure reading, and a graphical display of pressure, and allows the operator to select the appropriate catheter ID/length from a drop-down menu.

The terms "a" and "an," and "the" as used herein in the specification and in the claims, unless clearly indicated to the contrary, should be understood to mean "at least one" and are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups. The phrase "and/or," as used herein in the specification and in the claims, should be understood to mean either or both of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Any of the controllers described herein can include one or more processors including, for example, one or more of a single core or multi-core processor (e.g., AMD Phenom II X2, Intel Core Duo, AMD Phenom II X4, Intel Core i5, Intel Core I & Extreme Edition 980X, or Intel Xeon E7-2820). The term "processor" refers not only to integrated circuits referred to in the art as being included in a computer, but also refers to a controller, a microcontroller, a microcomputer, a programmable logic controller (PLC), an application specific integrated circuit, and other programmable circuits.

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

As used in this specification and the appended claims, the word "distal" refers to direction towards a work site, and the word "proximal" refers to a direction away from the work site. Thus, for example, the end of a device that is closest to the target treatment site would be the distal end of the device, and the end opposite the distal end (i.e., the end manipulated by the user) would be the proximal end of the device.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes include various spatial device positions and orientations. The combination of a body's position and orientation defines the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

FIG. 1A is a schematic illustration of a thrombectomy pump system 1000 according to an embodiment, and FIG. 1B is a schematic illustration of an aspiration controller 1220 (also referred to as "controller") of the thrombectomy pump system 1000 (also referred to as "system"). The thrombectomy pump system 1000 includes a housing 1100, a display 1122, a pump assembly 1210 and the aspiration controller 1220. The pump assembly 1210 is disposed within the housing 1100 and the display 1122 is coupled to the housing 1100 such that it is viewable to a user during a thrombectomy procedure. The thrombectomy pump system 1000 can be coupled to a catheter 1400 which can be inserted into a blood vessel of a patient such that the system 1000 can be used to macerate and remove an object, such as a blood clot, from the blood vessel.

The pump assembly 1210 includes a pump 1215. The pump 1215 can be, for example, a positive displacement pump, such as a peristaltic pump. The pump 1215 can be driven, for example, by a stepper motor. The pump 1215 can be actuated to provide positive and negative pressure to the catheter 1400 to force the object (e.g., clot) out of the blood vessel and within the catheter 1400 coupled to the pump system 1000 as described in more detail below. As described herein, the pump can be actuated to provide different modes of operation; the Smart Mode which uses an Adaptive Pulsative Algorithm (APA) to cycle the pressure within the catheter 1400 and a Static Mode in which the pump aspirates body fluids via the catheter 1400 at essentially constant vacuum. In the Smart Mode, the pump system operates as a "smart device" controlled by the APA unique to a selected aspiration catheter.

A pressure sensor (not shown in FIGS. 1A and 1B) can also be included and is used to measure the fluid pressure in the catheter 1400. The pressure measurement can provide feedback to the controller 1220, which can be used to determine which mode the pump 1210 should operate, i.e., if the pump 1215 should generate cyclic positive and negative pressure or should operate in the Static Mode (e.g., constant aspiration). As described herein, feedback from the pressure sensor can also be processed via the aspiration controller 1220 to determine conditions at the catheter tip (e.g., whether the catheter is plugged by a clot, whether a captured clot has been fragmented, whether there may be undesirable air in the system, and whether the catheter tip may be in contact with a side wall of the blood vessel). In response, the aspiration controller 1220 can implement any of the algorithms described herein.

Figure 1D:
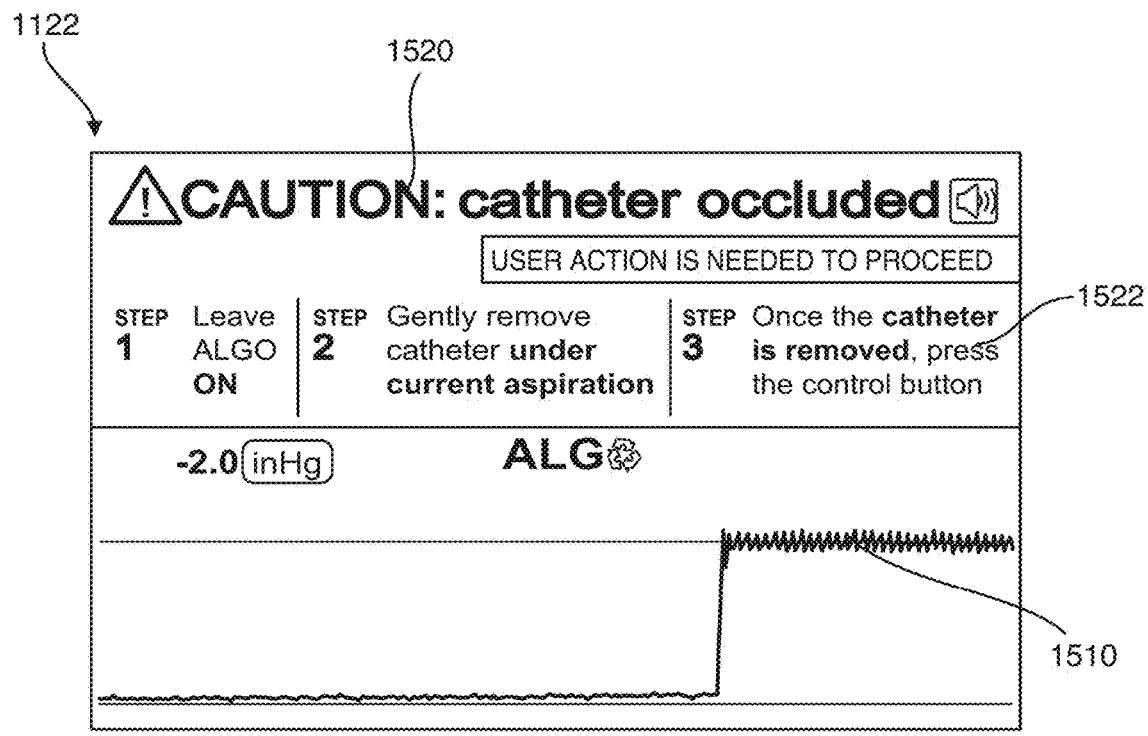

The display 1122 can be used by the user (e.g., surgeon) to actuate the system 1000, monitor pressures, receive notifications, and control the overall use and functions of the system 1000. The display 1122 can include a touchscreen that displays notifications associated with relevant conditions. Because the display 1122 is coupled to the housing 1100 and the system 1000 can be located in proximity to the patient, the notifications are close to the user and can be easily viewed during a procedure. The notifications can include, for example, a battery level notification 1502, an operational mode notification 1504, a duration/time notification 1506, a pressure reading 1509, and a graphical display of the catheter pressure 1510 (see e.g., FIG. 1C). In some embodiments, the display 1122 can also produce notifications with a status of the catheter or the system. For example, FIG. 1D shows an example graphical display of a status notification 1520 that identifies that the catheter is occluded and provides instructions for the user to withdraw the catheter tip from the vessel. In other embodiments, the display can produce any of the status notifications and instructions described herein.

The display 1122 can also allow the operator to provide input (e.g., in response to various prompts) to facilitate operation of the system 1000. For example, as shown in FIG. 1D, in some embodiments, a notification (see e.g., input prompt 1522) can prompt the user to actuate a button. In other embodiments, the system can prompt and receive user input to identify when the catheter tip has been moved, when fittings have been checked for air leakage, or to confirm completion of any other suitable action as described herein.

The display 1122 can also allow the user to select the appropriate catheter to be used for a specific procedure. One or more catheter parameter menus can be provided that provides a list of multiple different catheters that can be selected by the user. For example, the catheter parameter can be a list of catheter manufacturers (see the menu 1530 in FIG. 1E), a list of catheter diameters (see the menu 1532 in FIG. 1F), catheter lengths, catheter material construction, catheter tip design, etc. In some embodiments, the user can first select a specific procedure or attribute of the procedure. For example, in some embodiments, the user can select whether the thrombectomy to be performed is a neuro thrombectomy (i.e., addressing a thrombus in the intracranial vasculature) or a peripheral thrombectomy (i.e., addressing a thrombus in the peripheral vasculature). Other aspects of the procedure can also be input via the display. In this manner, the system 1000 can select an aspiration profile that is specific to the procedure or vasculature within which the procedure will be performed. Said another way, in some embodiments, the aspiration profile for a specific catheter (e.g., manufacturer, size, length) may be different depending on the procedure in which the catheter is being used. For example, in some embodiments, an aspiration profile for a catheter to be used for a neuro thrombectomy may be different from an aspiration profile for the same catheter to be used for a peripheral thrombectomy. The system 1000 and methods can allow for limitations on the energy delivered (e.g., via the aspiration flow rate, infusion flow rate, and pressure limits as discussed below) depending on the vasculature in which the procedure is being performed. In this manner, the system 1000 (and any of the systems described herein) and methods of use can reduce the likelihood of damage to the vasculature (e.g., perforation), while still effectively aspirating the thrombus.

Figure 1E:
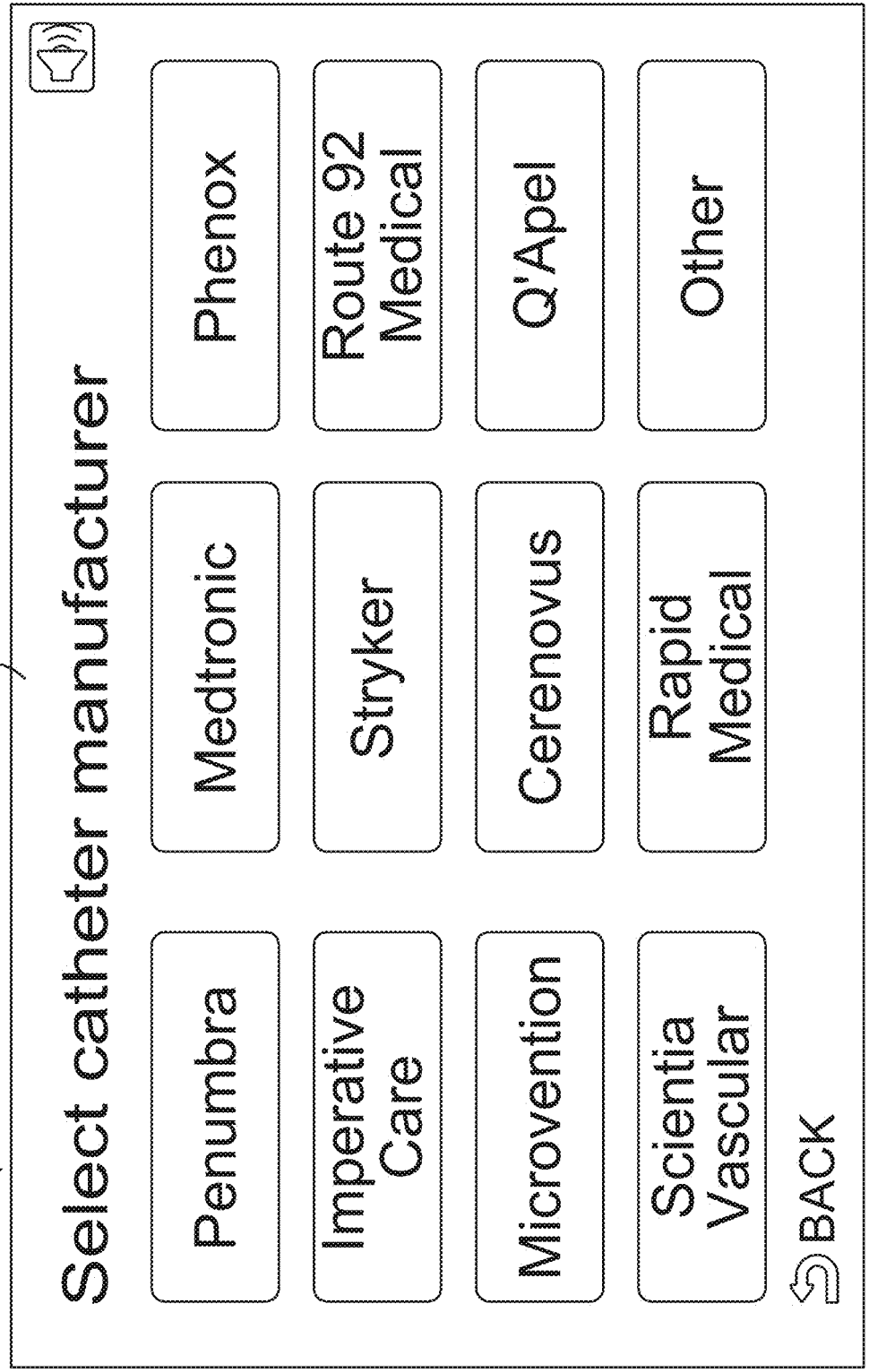

As shown in FIG. 1E, the user can select the catheter manufacturer from the display screen. The display 1122 can then provide a list of catheter diameters or diameter ranges (FIG. 1F). The user can then select the catheter size that corresponds to the catheter that is to be used for the procedure. In response to the user input, the system 1000 then loads an aspiration profile from a list of multiple preset aspiration profiles, each associated with a different catheter to be used during the procedure that corresponds to the selected catheter as described below. The aspiration profile can also optionally correspond to the procedure in which the catheter is to be used. The aspiration profile can be stored within controller 1220 (e.g., within a processor 1222 or a memory device 1223, as described below) and can be read, manipulated, and used by the controller 1220 (e.g., by the aspiration module 1226) to execute any of the methods described herein. The aspiration profile can include any suitable information to facilitate operation of the selected catheter during a thrombectomy procedure in an efficacious manner. For example, in some embodiments, the aspiration profile includes an upper pressure limit (Pupper), a lower pressure limit (Plower), an aspiration speed Aspeed (also referred to as "AS"), and an infusion speed (Ispeed) (also referred to as "IS" or push speed "PS") for each of the catheters within the list of catheters. These profile parameters are used by the APA in the Smart Mode. As described above, the system 1000 is configured to operate within a smart range, which is within the Pupper and Plower values. The Smart Mode operates cyclically to approach the Pupper and Plower range without exceeding either, controlled by a selected algorithm (APA) associated with the particular catheter being used.

During operation, the pump 1215 is cycled between the aspiration speed (i.e., when a pumping member within the pump is rotated in a first direction) and the infusion speed (i.e., when the pumping member is rotated in a second, opposite direction). When the pump 1215 is operated at the aspiration speed, fluid (e.g., blood, clot fragments, saline) is aspirated out of the body lumen via the catheter 1400. In this manner, the pump produces a vacuum (negative pressure) within the catheter (e.g., to suction out the fluid). In embodiments that employ a positive displacement pump, the flow rate of fluid aspirated is proportional to the aspiration speed. Thus, a higher aspiration speed produces a higher aspiration flow rate and can also produce a more rapid drop in pressure when the catheter tip is obstructed (e.g., by a clot). Similarly stated, operating at a higher aspiration speed exerts greater power (rate of energy) on the fluid, clot, vessel and surrounding materials. When the pump 1215 is operated at the infusion speed, fluid (e.g., blood, clot fragments, saline) is directed towards or introduced into the body lumen via the catheter 1400. In this manner, the pump produces a higher pressure within the catheter than when the pump is operating at the aspiration speed. In some embodiments, operating at the infusion speed can produce a positive pressure (but that is less than the localized blood pressure), while in other embodiments, operating at the infusion speed produces a lower vacuum pressure (i.e., a pressure that is still negative, but that has a lower magnitude than that produced when the pump is operating at the aspiration speed). In embodiments that employ a positive displacement pump, the flow rate of fluid towards or into the body lumen is proportional to the infusion speed. Thus, a higher infusion speed produces a higher infusion flow rate and can also produce a more rapid increase in pressure. Similarly stated, operating at a higher infusion speed exerts greater power (rate of energy) on the fluid, clot, vessel and surrounding materials.

As shown in FIG. 1B, the controller 1220 includes one or more processors 1222, one or more memory devices 1223, an input module 1224, an output module 1225 and an aspiration module 1226. The input module 1224, the output module 1225 and the aspiration module 1226 can each be hardware and/or software modules that are implemented in at least one of the memory devices 1223 or processors 1222 of the aspiration controller 1220. FIG. 1B illustrates the input module 1224, output module 1225 and aspiration module 1226 as being separate components outside of the processors 1222 and memory devices 1223, but can alternatively be included within a processor 1222 or memory device 1223. Moreover, although the controller and associated methods are described herein as having certain signals being received or activities being performed by one module, in other embodiments, signals can be received, manipulated and/or used by any of the modules described herein to perform any of the methods described herein. Although the controller 1220 (and all of the components therein) is shown as being coupled to the housing 1100, in other embodiments, the all or portions of the controller 1220 (and any of the controllers described herein) can be spaced apart from the housing 1100. For example, in some embodiments, the controller 1220 can include a network module (not shown) configured to exchange information between the system 1000 and a remote computing device (e.g., via wireless communication).

As described above, a user (e.g., surgeon) can select one or more catheter parameters such as the catheter manufacturer and catheter size to be used in the procedure. The input module 1224 is configured to receive from the user this input associated with the catheter parameter(s) associated with the selected catheter. The input can be received, for example, via input prompts on the display screen 1122 (see, e.g., FIGS. 1E and 1F). The aspiration module 1226 is configured to select an aspiration profile associated with the catheter parameter from a list of a plurality of preset aspiration profiles each associated with a different catheter. The aspiration profile can be in any suitable format to facilitate operation of the system 1000. For example, in some embodiments, the aspiration profile for each catheter can be one or more data tables providing parameters specific to the selected catheter and/or the selected procedure. In other embodiments, the aspiration profile for each catheter can be one or more calibration curves (or equations) that are manipulated by the controller 1220 (and any of the components therein) to perform the methods described herein. As described above, the aspiration profile includes an upper pressure limit Pupper, a lower pressure limit Plower, an aspiration speed Aspeed, and an infusion speed Ispeed. The aspiration module 1226 is configured to send a first set of signals based on the aspiration profile to the thrombectomy pump assembly 1210 to operate the thrombectomy pump assembly 1210 in a first mode. For example, the first mode can include operating the pump 1210 in the Smart Mode to provide cyclic pressures, or in the Static Mode to provide constant aspiration pressure. In some embodiments, the aspiration module 1226 includes one or more motor drivers and the set of signals sent to the thrombectomy pump assembly includes a set of voltage (or voltage pulses) to operate the pump 1215 as desired.

During the procedure, the aspiration module 1226 can receive a pressure signal associated with the catheter pressure from the sensor (e.g., pressure sensor) (not shown in FIGS. 1A and 1B). Based on the pressure signal received, the aspiration module 1226 is configured to send a second set of signals based on the aspiration profile to the thrombectomy pump assembly to operate the thrombectomy pump assembly in a second mode (e.g., Smart Mode or Static Mode). In some embodiments, the first mode may be the Static Mode and the second Mode may be the Smart Mode. In the second mode the pump is cycled between the aspiration speed Aspeed and the Infusion speed Ispeed such that the catheter pressure cycles between the upper pressure limit Pupper and the lower pressure limit Plower of the aspiration profile being used. This can be referred to as operating within the smart range as described above.

Figure 2A:
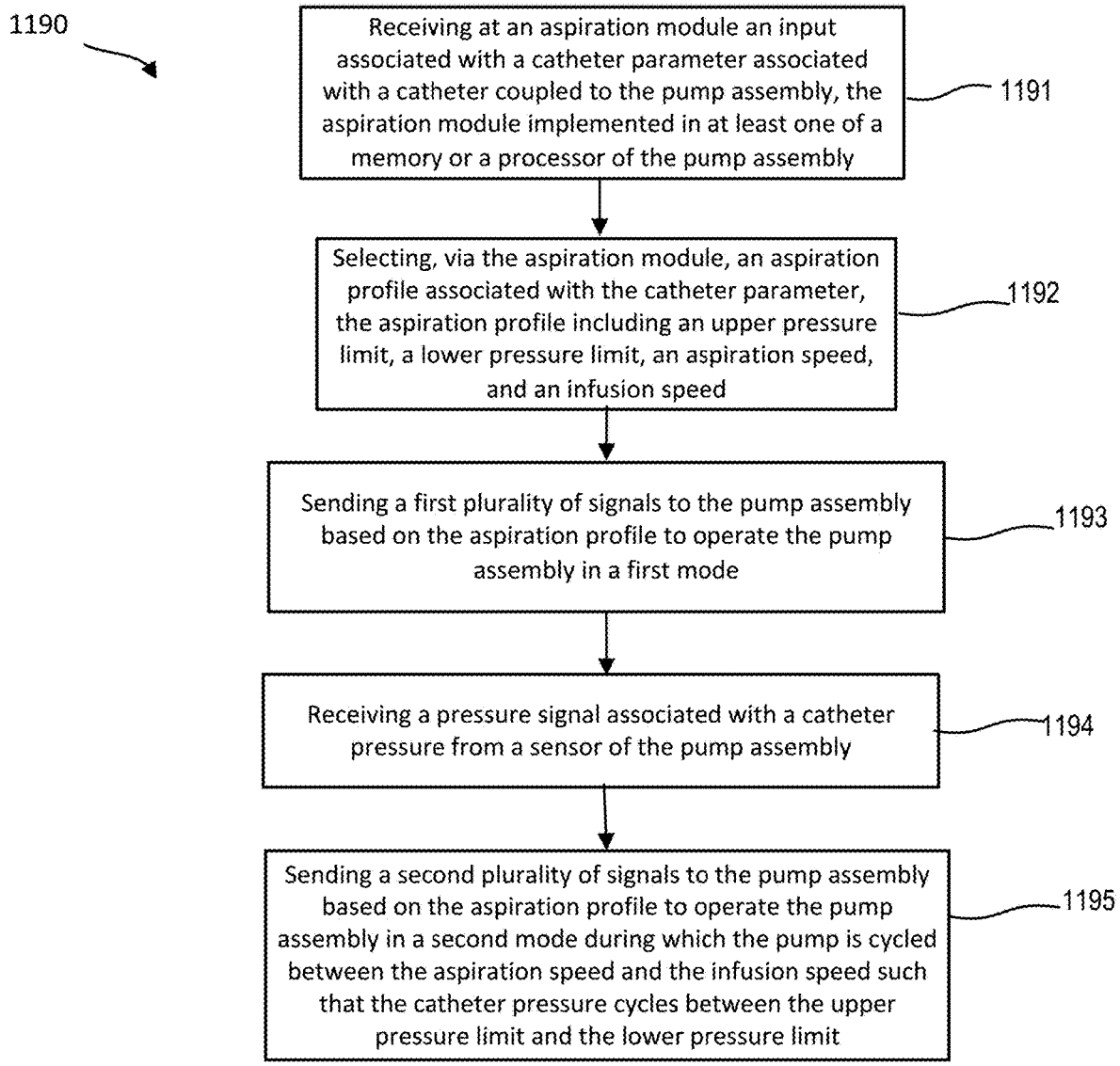
FIG. 2A is a flowchart illustrating a method of using a thrombectomy pump system to remove a thrombus from a body vessel.

FIG. 2A is a flowchart illustrating an example method of using a thrombectomy pump system such as system 1000 to aspirate a thrombus from a body via a catheter coupled to a pump assembly (e.g., pump 1210) that includes a pump (e.g., pump 1215). A method 1190 includes at 1191, receiving at an aspiration module (e.g., aspiration module 1226) of the pump assembly an input associated with a catheter parameter associated with the catheter coupled to the pump assembly. For example, a user input module can receive a user input associated with the catheter from a list of selectable catheters. As described herein, the user can select one or more catheter parameters on a display screen of the thrombectomy pump system. The catheter parameter can include at least one of a manufacturer of the catheter, an inner diameter of the catheter, a compliance of the catheter, a tip configuration of the catheter, or a length of the catheter.

The aspiration module can be implemented in at least one of a memory or a processor coupled to the pump assembly. At 1192, an aspiration profile associated with the catheter parameter is selected via the aspiration module from a list of a plurality of preset aspiration profiles. Each of preset aspiration profiles is associated with a different catheter (and optionally, a different procedure or region of vasculature in which the catheter is being used). The aspiration profile includes an upper pressure limit, a lower pressure limit, an aspiration speed, and an infusion speed. In some embodiments, the aspiration speed is different than the infusion speed. In some embodiments, the infusion speed is between 40% and 90% of the aspiration speed. In some embodiments, the upper pressure limit is less than a blood pressure within the blood vessel.

At 1193, a first plurality of signals is sent to actuate the pump based on the aspiration profile to operate the pump in a first mode. In some embodiments, the first mode includes operating the pump at the aspiration speed. At this operating condition, fluid is being aspirated out of the body lumen at a substantially constant flow rate that is proportional to the aspiration speed. At 1194, a pressure signal associated with a catheter pressure from a sensor of the pump assembly is received as the aspiration module. At 1195, on a condition that the catheter pressure is below a pressure threshold a second plurality of signals to actuate the pump based on the aspiration profile to operate the pump in a second mode is sent to the pump via the aspiration module. The catheter pressure can drop, for example, when the tip of the catheter becomes obstructed or partially obstructed, thereby increasing the pressure drop of fluid flowing into the catheter. Accordingly, when the catheter pressure drops below the pressure threshold, the catheter tip may be in contact with (or proximity to) a clot. In the second mode the pump is cycled between the aspiration speed and the infusion speed such that the catheter pressure cycles between the upper pressure limit and the lower pressure limit. In this manner, the system can cycle the pressure between predetermined pressure limits and at specific pump speeds tailored to be an effective amount for macerating, disrupting and removing the thrombus. By cycling the pressure according to the aspiration profile, system can limit potential damage or undesired outcomes that can be associated with the use of excessive energy or cycling, such as damage to the vessel wall, undesired collapsing of the catheter wall, and undesired movement of the thrombus downstream (i.e., away from the catheter tip).

In some embodiments, after the sending the second plurality of signals to actuate the pump to operate in a second mode, a second pressure signal associated with a second catheter pressure is received at the aspiration module from the sensor of the pump assembly. If the second catheter pressure is below a preset pressure limitation indicating a plugged state, a notification to withdraw the catheter from the blood vessel is sent (e.g., to the display or a speaker). For example, as shown in FIG. 1D, when the catheter pressure drops below the preset limitation, the notification 1522 can be sent to the display (e.g., the display 1122) to prompt the surgeon to withdraw the catheter (with the thrombus occluded therein).

In some embodiments, the pump assembly includes a pump housing coupled to a housing of the thrombectomy pump system, and the method further includes receiving at the aspiration module an indication from a switch coupled to the pump housing that the pump housing has been decoupled from the housing of the thrombectomy pump system. Upon receipt of the indication, the pump assembly is automatically shut off. In some embodiments, after sending the second plurality of signals to actuate the pump to operate the pump in the second mode, a second pressure signal associated with a second catheter pressure from the sensor of the pump assembly is received at the aspiration module. In response, a third plurality of signals to actuate the pump to operate the pump in a third mode based on the selected aspiration profile is sent and the third mode includes operating the pump at the aspiration speed.

Figure 2B:
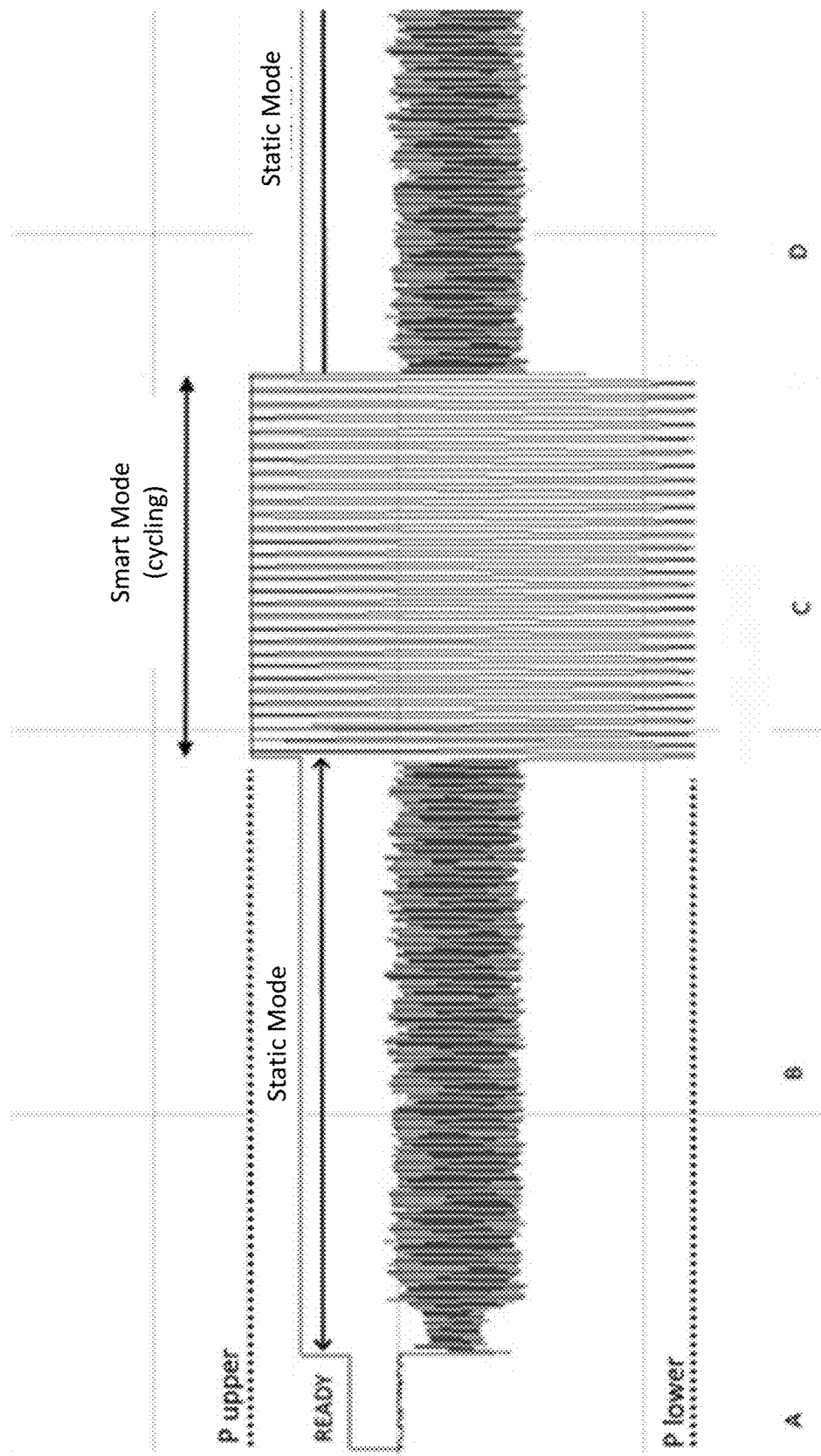
FIG. 2B is a plot showing catheter pressure as a function of time for example operation cycle for a thrombectomy pump system according to an embodiment.

FIG. 2B provides an example of an operation cycle for a thrombectomy procedure using a thrombectomy pump system as described herein, such as system 1000, according to any of the methods described herein (e.g., the method 1190). FIG. 2B is a plot of the catheter pressure measured during a bench test extraction procedure where a clot was successfully aspirated via the catheter with minimal issues. FIG. 2B shows a plot of the catheter pressure (Y-axis) as a function of time (X-axis) over a series of different operational modes, labeled as regions A, B, C, and D. As shown in region A, initially, the pump is a state of readiness where it is coupled to the catheter, but is not yet pumping. In this state, the catheter pressure is substantially constant and is based on the blood pressure. After the pump is actuated, it is operated in the Static Mode (region B) during which it aspirates fluid from the body lumen via the catheter. Accordingly, in the Static Mode, a negative pressure is generated. Because the catheter tip is not in proximity to a clot, there is no substantial pressure drop caused by an occlusion of the catheter tip. The measured catheter pressure is therefore above the Plower and the system will not indicate any partial or full occlusion of the catheter. In some instance the region of operation can be characterized as a "free flow" condition, during which there is no significant obstruction and the pump is operating at a substantially constant aspiration speed (according to the aspiration profile).

Figure 2C:
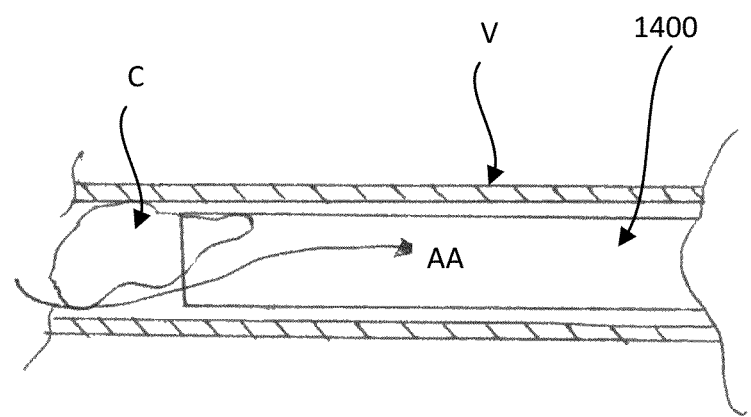
FIGS. 2C-2F are schematic illustrations of a catheter extracting a clot from a body vessel using a method according to an embodiment.
Figure 2D:
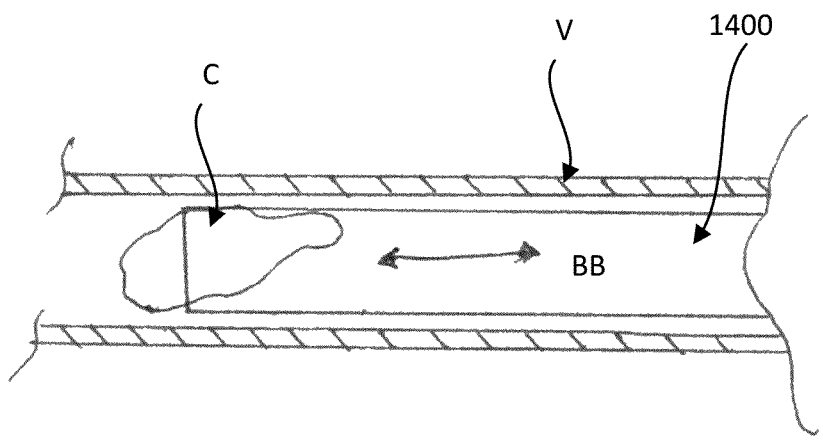
Figure 2E:
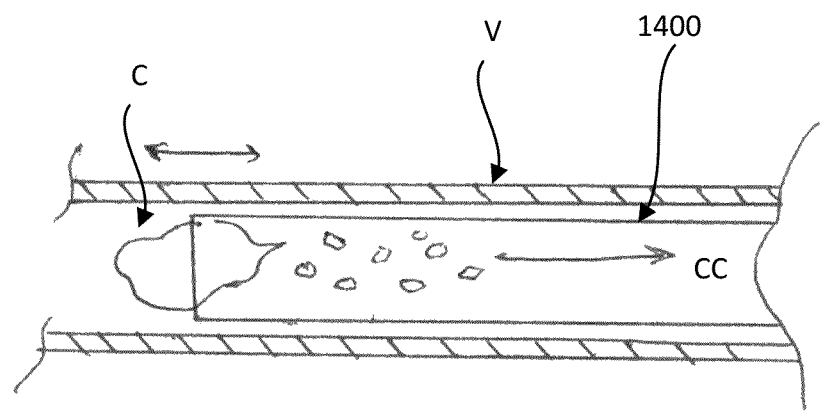
Figure 2F:
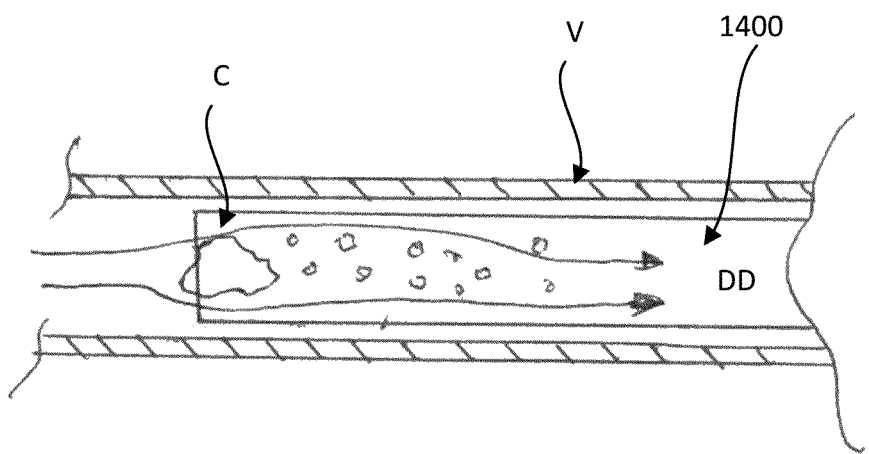

When the catheter makes contact with the clot, a partial or full occlusion occurs at the catheter tip and the catheter pressure drops. FIG. 2C shows schematic illustration of the catheter 1400 within a vessel V showing a partial occlusion caused by the clot C. Because of the obstruction at the catheter tip, the flow of fluid being aspirated (shown by the arrow AA) will produce a pressure drop. Feedback from the pressure sensor causes the system to operate the pump in the Smart Mode, which activates the APA. As shown in region C of FIG. 2B, in the Smart Mode the pump is cycled between the aspiration speed and the infusion speed such that the catheter pressure cycles between the upper pressure limit and the lower pressure limit. This is shown schematically in FIG. 2D by the arrow BB. As the pump is operated at the aspiration speed, Plower is the pressure value at which the controller will cause the pump to operate at the infusion speed (i.e., to change directions). By infusing fluid back towards the catheter tip, the clot will be pushed distally to prevent corking. In this manner, the clot can be macerated during aspiration, which can prevent the clot from becoming lodged as a "solid" piece and obstructing (or corking) the catheter. After the pump is operating at the infusion speed (i.e., pushing fluid towards the catheter tip), the catheter pressure increases. The Pupper is the pressure value at which the controller will cause the pump to change direction and start aspiration again. The maceration of the clot is shown schematically in FIGS. 2E and 2F, which show fragments of the clot being aspirated (arrows CC in FIG. 2E and DD in FIG. 2F). After the clot is aspirated through the catheter, the pump will return to operation in the Static Mode (region D).

The aspiration profile is configured for each catheter so that when the pump is operating in Smart Mode (i.e., pressure cycling), during the infusion portion the cycle the infusion speed such that the portion of the clot within the catheter is slightly dislodged and moved distally, while keeping it within a range where it will be suctioned back proximally during the aspiration portion of the cycle. Thus, the aspiration profile is specific for each catheter to limit the likelihood of producing embolization in new territories (ENTs). Similarly stated, by limiting the energy applied to the body lumen during the infusion portion of the cycle, the clot can still be effectively macerated, disrupted and removed, while also limiting undesired outcomes that can be associated with the use of excessive pushing force such as damage to the vessel wall or ENTs. The selection of the aspiration speed and infusion speed and the Pupper and Plower (i.e., the aspiration profile) is specific for a given catheter and can also be adjusted for the consistency of the clot being removed.

Figure 2G:
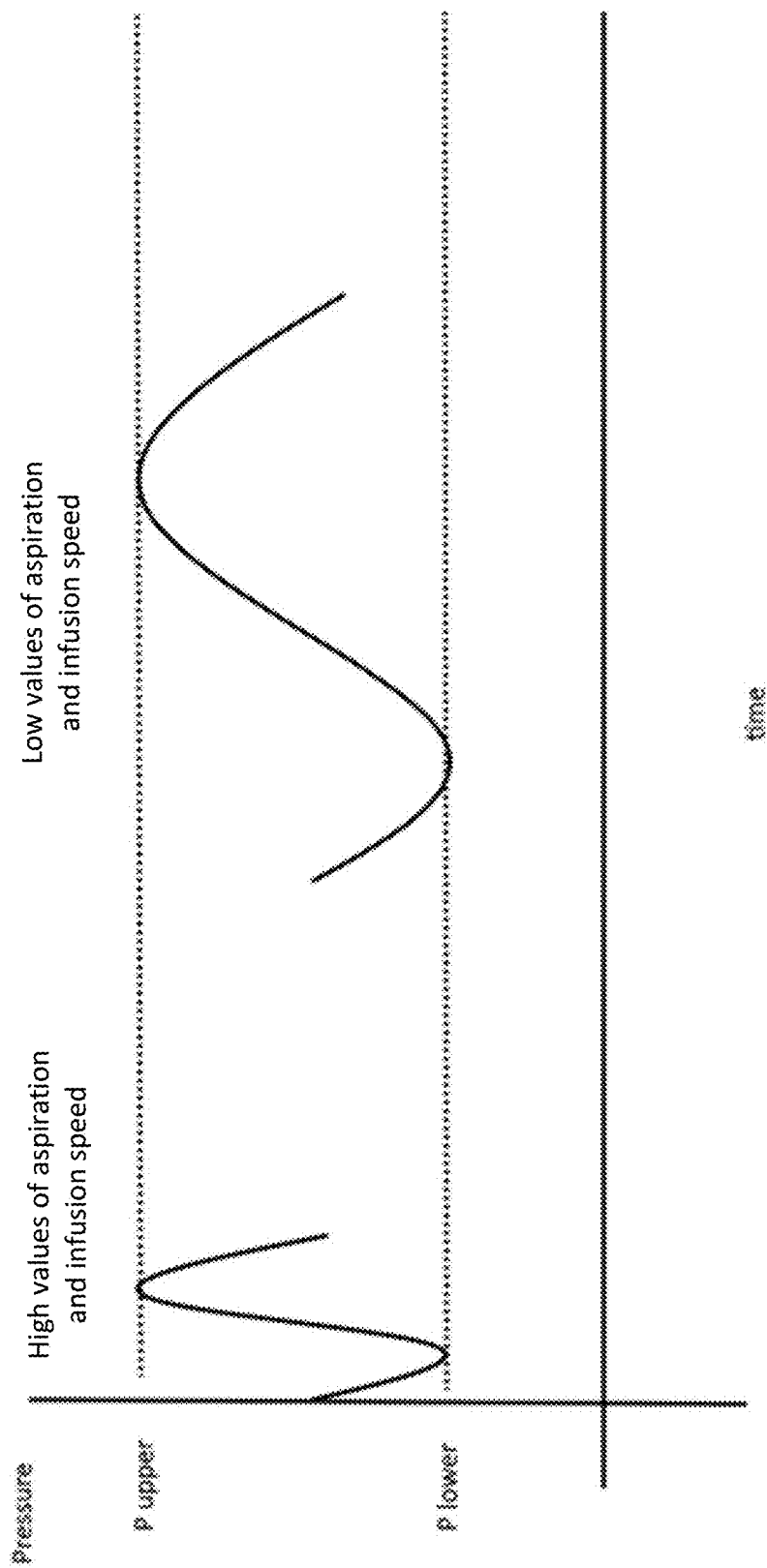

Although the pressure waveform that appears on the display (e.g., FIG. 1C) might, in some instances, be a consistent or fixed frequency waveform, in other instances, the pressure wave form can be dependent on the value of the parameters of the aspiration profile and the consistency of the clot. For example, FIG. 2G is a graphical representation of the catheter pressure as a function of time for different values of the aspiration speed and infusion speed. As shown, in situations where the aspiration and infusion speeds are high, the aspiration and infusion flow rates are high, thus producing a higher frequency cycle between the Pupper and Plower. Conversely, in situations where the aspiration and infusion speeds are low, the aspiration and infusion flow rates are low, thus producing a lower frequency cycle between the Pupper and Plower. In some embodiments, the aspiration profile is such that the infusion speed is lower than the aspiration speed. This causes the slope of the pressure wave as the pressure increases (during infusion) to be lower than that when the pressure decreases (during aspiration). In this manner, the force with which the clot is pushed out of the catheter during cycling can be controlled to limit the likelihood of producing ENTs. In some embodiments, the infusion speed is between 40% and 90% of the aspiration speed. In some embodiments, the infusion speed is between 60% and 80% of the aspiration speed.

Figure 2H:
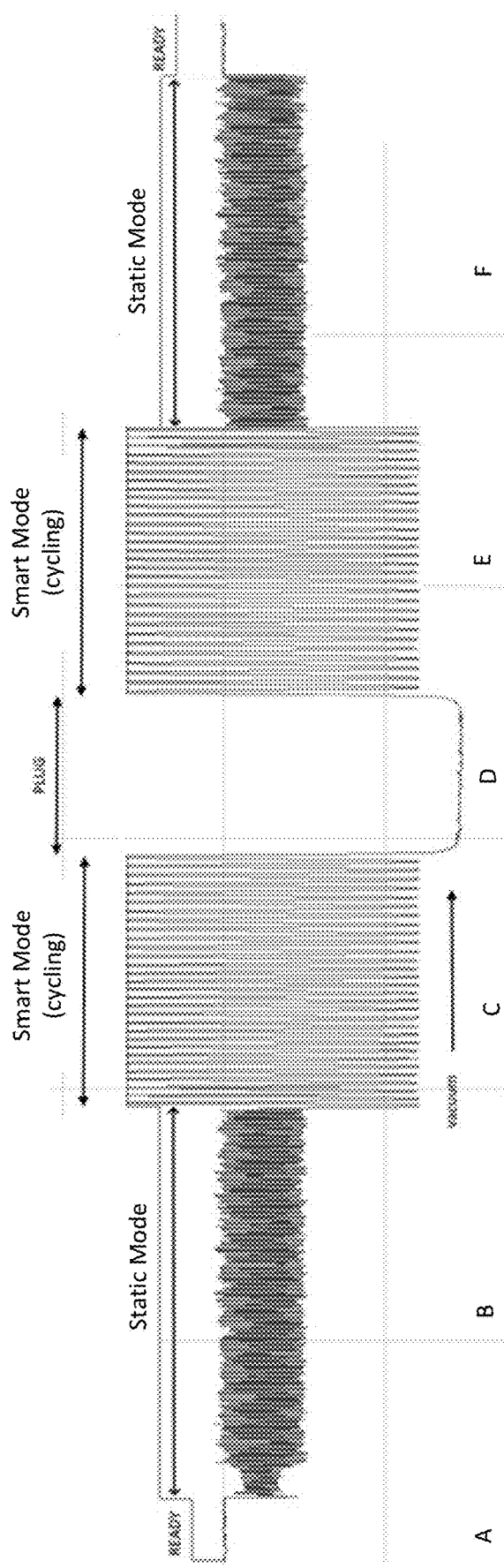
Figure 21:
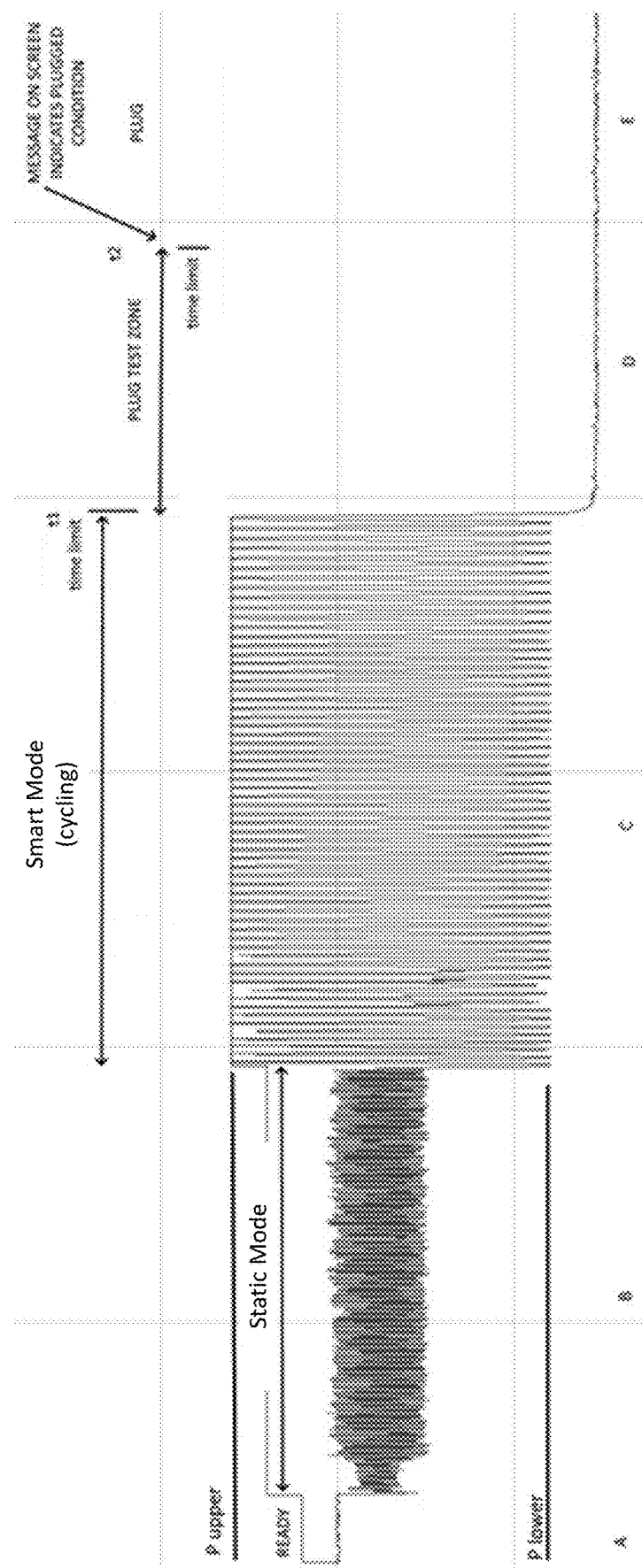
FIG. 21A is a cross-sectional view of the thrombectomy pump system of FIG. 7 illustrating the connection between the cover assembly and the housing assembly.
FIG. 21B is an enlarged cross-sectional view of a portion of the thrombectomy pump system of FIG. 21A illustrating the connection between the cover assembly and the housing assembly.

FIG. 2H provides an example of an operation cycle for a thrombectomy procedure using a thrombectomy pump system as described herein, such as system 1000, according to any of the methods described herein (e.g., the method 1190). FIG. 2H is a plot of the catheter pressure measured during a bench test extraction procedure over a series of different operational modes, labeled as regions A, B, C, D, E and F. Region A is a state of readiness where the pump is coupled to the catheter, but is not yet pumping. After the pump is actuated, it is operated in the Static Mode (region B) during which it aspirates fluid from the body lumen via the catheter. Accordingly, in the Static Mode, a negative pressure is generated. When the catheter makes contact with the clot, a partial or full occlusion occurs at the catheter tip and the catheter pressure drops. Feedback from the pressure sensor causes the system to operate the pump in the Smart Mode, which activates the APA. As shown in region C, in the Smart Mode the pump is cycled between the aspiration speed and the infusion speed such that the catheter pressure cycles between the upper pressure limit and the lower pressure limit, as described herein.

After cycling during a predetermined time period, if the system is not able to aspirate the clot, the controller causes the pump to operate in a plugged state, as shown in region D. In the plugged state, the clot is at least partially retained within the catheter and the pump operates continuously at an aspiration speed. Accordingly, because of the obstruction, the catheter pressure drops towards a vacuum. If, however, the occlusion can be removed at least partially, the controller causes the pump to again operate in the Smart Mode (cycling) as shown in region E. This process can be repeated until specified time limits are exceeded or the user stops the process. After the clot is aspirated through the catheter, the pump will return to operation in the Static Mode (region F).

FIG. 2I provides an example of an operation cycle for a thrombectomy procedure when the predetermined time period is exceeding while the pump is operating in the plugged state. As described above, the system will enter the plugged state after a predetermined time of operating in the Smart Mode (cycling), which is indicated by the time t1 in FIG. 2I. During the plugged state, the pump aspirates constantly, which produces a negative pressure creating a vacuum (see region D in FIG. 2I). The which is shown by the system entering the plugged state at time t1. During the plugged state the pump operates to apply a constant negative pressure on the clot, which may extract the clot. This state can be switched back to the EXTRACT state if the catheter pressure increases, as shown in FIG. 2H. After a predetermined time (indicated by the time t2 in FIG. 2I), if the catheter pressure does not increase, the algorithm stops trying to remove the clot, and simply maintains the negative pressure. In some embodiments, the system sends a notification (see, e.g., FIG. 1H) to withdraw the catheter from the blood vessel after the time period t2 has elapsed. The user is prompted that the catheter be removed carefully to keep the clot from separating from the catheter. The system will remain in Static Mode until the user deactivates the pump.

Figure 3A:
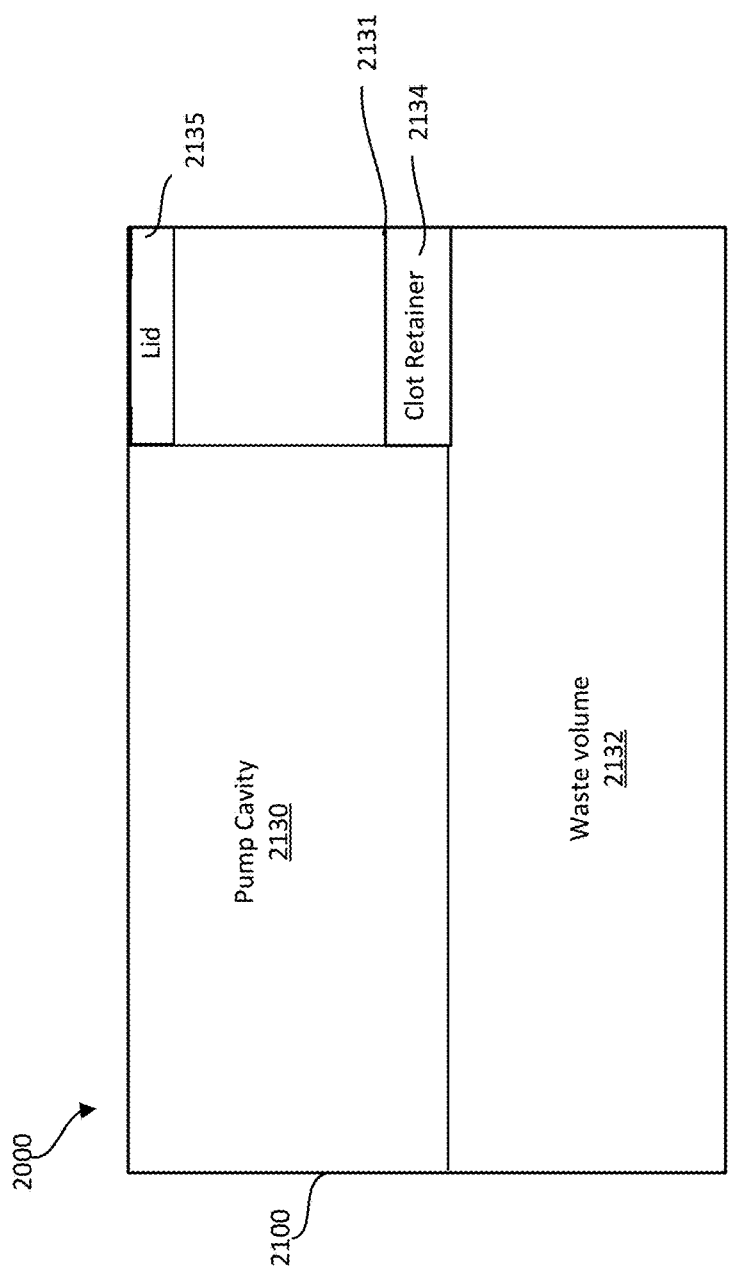
FIG. 3A is schematic illustration of a thrombectomy pump system, according to an embodiment.
Figure 3C:
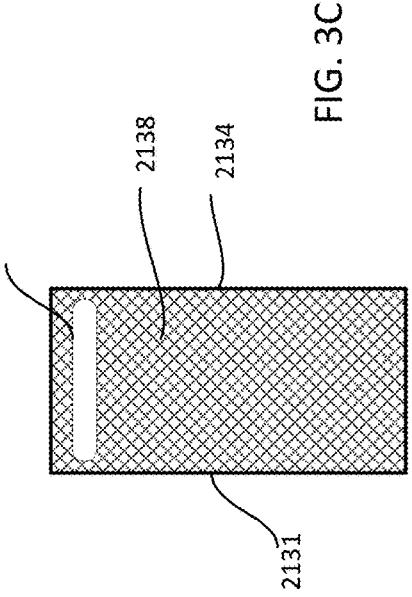
FIG. 3C is a schematic illustration of a top view of a clot retainer of the thrombectomy pump system of FIG. 3A.
Figure 3B:
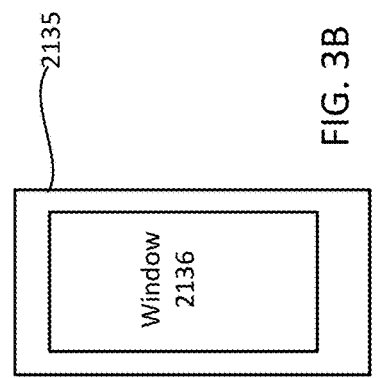
FIG. 3B is a schematic illustration of a top view of a lid of the thrombectomy pump system of FIG. 3A.

FIGS. 3A-3C are schematic illustrations of a thrombectomy pump system 2000 (also referred to as "system") according to another embodiment. The system 2000 can include the same or similar features and functions as described above for system 1000 and/or as described for other thrombectomy pump systems described herein. The system 2000 can be coupled to a catheter and used in a procedure to remove an object from a blood vessel, such as a blood clot. FIG. 3A is a side view of the system 2000, FIG. 3B is a top view of a lid 2135, and FIG. 3C is a top view of a clot retainer 2134. The thrombectomy pump system 2000 includes a housing 2100 that includes a pump cavity 2130 and a waste volume 2132. In some embodiments, the waste volume 2132 surrounds at least a portion of the pump cavity 2130 as described below and shown with reference to the thrombectomy pump system 4000. In some embodiments, the waste volume 2132 has a volume of up to about 1000 cubic centimeters. In some embodiments, the waste volume 2132 has a volume between 500 and 1000 cubic centimeters.

The pump cavity 2130 is configured to receive therein a pump assembly (not shown in FIGS. 3A-3C), such as the pump assembly 1210. The pump assembly can include a pump as described herein to provide aspiration and/or infusion pressures to remove an object from the blood vessel, through the catheter coupled to the housing 2100, through the pump within the pump cavity 2130 and into the waste volume 2132. A clot retainer 2134 is removably coupled to the housing 2100 within the waste volume 2132 and has a surface 2131 having a first portion defining multiple openings 2138 and a second portion defining a bypass opening 2137 as shown in FIG. 3C. A lid 2135 is removably coupled to the housing 2100 to cover the clot retainer 2134. The lid 2135 includes a transparent portion 2136 to allow viewing of the clot retainer 2134 through the lid 2135. In this manner, the system facilitates rapid inspection of the clots and fluids aspirated from the blood vessel.

The clot retainer 2134 is used to filter blood and other material drawn into the system 2000 and into the waste volume 2132. The multiple openings 2138 of the clot retainer 2134 are sized to allow liquid to flow through the surface 2131 and into the waste volume 2132 but prevent large objects (larger than the size of the openings 2138) from passing through the openings 2138. For example, during a procedure to remove a blood clot from a blood vessel, the clot can be collected on the clot retainer 2134, while blood and other liquid can pass through the openings 2138 of the clot retainer 2134 and into the waste volume 2132. The transparent portion 2136 of the lid 2135 can be used to view into the waste volume 2132 to observe the contents introduced therein and captured on the clot retainer 2134. In some embodiments, the portion of the housing 2100 defining the waste volume 2132 can be formed with a transparent material or include a portion that is transparent to allow a user to view into the waste volume 2132 and the contents therein.

The bypass opening 2137 allows for overflow of liquid to pass through the clot retainer 2134 and into the waste volume 2132. For example, if an excess volume of liquid is introduced onto the clot retainer 2134, to prevent the liquid from pooling up on the clot retainer 2134, the bypass opening 2137 provides for the excess liquid to pass through the clot retainer 2134 quickly to prevent overflow and a backup of liquid passing back into the pump cavity 2130. In some embodiments, the clot retainer 2134 is coupled to the housing 2100 at an angle relative to a base surface (not labeled in FIG. 3A) of the housing 2100 and/or the clot retainer 2134 itself is constructed with the surface 2131 on an angle, such that the bypass opening 2137 is positioned further from (i.e., higher than) the base surface of the housing 2100 than the multiple openings 2138. Said another way, the first portion of the top surface 2138 of the clot retainer 2134 is disposed at a first distance from the base surface of the housing 2100 and the second portion of the surface 2131 of the clot retainer 2134 is disposed at a second distance from the base surface of the housing 2100, with the second distance being greater than the first distance. In some embodiments, the waste volume 2132 has a height defined between the lid 2135 and the base surface of the housing 2100, and the surface 2131 of the clot retainer 2134 is positioned relative to the lid 2135 at a distance equal to between 5% and 25% of the height of the waste volume. Said another way, the surface 2131 upon which the extracted clot will be retained is no more than a quarter of the way below the lid 2135. This arrangement limits the likelihood that the blood level within the waste volume 2132 will extend above the surface and obstruct the user's view of any clot retained on the surface 2131.

In some embodiments, the housing 2100 includes a mounting shoulder (not shown) within the waste volume 2132, on which the clot retainer 2134 is supported. In some embodiments, the mounting shoulder positions the clot retainer 2134 such that at least the second portion of the surface 2131 of the clot retainer 2134 is at an angle relative to the base surface of the housing 2100. In some embodiments, the housing 2100 and/or other portions of the system 2000 (e.g., a pump assembly) defines an outlet port in a wall of the housing 2100 between the pump cavity 2130 and the waste volume 2132 at a third distance from the base surface, where the third distance is greater than the first distance between the first portion of the clot retainer 2134 and the base surface of the housing 2100, and the outlet port is in fluid communication with the waste volume 2132. In some embodiments, a centerline of the outlet port in the housing 2100 extends parallel with the surface 2131 of the clot retainer 2134. In some embodiments, at least one light (not shown in FIGS. 3A-3C) is provided to illuminate the waste volume 2132.

Although not shown in FIGS. 3A-3C, the system 2000 can also include a pump assembly and pump (each not shown), disposed within the pump cavity 2130. The pump assembly and pump can be the same as or similar to any of the pump assemblies and pumps described herein. For example, the pump can be actuated to provide different modes of operation; the Smart Mode which uses an Adaptive Pulsative Algorithm (APA) and a Static Mode in which the pump aspirates at essentially constant vacuum. In the Smart Mode, the pump system operates as a "smart device" controlled by the APA unique to a selected aspiration catheter (and optionally, the procedure in which the catheter is being used).

An aspiration tube (not shown in FIGS. 3A-3C) can extend from the pump within the pump cavity 2130 and within the outlet port of the housing 2100 such that the aspiration tube is in fluid communication with the waste volume 2132.

In some embodiments, the clot retainer 2134 includes a tab (not shown) extending upwardly from the top surface 2131 of the clot retainer 2134. The tab includes an alignment feature configured to matingly engage the lid 2135. For example, the lid 2135 can include a mating coupling feature to couple to the tab. The lid 2135 can also include an attachment mechanism to removably couple the lid 2135 to the housing 2100. For example, the attachment mechanism can include one or more magnets.

Figure 4:
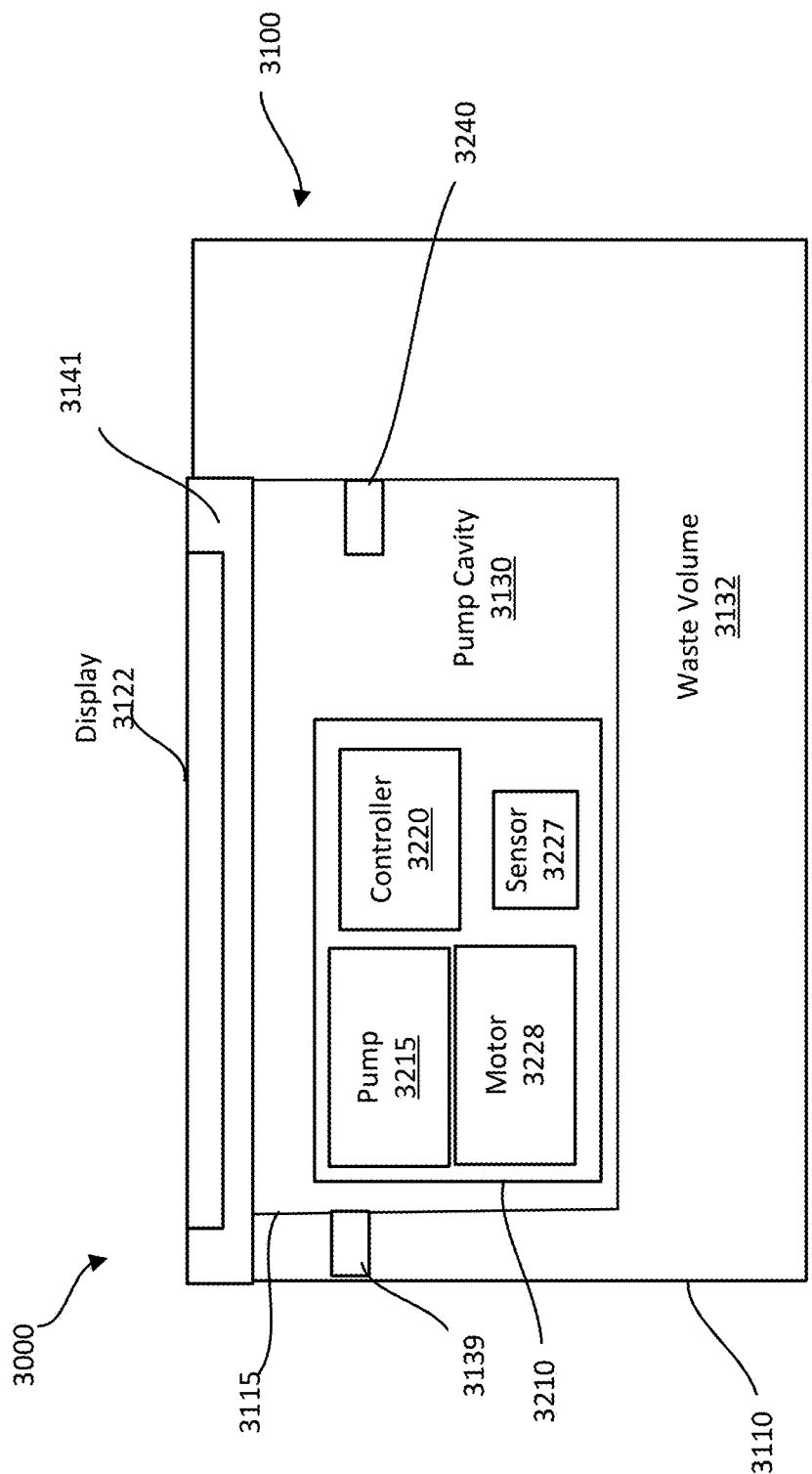
FIG. 4 is a schematic illustration of a thrombectomy pump system according to an embodiment.

FIG. 4 is a schematic illustration of a thrombectomy pump system 3000 (also referred to as "system") according to another embodiment. The system 3000 can include the same or similar features and functions as described above for systems 1000 and 2000 and/or as described for other thrombectomy pump systems described herein. The system 3000 can be coupled to a catheter and used in a procedure to remove an object from a blood vessel, such as a blood clot. The thrombectomy pump system 3000 includes a housing 3100 that includes a first housing portion 3115 that defines a pump cavity 3130 and a second housing portion 3110 that defines a waste volume 3132. The waste volume 3132 at least partially surrounds the first housing portion 3115 and pump cavity 3130. In some embodiments, the waste volume 3132 has a volume of up to about 1000 cubic centimeters. In some embodiments, the waste volume 3132 has a volume between 500 and 1000 cubic centimeters. A pump assembly 3210 is disposed within the pump cavity 3130 and includes an inlet port 3139 configured to be coupled to a catheter (not shown) and an outlet port 3140 that is in fluid communication with the waste volume 3132. The pump assembly 3210 includes a pump 3215, a motor 3228 to drive the pump 3215, a sensor 3227, and a controller 3220. A cover 3141 is coupled to the first housing portion 3115 and encloses the pump cavity 3130 and a display screen 3122 is coupled to the cover 3141 and is operably coupled to the controller 3220.

The pump 3215 can be a positive displacement pump such as a peristaltic pump, a piston pump, or a vane pump, and can be driven by the motor 3228. The motor 3228 can be, for example, a stepper motor. The pump 3215 can be actuated to provide positive and negative pressure to force the object (e.g., clot) out of the blood vessel and within the catheter coupled to the pump system 3000 as described herein. As described above, the pump 3215 can be actuated to provide different modes of operation; the Smart Mode which uses an Adaptive Pulsative Algorithm (APA) and a Static Mode in which the pump aspirates at essentially constant vacuum. In the Smart Mode, the pump system operates as a "smart device" controlled by the APA unique to a selected aspiration catheter.

The sensor 3227 can be any suitable pressure sensor that can measure the fluid pressure in the catheter coupled to the housing 3100. The pressure measurement can provide feedback to the controller 3220 which can be used to determine the appropriate mode in which the pump should operate, i.e., if the pump should operate in the Smart Mode and generate cyclic positive and negative pressures or operate in the Static Mode and generate constant aspiration pressure.

The display 3122 can be used by the user (e.g., surgeon) to actuate the system 3000, monitor pressures, receive notifications, and control the overall use and functions of the system 3000 as described for system 1000. The display 3122 can include a touchscreen that displays notifications associated with relevant conditions. Because the display 3122 is coupled to the housing 3100 and the system 3000 can be located in proximity to the patient, the notifications are close to the user and can be easily viewed during a procedure. The notifications can include, for example, the battery level, status, operational mode, duration/time, pressure reading, and a graphical display of pressure (see e.g., FIGS. 1C-1D). In some embodiments, the display 3122 covers greater than 70 percent of the surface area of the cover 3141. In this manner, the housing 3100 is configured and shaped to provide both the desired volume of the waste volume 3132 but also to provide a substantial top surface to support the display 3122.

The display 3122 can also allow the operator to provide input (e.g., in response to various prompts) to facilitate operation of the system 3000. For example, in some embodiments, a notification (see e.g., input prompt 1522 as described above) can prompt the user to actuate a button. In other embodiments, the system can prompt and receive user input to identify when the catheter tip has been moved, when fittings have been checked for air leakage, or to confirm completion of any other suitable action as described herein.

The display 3122 can also allow the user to select the appropriate catheter to be used for the procedure. For example, a catheter parameter menu can be provided that provides a list of multiple different catheters that can be selected by the user. For example, the catheter parameter can be a list of catheter manufacturers (see FIG. 1E), a list of catheter diameters (see FIG. 1F), catheter lengths, catheter material construction, catheter tip design, etc. In some embodiments, the user can first select the catheter manufacturer from the display screen (FIG. 1E). The display 3122 can then provide a list of catheter diameters or diameter ranges (FIG. 1F). The user can then select the catheter size that corresponds to the catheter that is to be used for the procedure. In response to the user input, the system 3000 then loads an aspiration profile from a list of multiple preset aspiration profiles each associated with a different catheter to be used during the procedure that corresponds to the selected catheter, as described herein. The aspiration profile can be stored within controller 3220 (e.g., within a processor or a memory device, as described above) and can be read, manipulated, and used by the controller 3220 (e.g., by the aspiration module) to execute any of the methods described herein. The aspiration profile can include any suitable information to facilitate operation of the selected catheter during a thrombectomy procedure in an efficacious manner. For example, in some embodiments, the aspiration profile includes an upper pressure limit (Pupper), a lower pressure limit (Plower), an aspiration speed (Aspeed), and an infusion speed (Ispeed) for each of the catheters within the list of catheters. These profile parameters are used by the APA in the Smart Mode. As described above, the system 3000 is configured to operate within a smart range, which is within the Pupper and Plower values. The Smart Mode described above operates cyclically to approach the Pupper and Plower range without exceeding either, controlled by a selected algorithm (APA) associated with the particular catheter being used.

The controller 3220 can be configured the same as or similar to controller 1220 described above and can include one or more processors, one or more memory devices, an input module, an output module and an aspiration module (each not shown in FIG. 4). The input module and output modules can be implemented in at least one of the memory devices or processors of the controller 3220. The input module, output module, and aspiration module can be separate components outside of the processors and memory devices or can be included within a processor or memory device. In some embodiments, a switch is coupled to the pump assembly and configured to send an indication to the aspiration module when the pump assembly has been decoupled from the housing. The aspiration module is configured to automatically shut off the pump assembly based on the receipt of the indication.

In some embodiments, a lid (not shown) is removably coupled to the second housing portion 3110 and encloses a portion of the waste volume 3132 as described above for system 2000. The lid can also include a transparent portion as described above. In some embodiments, the waste volume 3132 includes a clot cavity that is in direct fluid communication with the outlet port 3140. A clot retainer (not shown in FIG. 4), such as the clot retainer 2134 described above, can be removably coupled to the housing 3100 within the waste volume 3132. For example, the waste volume 3132 can include a clot cavity that is in direct fluid communication with the outlet port 3140 and the clot retainer can be disposed within the clot cavity. The clot retainer can be configured the same as and function the same as the clot retainer 2134 described above. The lid is disposable over the clot retainer, and the transparent portion of the lid can allow viewing of the clot retainer through the lid. In some embodiments, the clot retainer includes a tab extending upwardly from the surface of the clot retainer, and the tab includes an alignment feature configured to matingly engage the lid. For example, the lid can include a mating coupling feature to couple to the tab. The lid can also include an attachment mechanism to removably couple the lid to the housing 3100. For example, the attachment mechanism can include one or more magnets.

In some embodiments, the housing 3100 includes a mounting shoulder (not shown) within the waste volume 3132, on which the clot retainer is supported. In some embodiments, the mounting shoulder positions the clot retainer such that at least the second portion of a surface of the clot retainer is at an angle relative to a base surface of the housing 3100. In some embodiments, the waste volume 3132 has a height defined between the lid and a base surface of the housing 3100, and the surface of the clot retainer is positioned relative to the lid at a distance equal to between 5% and 25% of the height of the waste volume 3132.

In some embodiments, the outlet port 3140 is positioned in the housing 3100 between the pump cavity 3130 and the waste volume 3132 at a distance from the base surface of the housing 3100 that is greater than a distance between a portion of the clot retainer and the base surface of the housing 3100, and the outlet port 3140 is in fluid communication with the waste volume 3132. In some embodiments, a centerline of the outlet port 3140 extends parallel with the base surface of the housing. In some embodiments, at least one light (not shown in FIGS. 3A-3C) is coupled to the housing 3100 and/or the pump assembly 3210 and configured to illuminate the waste volume 32132. For example, at least one light can be coupled to the pump assembly 3210 and provide illumination through an opening in a housing of the pump assembly 3210 and into the waste volume 3132. In some embodiments, at least one light can be coupled to an interior wall of the housing 3100 adjacent the waste volume 3132. In some embodiments, the waste volume 3132 has a height defined between the lid and the base surface of the housing 3100, and the surface of the clot retainer is positioned relative to the lid at a distance equal to between 5% and 25% of the height of the waste volume 3132.

In some embodiments, the clot retainer includes a tab extending upwardly from the surface of the clot retainer, and the tab includes an alignment feature configured to matingly engage the lid. For example, the lid can include a mating coupling feature to couple to the tab. The lid can also include an attachment mechanism to removably couple the lid to the housing 3100. For example, the attachment mechanism can include one or more magnets.

Figure 5:
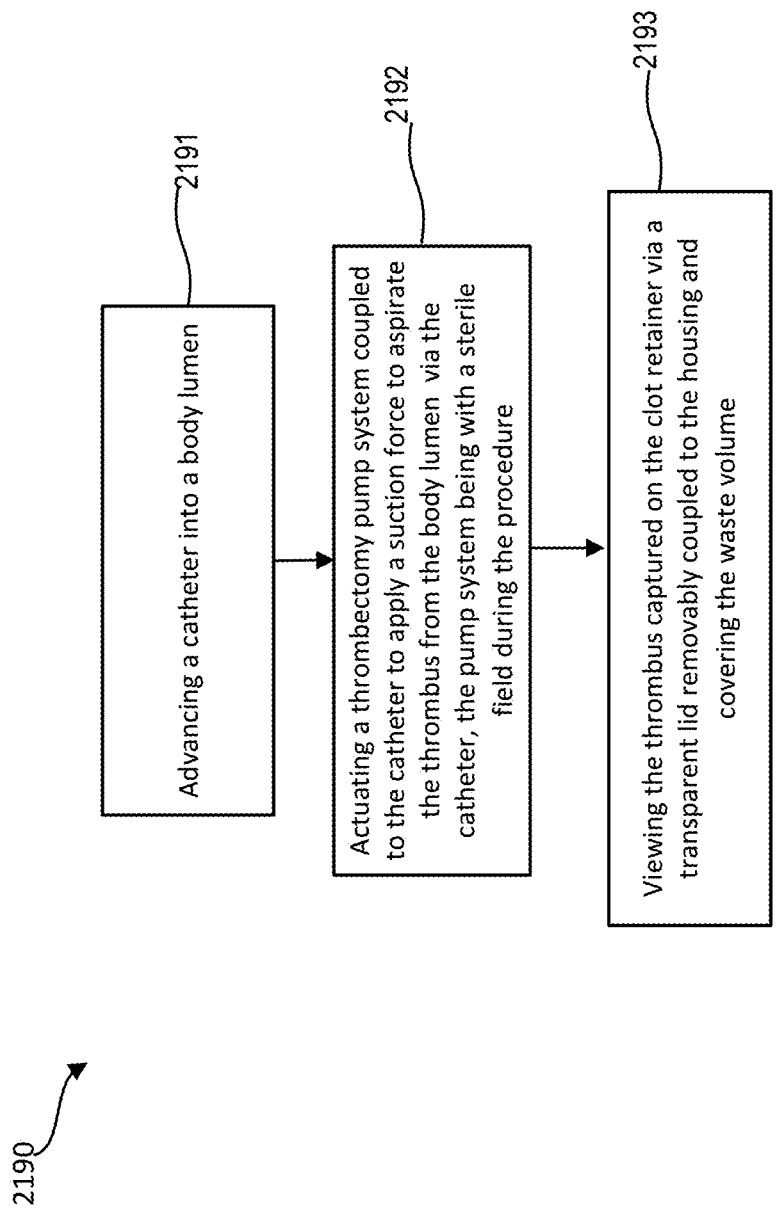
FIG. 5 is a flowchart illustrating a method of using a thrombectomy pump system to remove a thrombus from a body vessel according to an embodiment.

FIG. 5 is a flowchart illustrating a method of removing a thrombus from a body lumen using a thrombectomy pump system as described herein. The method 2190 includes at 2191, advancing a catheter into the body lumen. At 2192, a thrombectomy pump system coupled to the catheter is actuated to apply a suction pressure to aspirate the thrombus from the body lumen via the catheter. The thrombectomy pump system being within a sterile field during the thrombectomy procedure on a patient. The thrombectomy pump system includes a pump assembly including a pump coupled within a housing, a waste volume defined by the housing, and a clot retainer removably coupled to the housing within the waste volume. The method further includes at 2193, viewing the thrombus captured on the clot retainer via a transparent lid removably coupled to the housing and covering the waste volume. In some embodiments, the thrombectomy pump assembly includes at least one light disposed adjacent the waste volume, and the method further includes actuating the at least one light to illuminate the waste volume.

In some embodiments, after capturing the thrombus in the clot retainer, the pump assembly is removed from the housing and the thrombus captured on the clot retainer within the waste volume is discarded. In some embodiments, the first housing portion is removably coupled to the second housing portion with a coupling mechanism, and the removing the pump assembly from the housing includes uncoupling the coupling mechanism.

In some embodiments, the thrombectomy pump system further includes an inlet hose coupled to the pump and coupled to the catheter, and the method further decoupling the catheter from the inlet hose, actuating the thrombectomy pump system to provide suction through the inlet hose, and using the inlet hose to suction biological matter from an exterior of the patient to within the waste volume.

Figure 6:
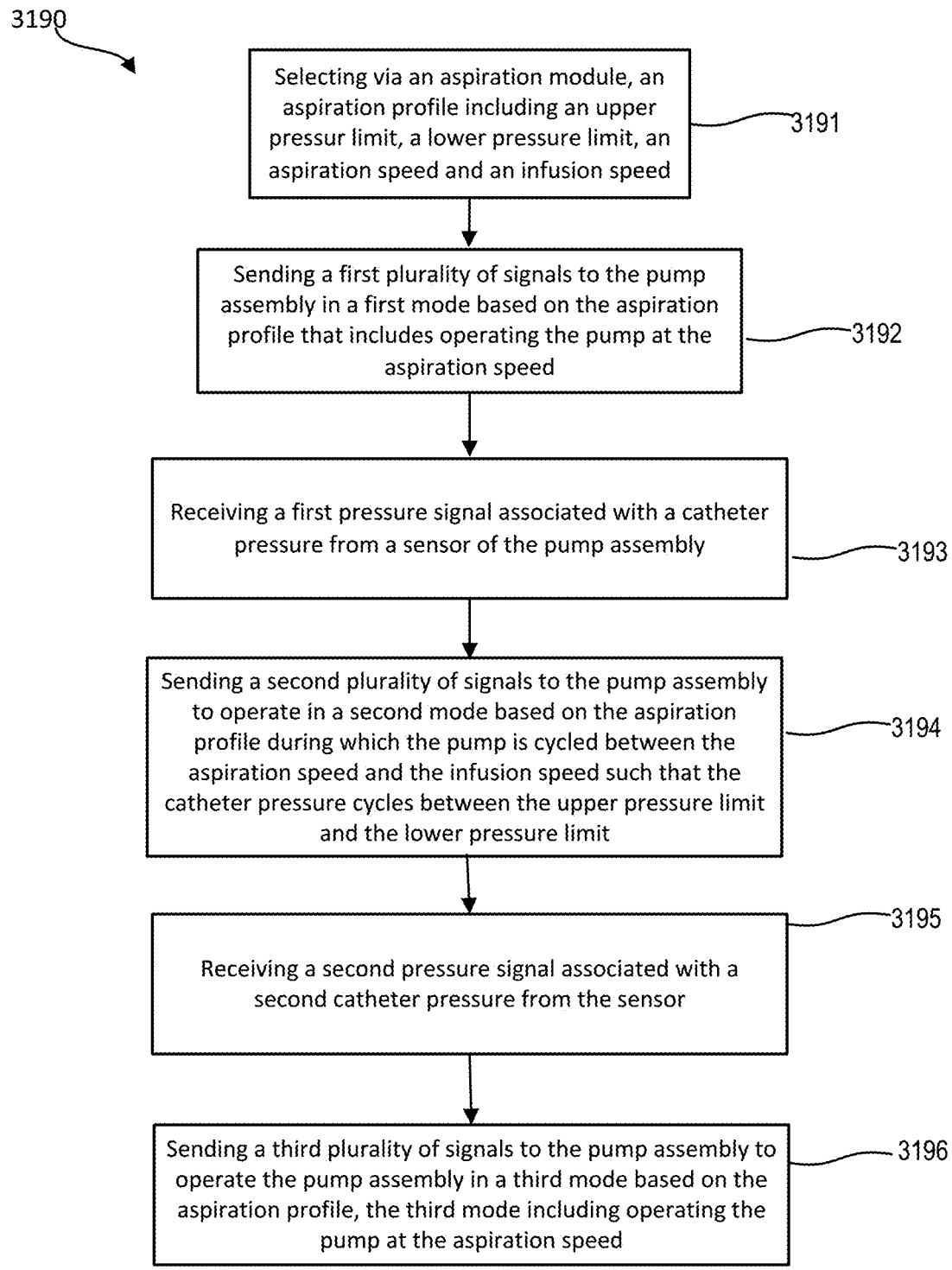
FIG. 6 is a flowchart illustrating a method of using a thrombectomy pump system to remove a thrombus from a body vessel according to an embodiment.
Figure 7:
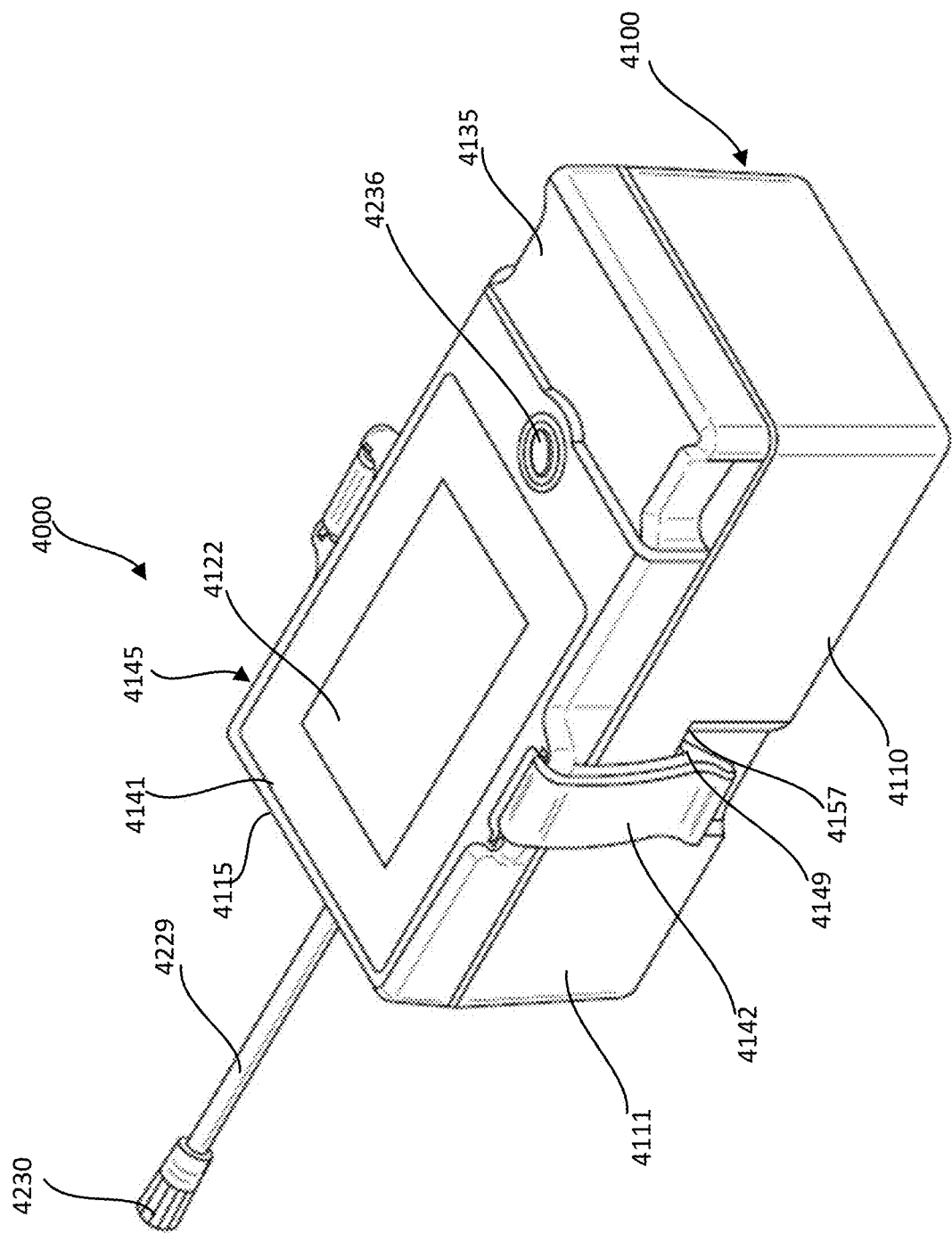
FIG. 7 is a front perspective view of a thrombectomy pump system according to an embodiment.
Figure 8:
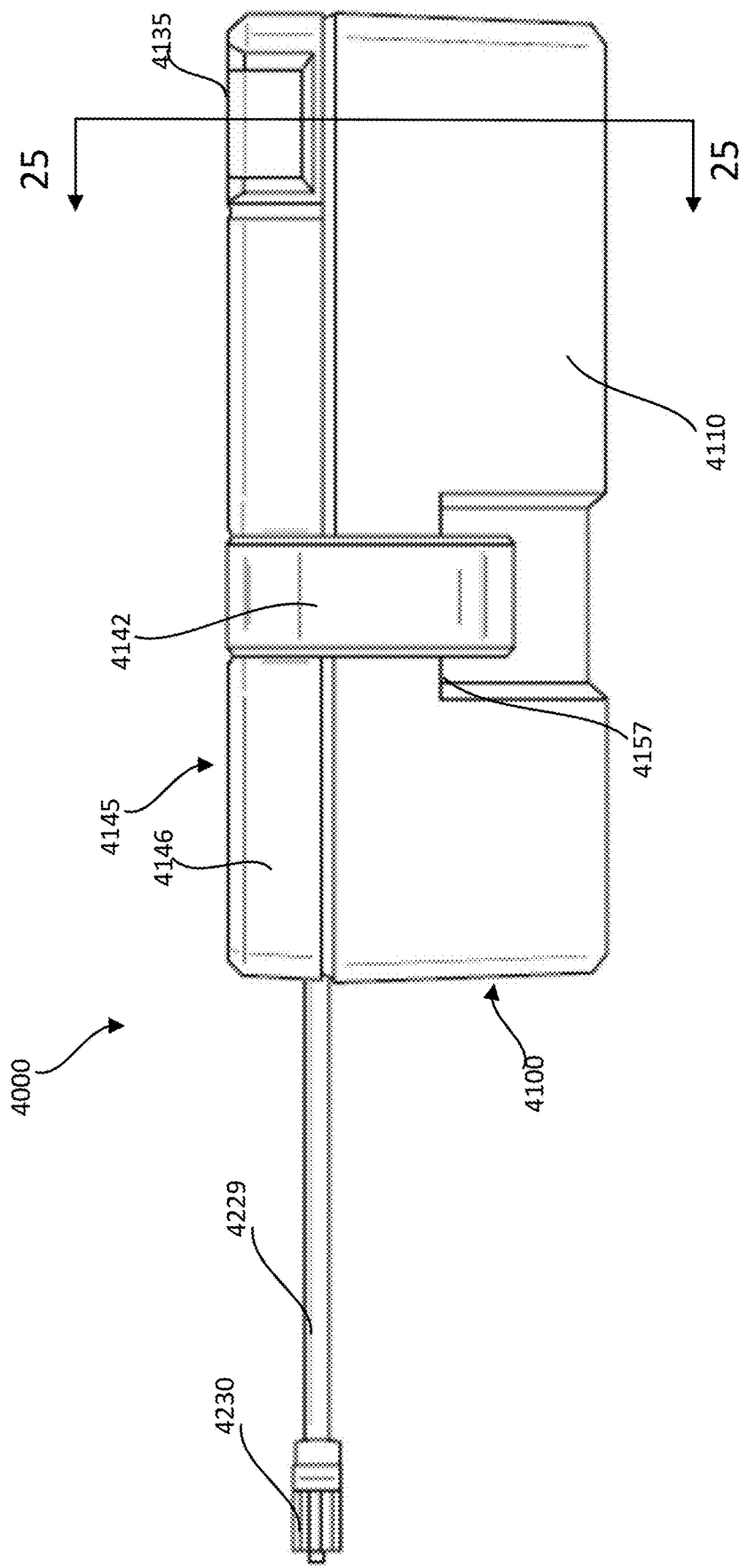
FIG. 8 is a front view of the thrombectomy pump system of FIG. 7.
Figure 9:
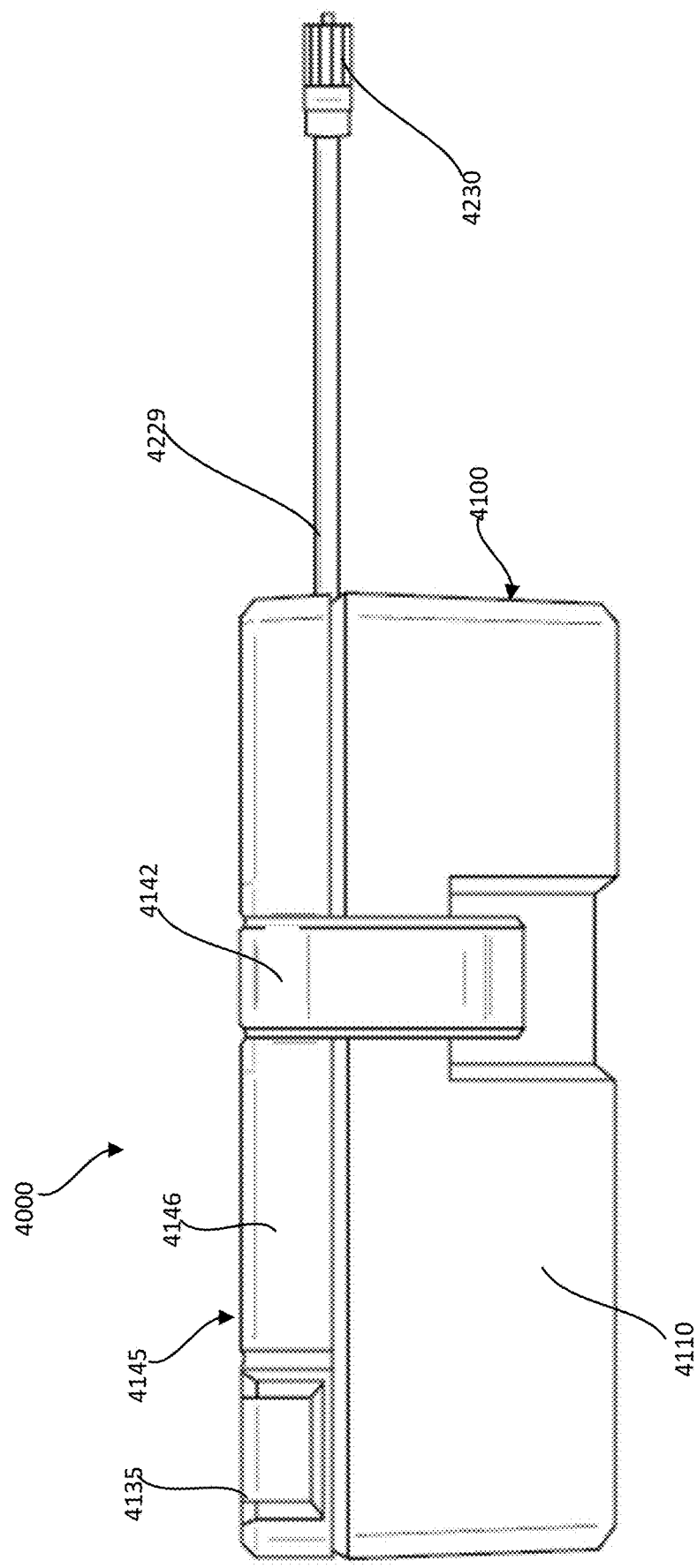
FIG. 9 is a rear view of the thrombectomy pump system of FIG. 7.
Figure 10:
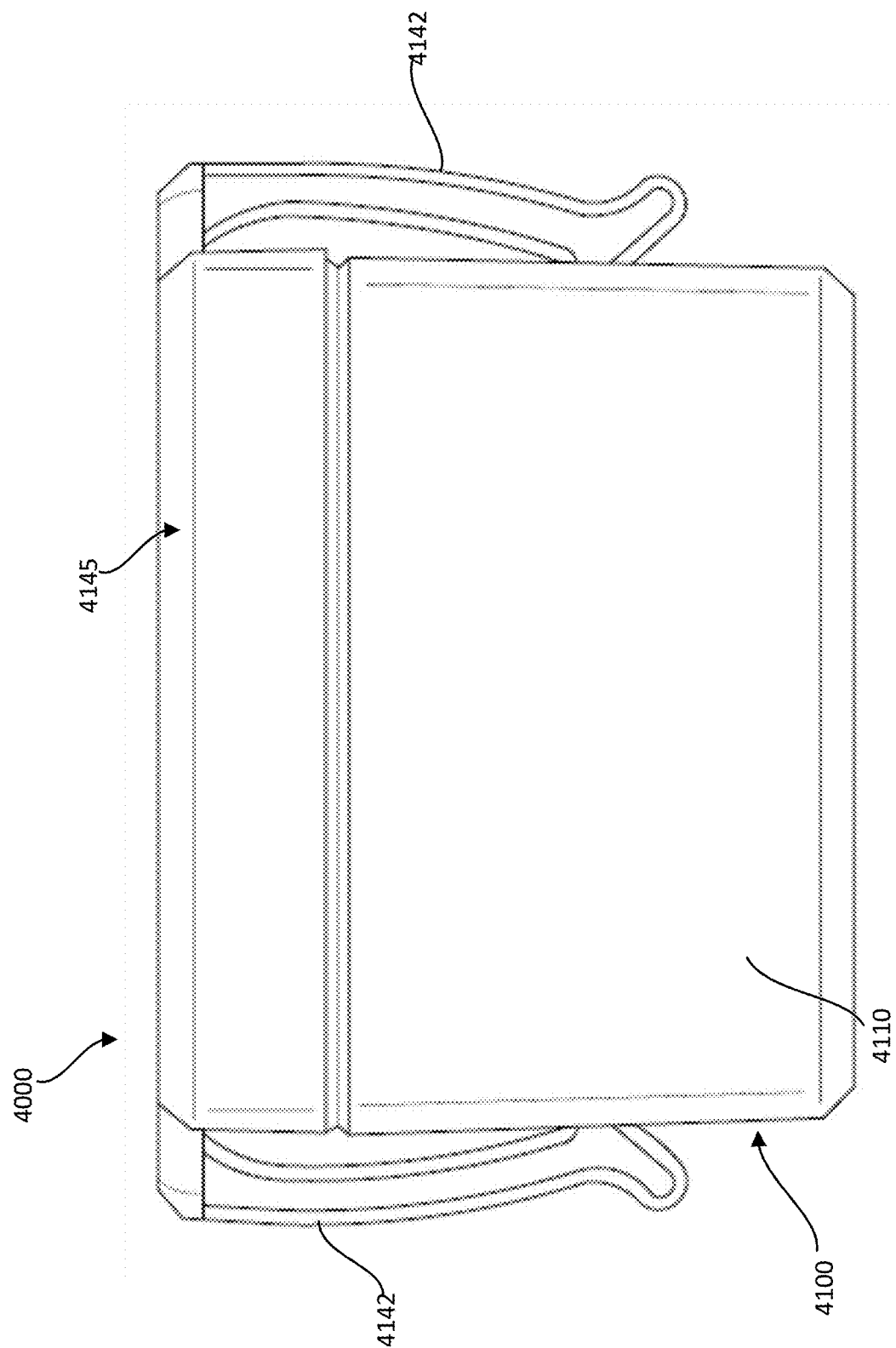
FIG. 10 is a right side view of the thrombectomy pump system of FIG. 7.
Figure 11:
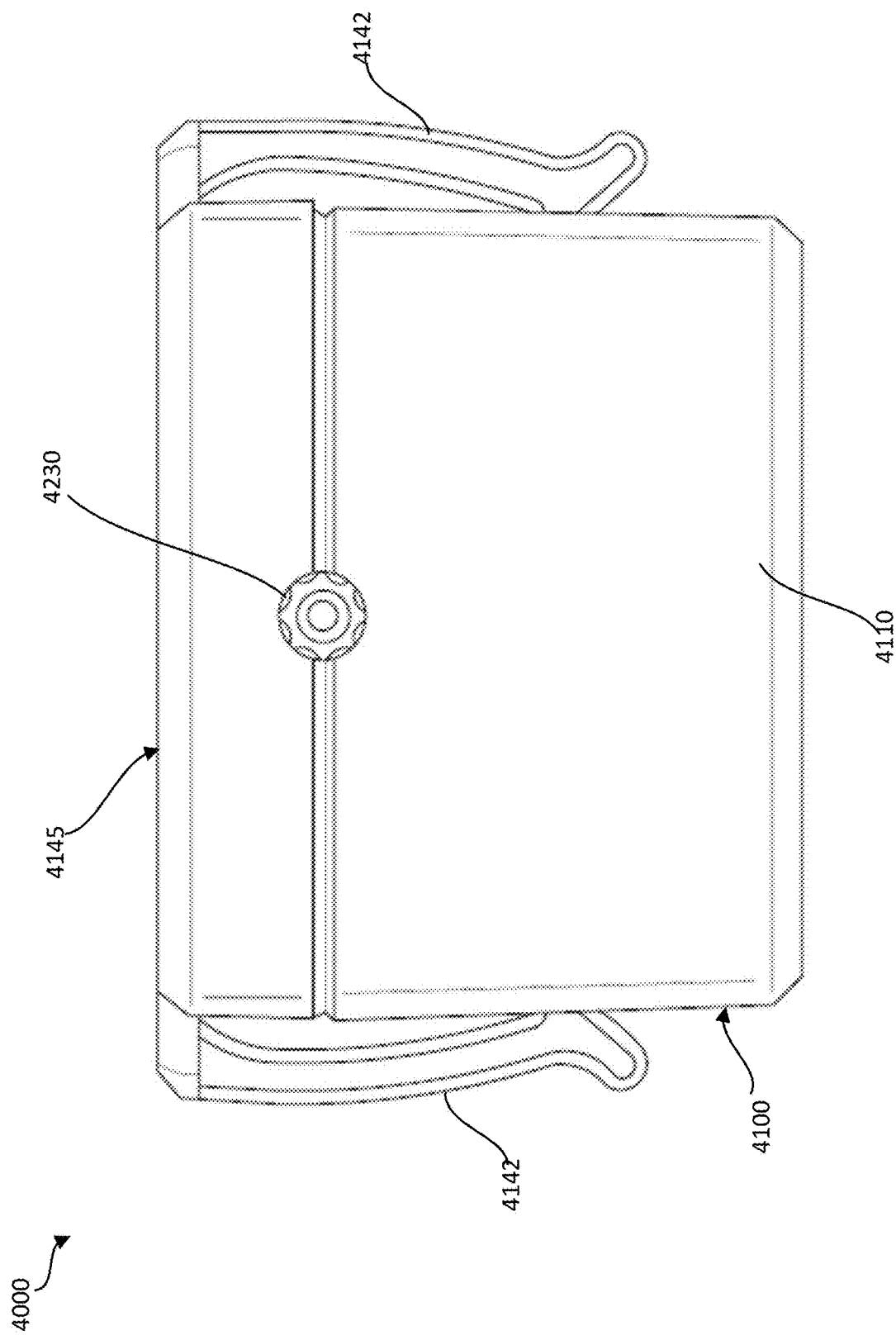
FIG. 11 is a left side view of the thrombectomy pump system of FIG. 7.
Figure 12:
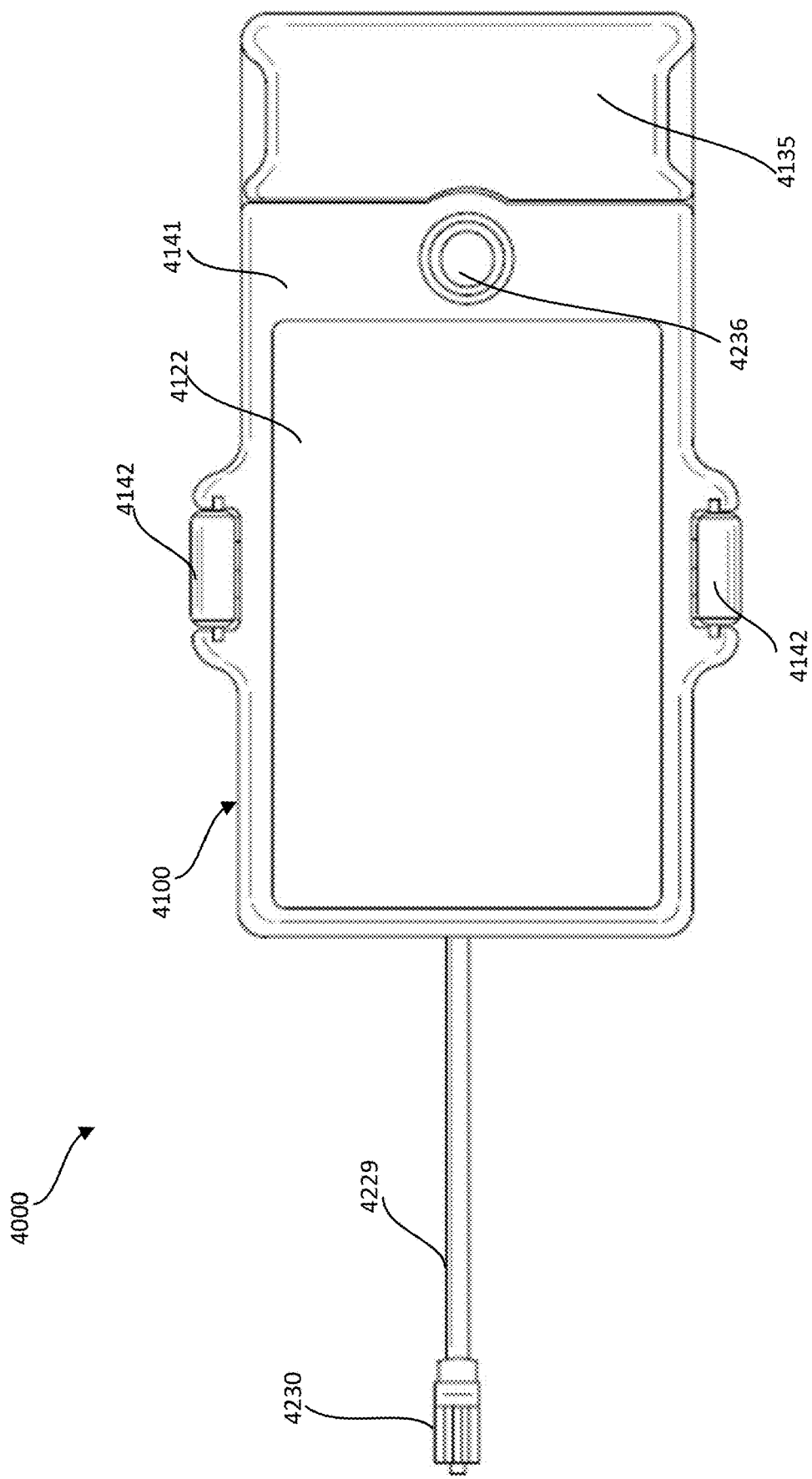
FIG. 12 is a top view of the thrombectomy pump system of FIG. 7.
Figure 13:
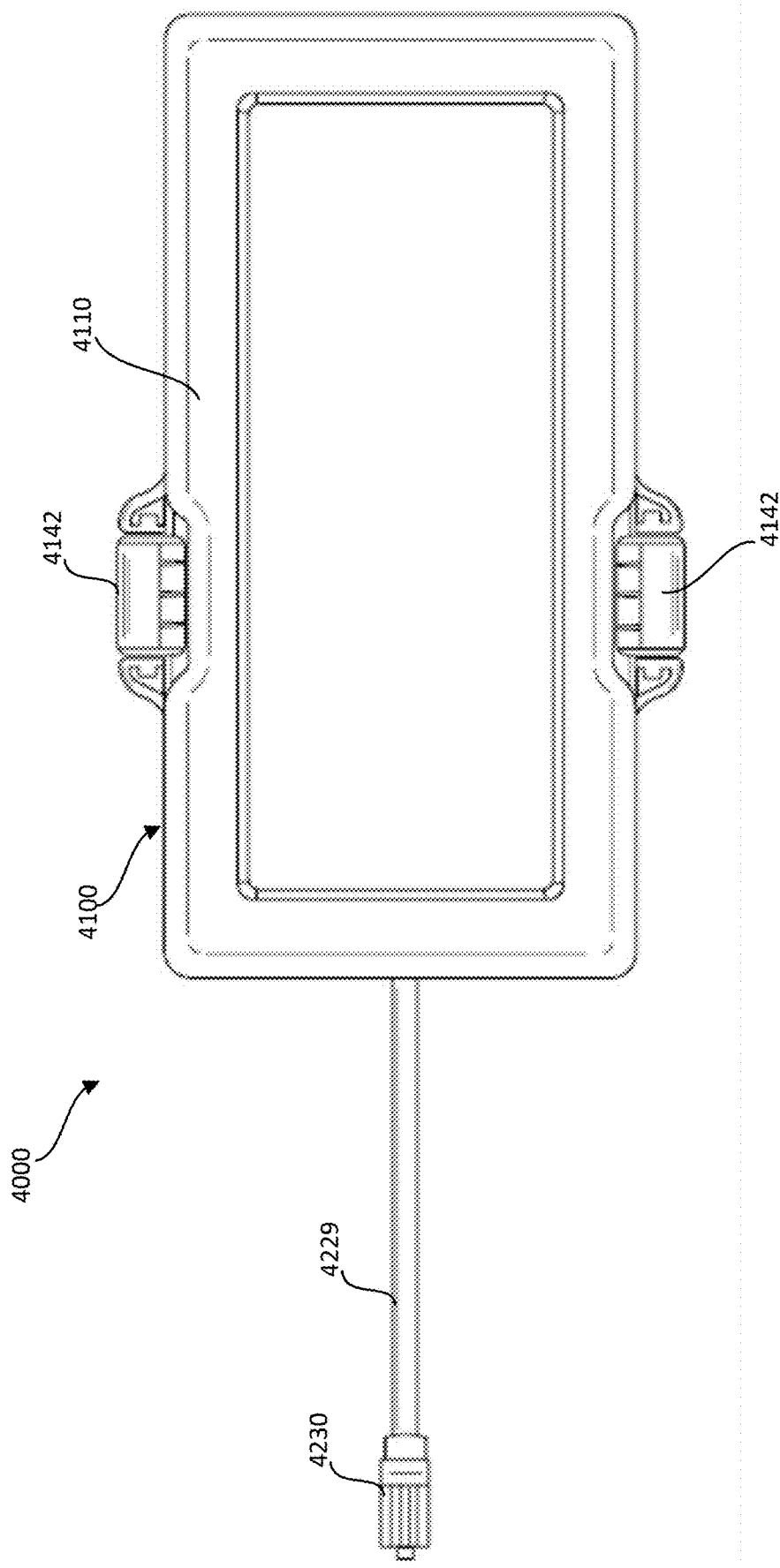
FIG. 13 is a bottom view of the thrombectomy pump system of FIG. 7.

FIG. 6 is a flowchart illustrating a method of aspirating a thrombus from a body lumen via a catheter coupled to a pump assembly including a pump. The method 3190 includes at 3191, selecting, via an aspiration module, an aspiration profile. The aspiration profile includes an upper pressure limit, a lower pressure limit, an aspiration speed, and an infusion speed. At 3192, a first plurality of signals is sent via the aspiration module to the pump assembly to operate the pump assembly in a first mode based on the aspiration profile. The first mode includes operating the pump at the aspiration speed. At 3193 a first pressure signal is received at the aspiration module and is associated with a catheter pressure from a sensor of the pump assembly. At 3194, a second plurality of signals is sent via the aspiration module to the pump assembly to operate the pump assembly in a second mode based on the aspiration profile. During the second mode the pump is cycled between the aspiration speed and the infusion speed such that the catheter pressure cycles between the upper pressure limit and the lower pressure limit. At 3195, a second pressure signal is received at the aspiration module and is associated with a second catheter pressure from the sensor of the pump assembly. At 3196, a third plurality of signals is sent via the aspiration module to the pump assembly to operate the pump assembly in a third mode based on the aspiration profile. The third mode includes operating the pump at the aspiration speed.

In some embodiments, after receiving the second pressure signal associated with the second catheter pressure from the sensor of the pump assembly, a notification is sent to withdraw the catheter from the blood vessel if the second catheter pressure is below a preset pressure limitation indicating a plugged state. In some embodiments, the pump assembly includes a housing with a first housing portion coupled to a second housing portion, and the method further receiving at the aspiration module an indication from a switch coupled to the housing that the second housing portion has been decoupled from the first housing portion. Based on receipt of the indication, the pump assembly is automatically shut off.

FIGS. 7-30 illustrate an embodiment of a thrombectomy pump system 4000 (also referred to as "system"). The system 4000 can include the same or similar features and functions as described above for systems 1000, 2000 and 3000 and/or as described for other thrombectomy pump systems described herein. The system 4000 can be coupled to a catheter and used in a procedure to remove an object from a blood vessel, such as a blood clot. The thrombectomy pump system 4000 (also referred to as "system") includes a housing 4100, a pump assembly 4210 disposed within the housing 4100, a clot retainer 4134, a lid 4135, and a cover assembly 4145. The housing 4100 includes a first housing portion 4115 that defines a pump cavity 4130 (see, e.g., FIGS. 14F, 15, 17 and 18) and a second housing portion 4110 that defines a waste volume 4132 (see, e.g., FIGS. 14A-14F). The waste volume 4132 surrounds the pump cavity 4130 and can hold, for example, a volume of about 1000 cubic centimeters of fluid and/or other biological material. In some embodiments, the waste volume 4132 has a volume between 500 and 1000 cubic centimeters. This arrangement allows for a more compact overall footprint for the system 4000, as well as providing for a larger surface area for the cover assembly 4145 (and thus, the display 4122). Accordingly, the system 4000 is a compact system that can be operated within the sterile field. For example, having the waste volume 4132 surround the pump cavity 4130 (and the pump assembly 4210) allows all of the excess volume not occupied by the pump cavity 4130 to be available to receive waste fluids. Moreover, because the waste volume 4132 is integrated into the housing 4100 along with the pump cavity 4130 (and the pump assembly 4210), there are no external fluid connections between the pump output and the waste volume 4132, which reduces the likelihood of leaks. Although the pump cavity 4130 is shown as being surrounded by the waste volume 4132 on four sides and the bottom, in other embodiments, the pump cavity 4130 can be partially surrounded by the waste volume 4132. For example, in some embodiments, the pump cavity 4130 can be surrounded only on two sides.

In some embodiments, the second housing portion 4110 that defines the waste volume 4132 can be formed with a transparent material (see, e.g., FIGS. 14A-14F) or can include a portion that is transparent to allow a user to view into the waste volume 4132 and the contents therein. As shown, for example, in FIGS. 14A, 14D and 14E, the second housing portion 4110 includes indicia 4111 indicating volume levels within the waste volume 4132. The waste volume 4132 is configured to receive blood and other biological material that is pumped in through the catheter and into the waste volume 4132.

Figure 25:
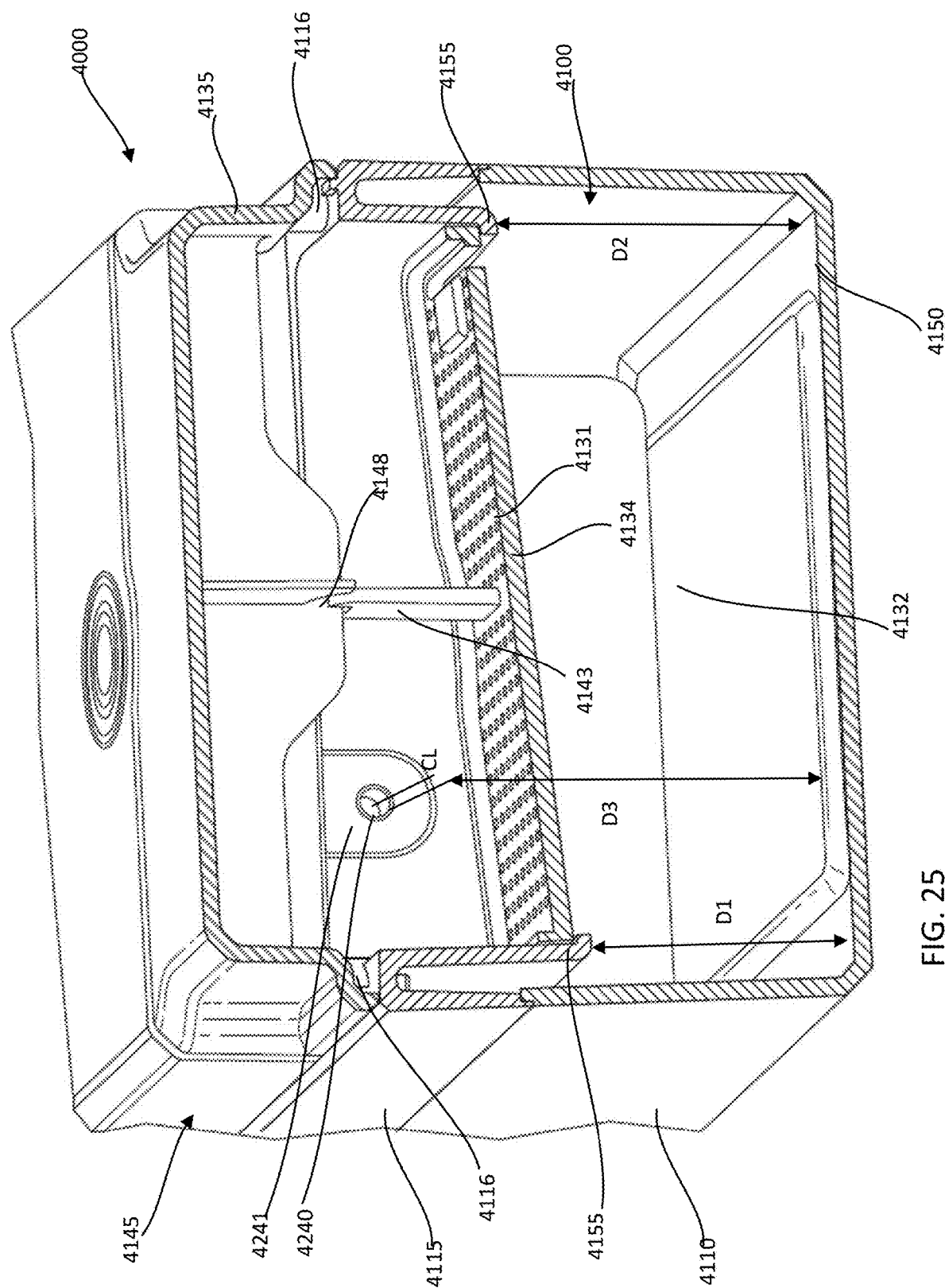
FIG. 25 is a cross-sectional perspective view taken along line 25-25 in FIG. 8.
Figure 26:
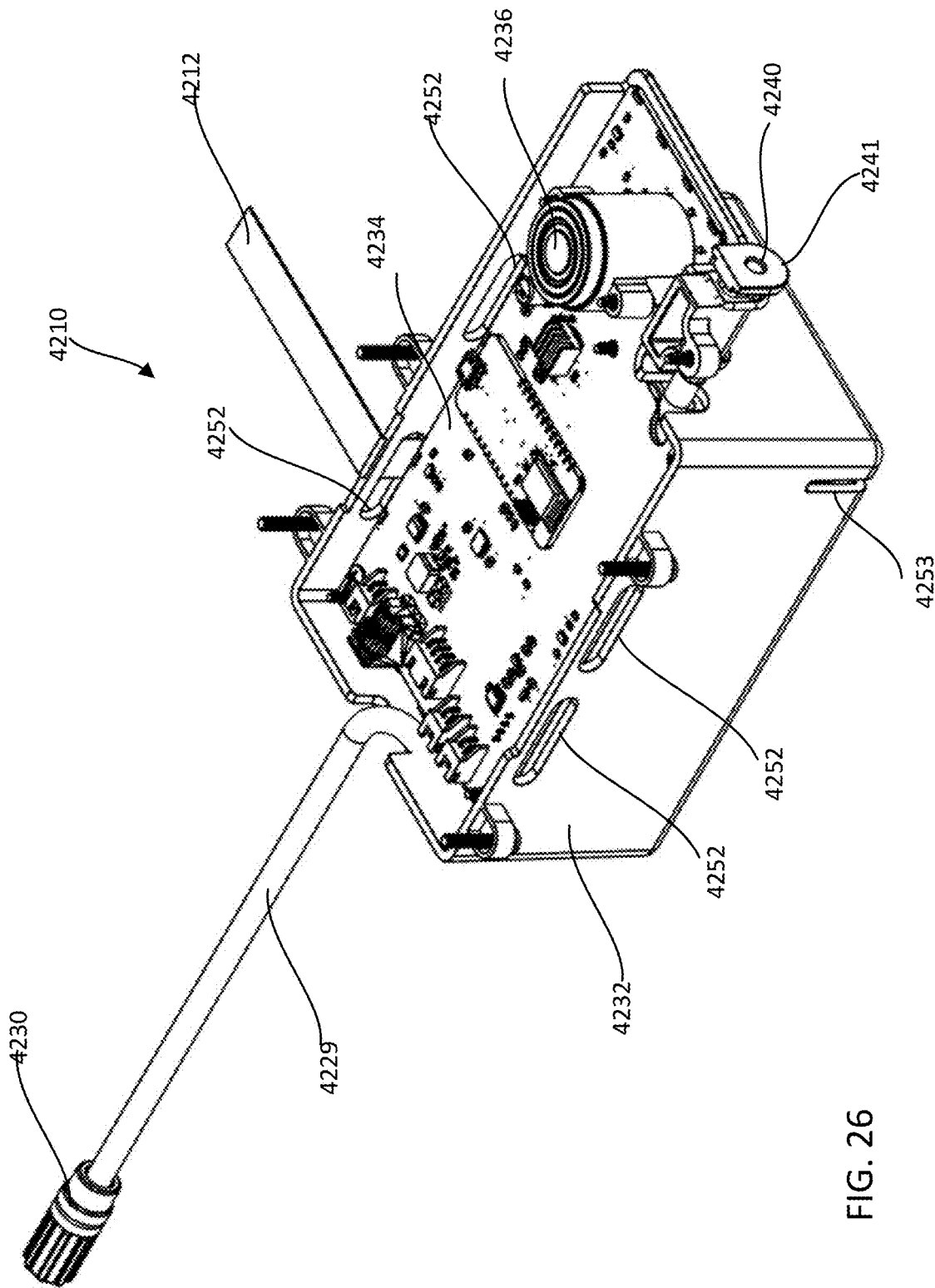
FIG. 26 is a perspective view of the pump assembly of the thrombectomy pump system of FIG. 7.
Figure 27:
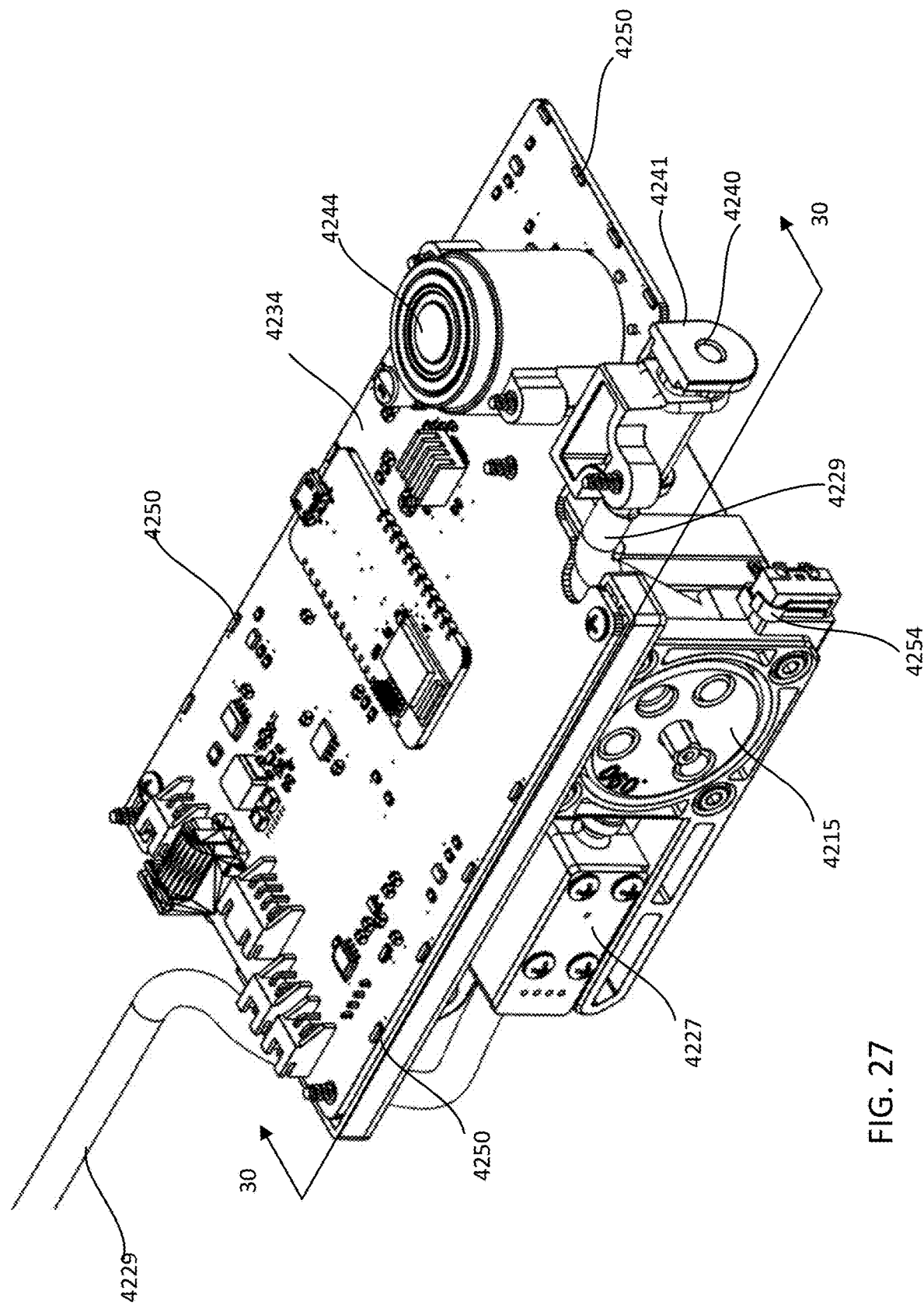
FIG. 27 is a perspective side view of the pump assembly of FIG. 26 with the pump housing removed for illustration purposes.
Figure 28:
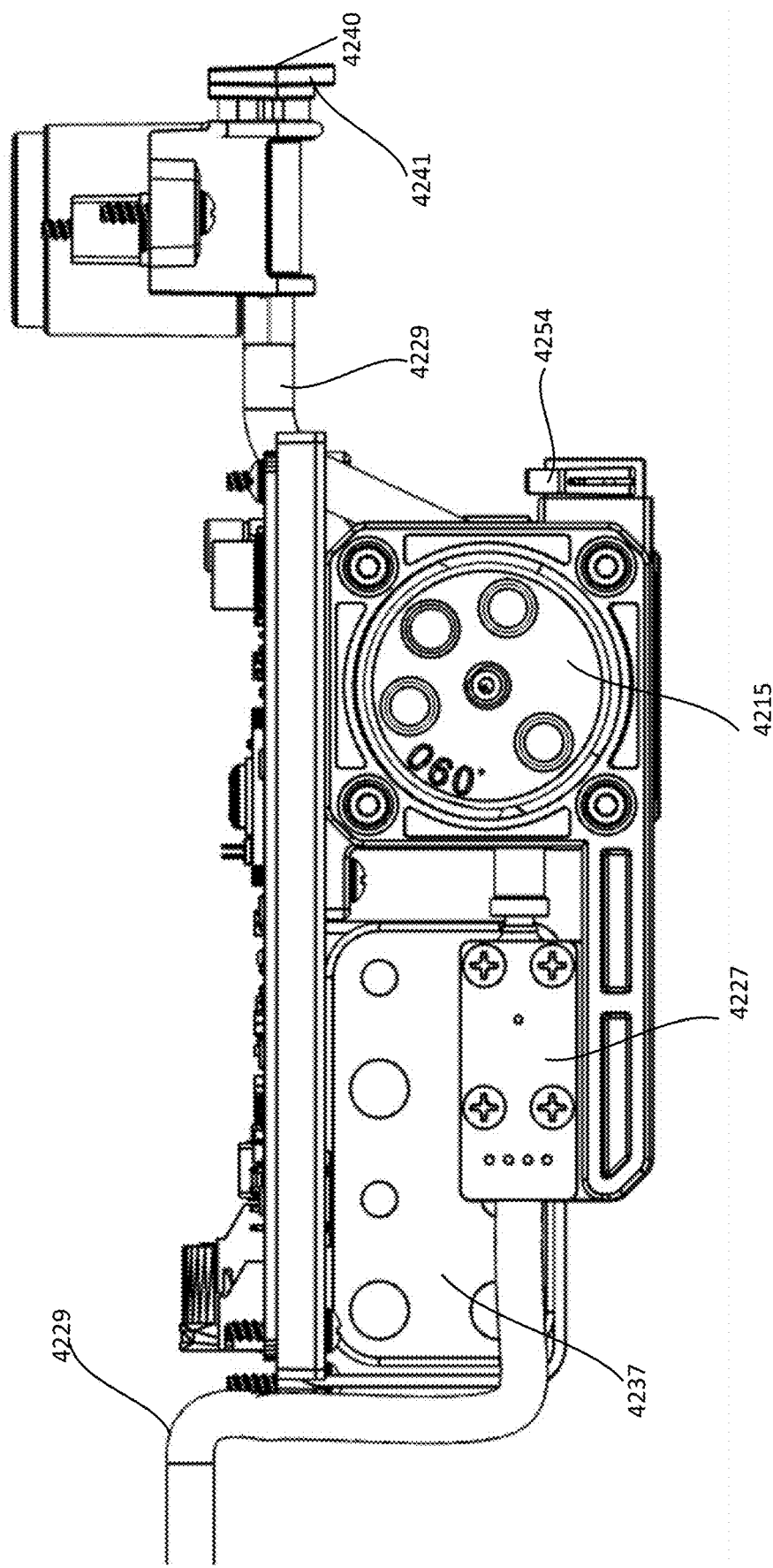
FIG. 28 is a side view of the pump assembly of FIG. 27 with the pump housing removed.

The clot retainer 4134 is removably coupled to the housing 4100 within a clot cavity portion 4117 (see, e.g., FIGS. 14F, 15-18) of the waste volume 4132. The clot retainer 4134 includes a tab 4143, a floor 4123 and a perimeter rim portion 4124 as shown, for example, in FIGS. 22B, 23 and 24. The floor 4123 includes a top surface 4131 having a first portion defining multiple openings 4138 and a second portion defining a bypass opening 4137, as shown, for example, in FIGS. 22B and 23. The tab 4143 extends upwardly from the top surface 4131 and defines a cutout 4151 (see e.g., FIGS. 22B and 23). As shown, for example, in FIG. 25, the housing 4100 includes a mounting shoulder 4155 within the clot cavity portion 4117 of the waste volume 4132, on which the perimeter rim portion 4124 of the clot retainer 4134 is supported. The mounting shoulder 4155 supports the clot retainer 4134 such that the clot retainer 4134 is angled relative to a base surface 4150 of the housing 4100. As shown in FIG. 25, a first end of the clot retainer 4134 is at a first distance D1 relative to the base surface 4150 of the housing 4100 and a second end of the clot retainer 4134 is at a second distance D2 relative to the base surface 4150 of the housing, and the second distance D2 is greater than the first distance D1. In this manner, the floor 4123 slopes downward from the bypass opening 4137 towards the first end of the clot retainer 4134. This arrangement allows clots and materials received to collect on the clot retainer 4134 without inadvertently passing through the bypass opening 4137 unless the waste level collecting on the floor 4123 (e.g., due to the openings 4138 being obstructed) reaches a desired level. The tab 4143 extends upwardly at a slight angle relative to the floor 4123 of the clot retainer 4134 such that when the clot retainer 4134 is disposed on the shoulder 4155, the tab 4143 extends substantially vertically to engage the lid 4135 described in more detail below.

The lid 4135 is removably coupled to the housing 4100 to cover the clot retainer 4134 and can include a transparent portion such as a window, or can be entirely transparent as shown in FIGS. 14A-14E to allow viewing of the clot retainer 4134 through the lid 4135. The tab 4143 of the clot retainer 4134 engages an alignment feature 4148 on a bottom side of the lid 4135 (see, e.g., FIG. 22A). The alignment feature 4148 includes a first portion 4152 that is received within the cutout 4151 of the clot retainer 4134 and a concave portion 4153 that is shaped to receive a top portion of the tab 4143. The lid 4135 also includes an attachment mechanism to removably couple the lid 4135 to the housing 4100. More specifically, the lid 4135 is removably coupled to the housing 4100 with magnets 4116 (see FIG. 25) that magnetically engage ferromagnetic components 4113 (see FIG. 16) coupled to the housing 4100. Alternatively, the magnets 4116 can be coupled to the housing 4100 and the ferromagnetic components 4113 can be coupled to the lid 4135. In some embodiments, the waste volume 4132 has a height defined between the lid 4135 and the base surface 4150 of the housing 4100, and the top surface 4131 of the clot retainer 4134 is positioned relative to the lid 4135 at a distance equal to between 5% and 25% of the height of the waste volume 4132. Said another way, the top surface 4131 upon which the extracted clot will be retained no more than a quarter of the way below the lid 4135. This arrangement limits the likelihood that the blood level within the waste volume 4132 will extend above the top surface 4135 and obstruct the user's view of any clot retained on the surface 4131.

The clot retainer 4134 is used to filter blood and other biological material aspirated from a blood vessel via the catheter, drawn into the system 4000, and conveyed into the waste volume 4132. The multiple openings 4138 of the clot retainer 4134 are sized to allow liquid to flow through the top surface 4131 and into the waste volume 4132 but prevent large objects (larger than the size of the openings 4138) from passing through the openings 4138. For example, during a procedure to remove a blood clot from a blood vessel, the clot can be collected on the clot retainer 4134, while blood and other liquid can pass through the openings 4138 of the clot retainer 4134 and into the waste volume 4132. The transparent portion of the lid 4135 (or the whole lid) can be used to view into the waste volume 4132 to observe the contents introduced therein and captured on the clot retainer 4134. As described above, in some embodiments, the second housing portion 4110 of the housing 4100 defining the waste volume 4132 can be formed with a transparent material or include a portion that is transparent to allow a user to view into the waste volume 4132 and the contents therein.

The bypass opening 4137 allows for overflow of liquid to pass through the clot retainer 4134 and into the waste volume 4132. For example, if an excess volume of liquid begins to collect onto the clot retainer 4134 (e.g., due to the holes becoming obstructed), to prevent the liquid from pooling up on the clot retainer 4134, the bypass opening 4137 provides for the excess liquid to pass through the clot retainer 4134 quickly to prevent overflow and a potential backup of liquid passing back into the pump cavity 4130 (e.g., back into the outlet port 4240). As shown, for example, in FIG. 25, the bypass opening 4137 is positioned at the second end of the clot retainer 4134 such that the bypass opening 4137 is at a greater distance from the base surface 4150 of the housing 4100 than the first end of the clot retainer 4134. Thus, this prevents fluid from passing through the bypass opening 4137 until the level of fluid rises above the position of the bypass opening 4137 at the second distance D2.

The housing 4100 defines a channel 4125 (see, e.g., FIGS. 15, 17 and 18) in a side wall of the housing 4100 between the pump cavity 4130 and the clot cavity 4117 of the waste volume 4132 that places the pump cavity 4130 in fluid communication with the clot cavity 4117 and the waste volume 4132. The channel 4125 receives a tube support portion 4241 of the pump assembly 4210 (see, e.g., FIGS. 25-28) and the tube support portion 4241 includes an outlet port 4240 (see e.g., FIGS. 25-28). The outlet port 4240 receives an end of an aspiration tube 4229 (discussed below) of the pump assembly 4210 and allows for the liquid and other biological material aspirated via the catheter to flow from the pump 4125 into the waste volume 4132. The channel 4125 and outlet port 4240 are positioned above the clot retainer 4134 such that liquid and biological material flows into the waste volume 4132 above the clot retainer 4134. For example, the outlet port 4240 is positioned at a distance D3 from the base surface 4150 of the housing 4100, which is greater than the distance D1 such that liquid and other biological material flows into the waste volume 4132 above the clot retainer 4134. In some embodiments, a centerline CL of the outlet port 4240 extends parallel with the base surface 4150 of the housing 4100. This arrangement reduces the direct impingement of the fluids onto the top surface 4131 of the clot retainer 4134, which could result in undesirable splashing of fluids onto the transparent portion of the lid 4135. Thus, the outlet port 4240 is configured to limit splashing of fluids that could obscure the surgeon's ability to effectively view the contents retained by the clot retainer 4134.

Figure 19:
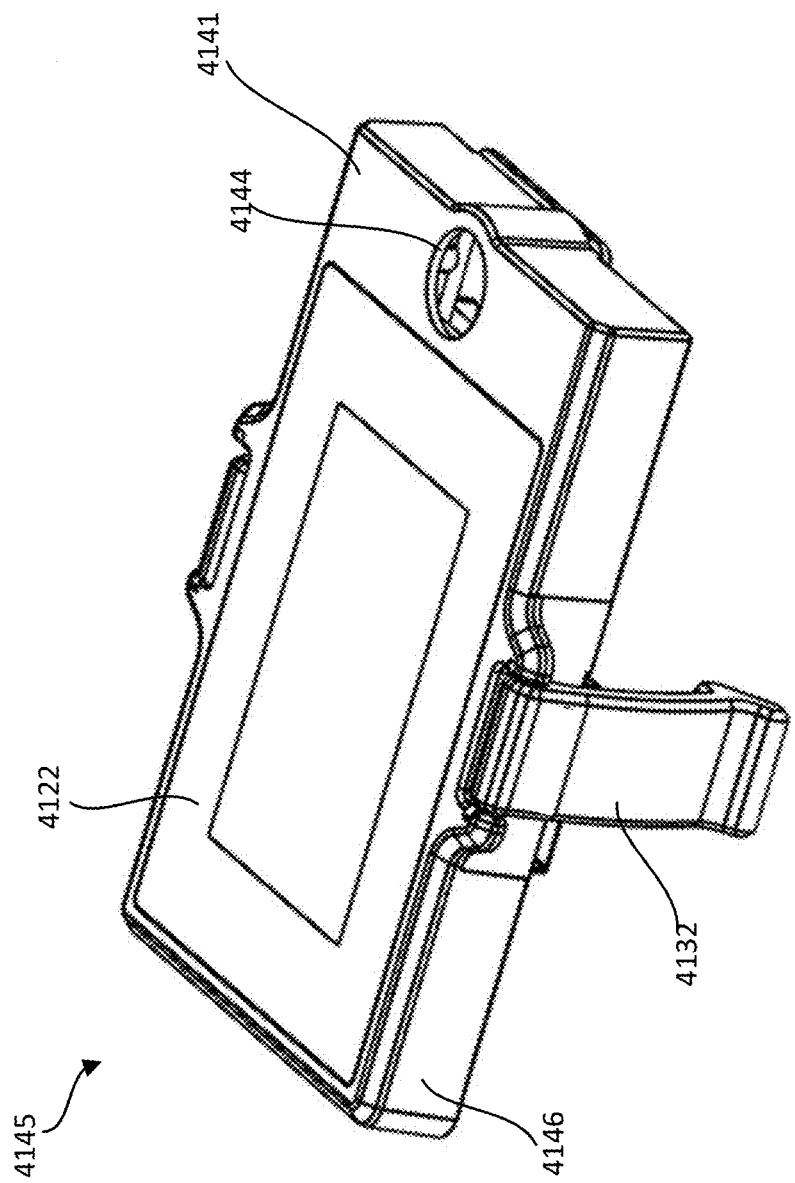
FIG. 19 is a perspective view of the cover assembly of the thrombectomy pump system of FIG. 7.
Figures 21A, 21B:
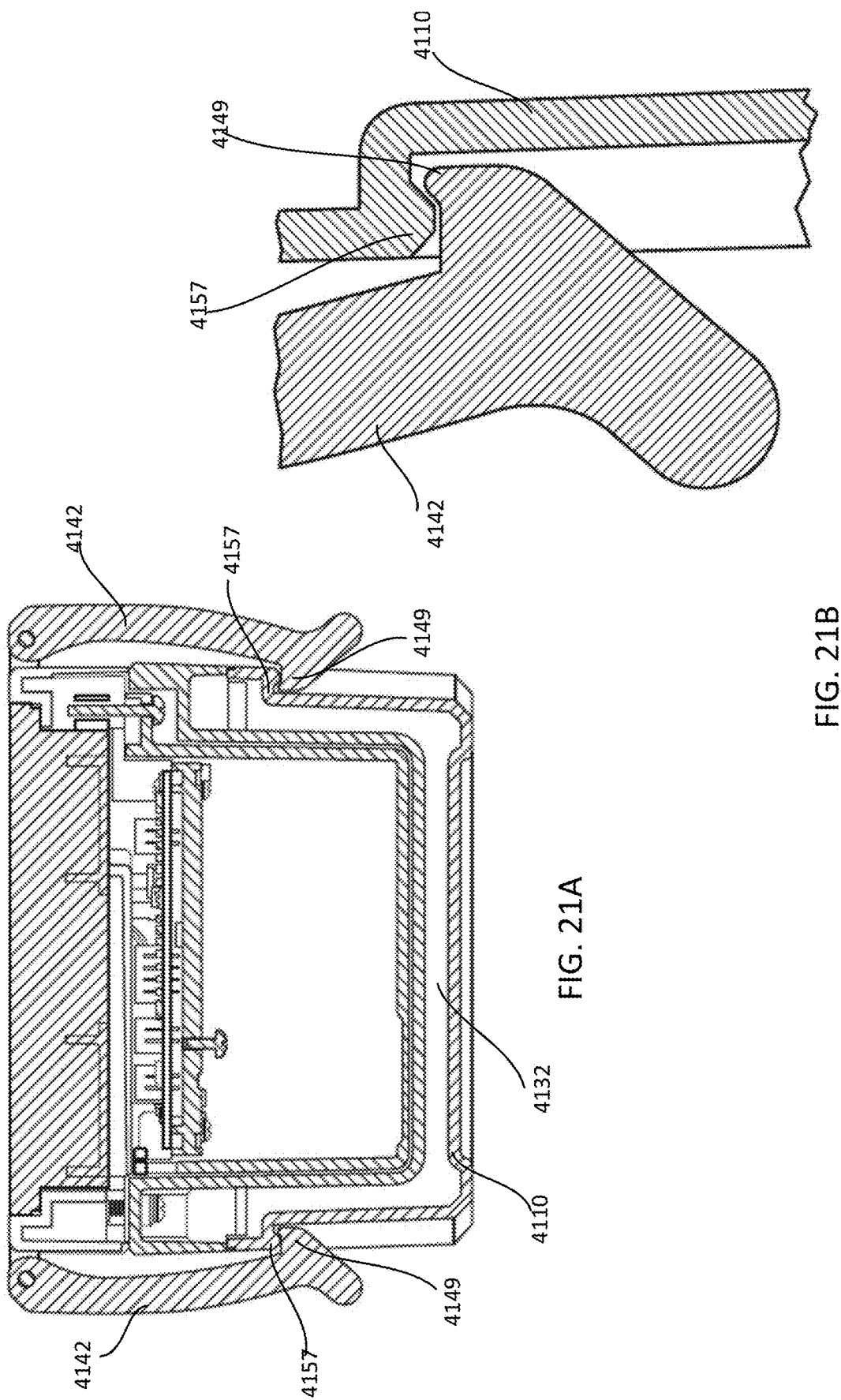
Figures 22A, 22B:
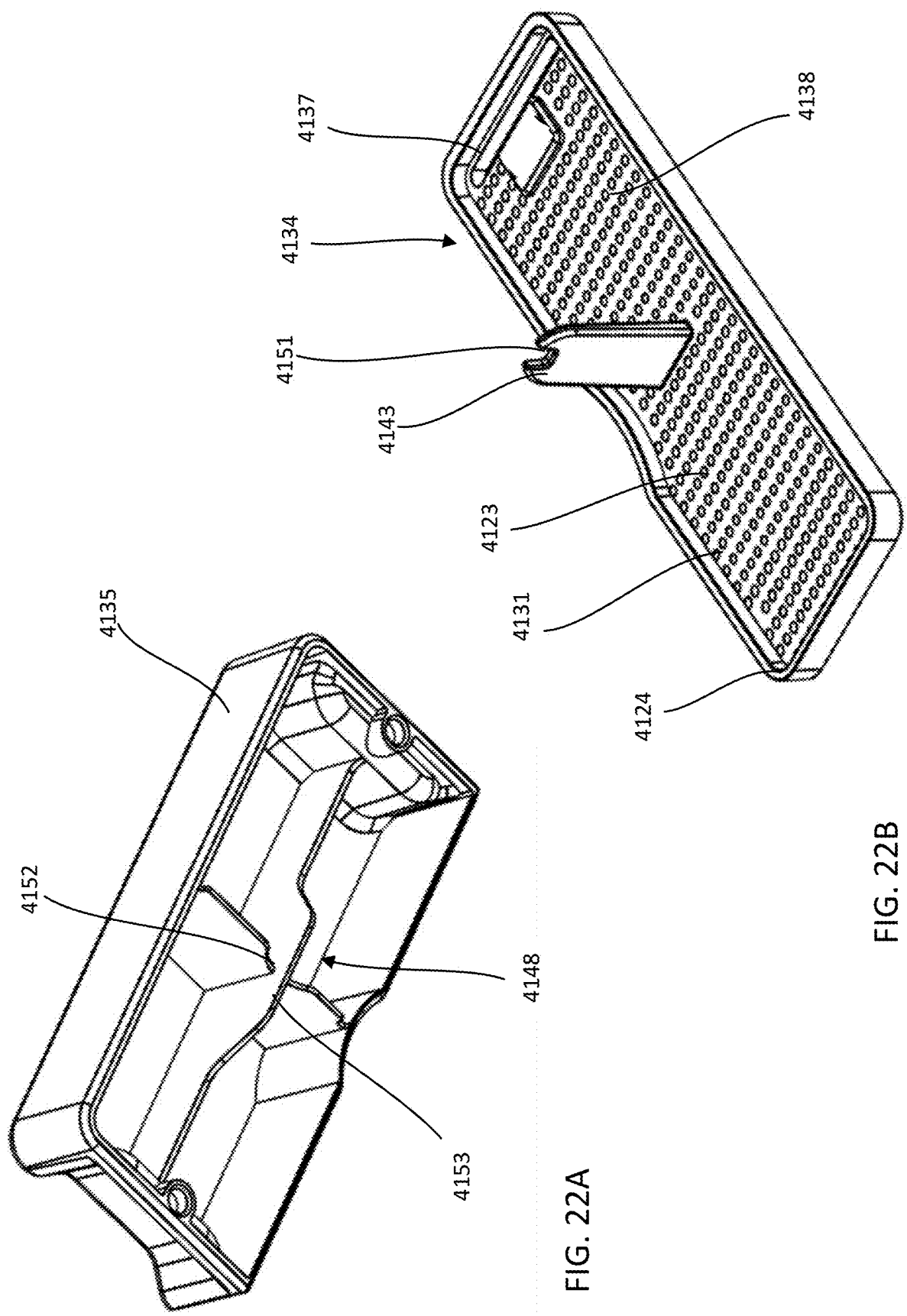
FIG. 22A is a bottom perspective view of the lid of the thrombectomy pump system of FIG. 7.
FIG. 22B is a perspective view of the clot retainer of the thrombectomy pump system of FIG. 7.

The cover assembly 4145 includes a display 4122 coupled to a top cover surface 4141, a top cover housing 4146 and a bottom cover housing 4147 (see, e.g., FIGS. 19 and 20). The cover assembly 4145 also includes latches 4142 that are pivotally coupled to the top cover housing 4146 and used to removably couple the cover assembly 4145 to the housing 4100. More specifically, as shown in more detail, for example, in FIGS. 21A and 21B, the latches 4142 include an engagement lip 4149 that engages a mating edge 4157 of the housing 4100 to form a latch connection. The engagement lip 4149 can be released from the edge 4157 by pulling up on the latches 4142. The cover assembly 4145 (and in some instances, the pump assembly 4120) can then be removed from the housing 4100. The housing 4100 also includes alignment ribs 4156 to help align the cover assembly 4145 to the housing 4100 (see, e.g., FIGS. 16-18). For example, the alignment ribs 4156 can be received in mating grooves in ta bottom side of the cover assembly 4145. The cover assembly 4145 also includes an opening 4144 through which an on/off button 4236 of the pump assembly 4210 extends when the cover assembly 4145 is coupled to the housing 4100.

The display 4122 of the cover assembly 4145 can be used by the user (e.g., surgeon) to actuate various features of the system 4000, monitor pressures and control the overall use and functions of the system 4000 as described above for other embodiments (e.g., the system 1000). The display 4122 can include a touchscreen that displays notifications associated with relevant conditions. Because the display 4122 is coupled to the housing 4100 and the system 4000 can be located in proximity to the patient, the notifications are close to the user and can be easily viewed during a procedure. The notifications can include, for example, the battery level, status, operational mode, duration/time, pressure reading, and a graphical display of pressure (see e.g., display 1122 in FIGS. 1C-1D). In some embodiments, the display 4122 covers greater than 70 percent of the surface area of the cover assembly 4145. In this manner, the system 4000 is configured and shaped to provide both the desired volume of the waste volume 4132 but also to provide a substantial top surface to support the display 4122.

The display 4122 can also allow the operator to select the appropriate catheter to be used for the procedure. For example, a catheter parameter menu can be provided that provides a list of multiple different catheters that can be selected by the user. For example, the catheter parameter can be a list of catheter manufacturers (see FIG. 1E), a list of catheter diameters (see FIG. 1F), catheter lengths, catheter material construction, catheter tip design, etc. In some embodiments, the user can first select the catheter manufacturer from the display screen (FIG. 1E). The display 4122 can then show a list of catheter diameters or diameter ranges (FIG. 1F). The user can then select the catheter size that corresponds to the catheter that is to be used for the procedure. In response to the user input, the system 4000 then loads an aspiration profile from a list of multiple preset aspiration profiles each associated with a different catheter to be used during the procedure that corresponds to the selected catheter as described herein. As described herein, the aspiration profile includes an upper pressure limit (Pupper), a lower pressure limit (Plower), an aspiration speed Aspeed (also referred to as "AS"), and an infusion speed (Ispeed) (also referred to as "IS" or push speed "PS") for each of the catheters within the list of catheters. These profile parameters are used by the APA of the system 4000 in the Smart Mode as described above. As described above, the system 4000 is configured to operate within a smart range, which is within the Pupper and Plower values. The Smart Mode described above operates cyclically to approach the Pupper and Plower range without exceeding either, controlled by a selected algorithm (APA) associated with the particular catheter being used.

As described above, the pump assembly 4210 is positioned within the pump cavity 4130. The pump assembly 4210 (see FIGS. 26-31) operates to provide aspiration and infusion pressures to macerate and remove an object from a blood vessel such as a blood clot. The pump assembly 4210 includes a pump housing 4232, a pump 4215, a motor 4228, a sensor 4227, the aspiration tube 4229, a catheter coupler 4230, a controller embodied in a circuit board 4234, the on/off switch 4236, a battery pack 4237 and a battery pull tab 4212 (see FIGS. 15, 16, 26, 29A and 29D). The circuit board 4234 is operatively coupled to the pump assembly 4210 and includes the electrical components necessary for the controller to control the pump assembly 4210 according to any of the methods described herein. For example, the electrical components can be resistors, capacitors, inductors, switches, memory components, microcontrollers, microprocessors and/or the like. The controller can be configured the same as and provide the same functions as the controller 1220 described above. As described above, the pump assembly 4210 can be coupled to a catheter (not shown in FIGS. 7-31) that can be inserted into a blood vessel of a patient such that the system 4000 can be used to macerate and remove an object, such as a blood clot, from the blood vessel.

The pump 4215 can be, for example, a positive displacement pump, and in this embodiment is shown as a peristaltic pump. The pump 4215 is operatively coupled to and driven by the motor 4228. The motor 4228 can be, for example, a stepper motor. The pump 4215 can be actuated to provide positive and negative pressure to force the object (e.g., clot) out of the blood vessel and within the catheter coupled to the pump system 4000 as described herein. For example, the pump 4215 can provide aspiration and/or infusion pressures to remove an object from the blood vessel, through the catheter coupled to the system 4000, through the aspiration tube 4229, and into the waste volume 4132. The pump 4215 can be actuated to provide different modes of operation; the Smart Mode which uses an Adaptive Pulsative Algorithm (APA) and a Static Mode in which the pump aspirates at essentially constant vacuum. In the Smart Mode, the pump system operates as a "smart device" controlled by the APA unique to a selected aspiration catheter.

The sensor 4227 can be used to measure the fluid pressure in the catheter coupled to the system 4000. The pressure measurement can provide feedback to the controller which can be used to determine which mode the pump 4210 should operate, i.e., if the pump 4215 should operate in the Smart Mode to generate cyclic positive and negative pressures or in the Static Mode to generate constant aspiration.

The controller can include any of the hardware/software modules described herein and can produce any of the notification, signals or other outputs as described herein. For example, in the controller can include one or more processors, one or more memory devices, an input module, an output module, and an aspiration module as described above for controller 1220. The input module can be implemented in at least one of the memory devices or processors of the aspiration controller. As described above, a user (e.g., surgeon) can select one or more catheter parameters such as the catheter manufacturer and catheter size to be used in the procedure. The input module is configured to receive from the user this input associated with the catheter parameter(s) associated with the selected catheter. The aspiration module is configured to select an aspiration profile associated with the catheter parameter from a list of a plurality of preset aspiration profiles each associated with a different catheter. As described above, the aspiration profile includes an upper pressure limit Pupper, a lower pressure limit Plower, an aspiration speed Aspeed, and an infusion speed Ispeed. The aspiration module is configured to send a first set of signals based on the aspiration profile to the thrombectomy pump assembly 4210 to operate the thrombectomy pump assembly 4210 in a first mode. For example, the first mode can include operating the pump 4215 in the Smart Mode to provide cyclic aspiration pressures, or in the Static Mode to provide constant aspiration pressure.

During the procedure, the aspiration module can receive a pressure signal associated with the catheter pressure from the sensor 4227 (e.g., pressure sensor). Based on the pressure signal received, the aspiration module is configured to send a second set of signals based on the aspiration profile to the thrombectomy pump assembly 4210 to operate the thrombectomy pump assembly 4210 in a second mode (e.g., Smart Mode or Static Mode). In some embodiments, the first mode may be the Static Mode and the second Mode may be the Smart Mode. In the second mode the pump 4215 is cycled between the aspiration speed Aspeed and the Infusion speed Ispeed such that the catheter pressure cycles between the upper pressure limit Pupper and the lower pressure limit Plower of the aspiration profile being used. This can be referred to as operating within the smart range as described above.

Figure 29A:
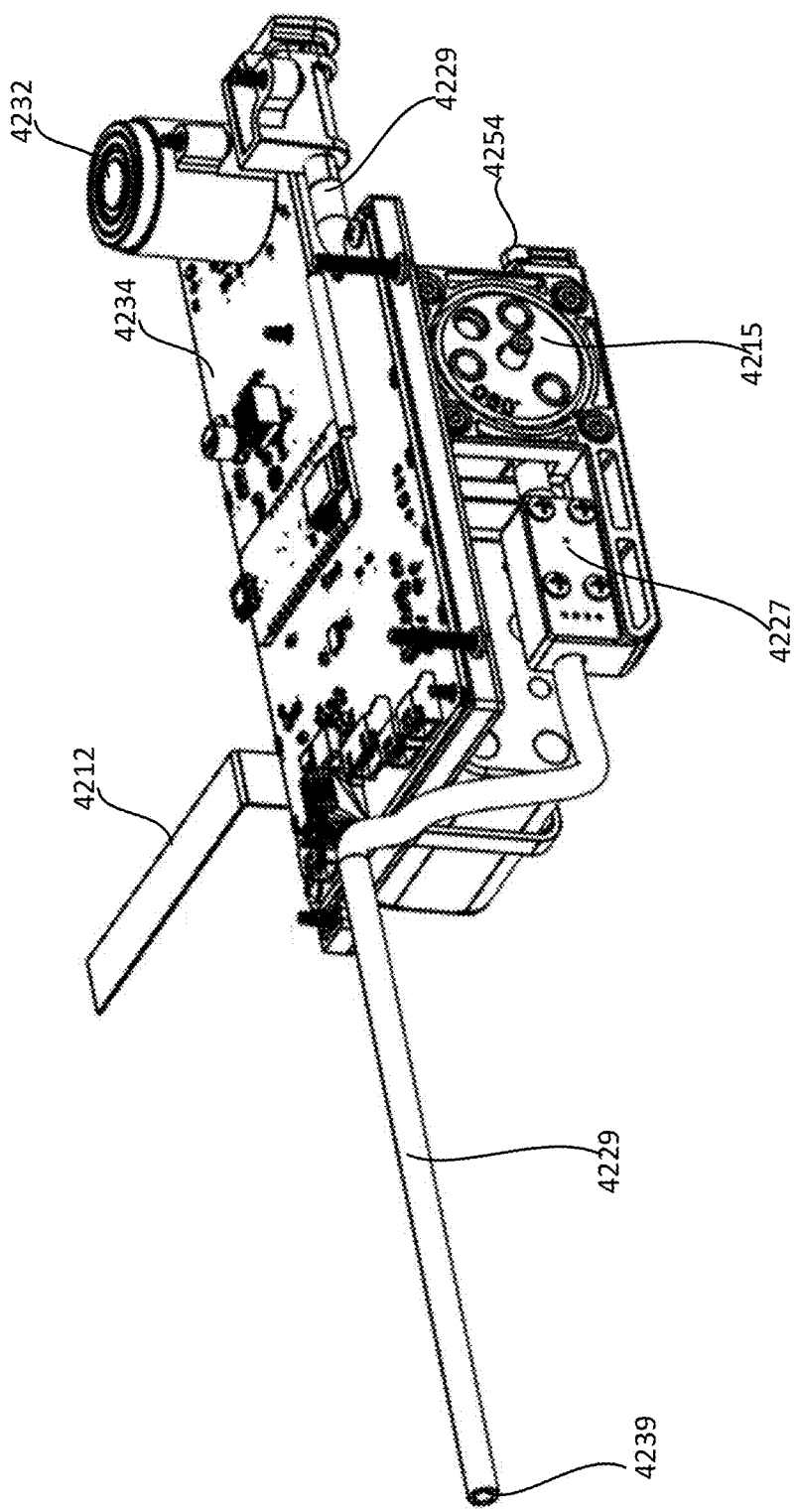
FIG. 29A is a perspective side view on an opposite of the pump assembly shown in FIG. 27 with the pump housing removed for illustration purposes.
Figure 29D:
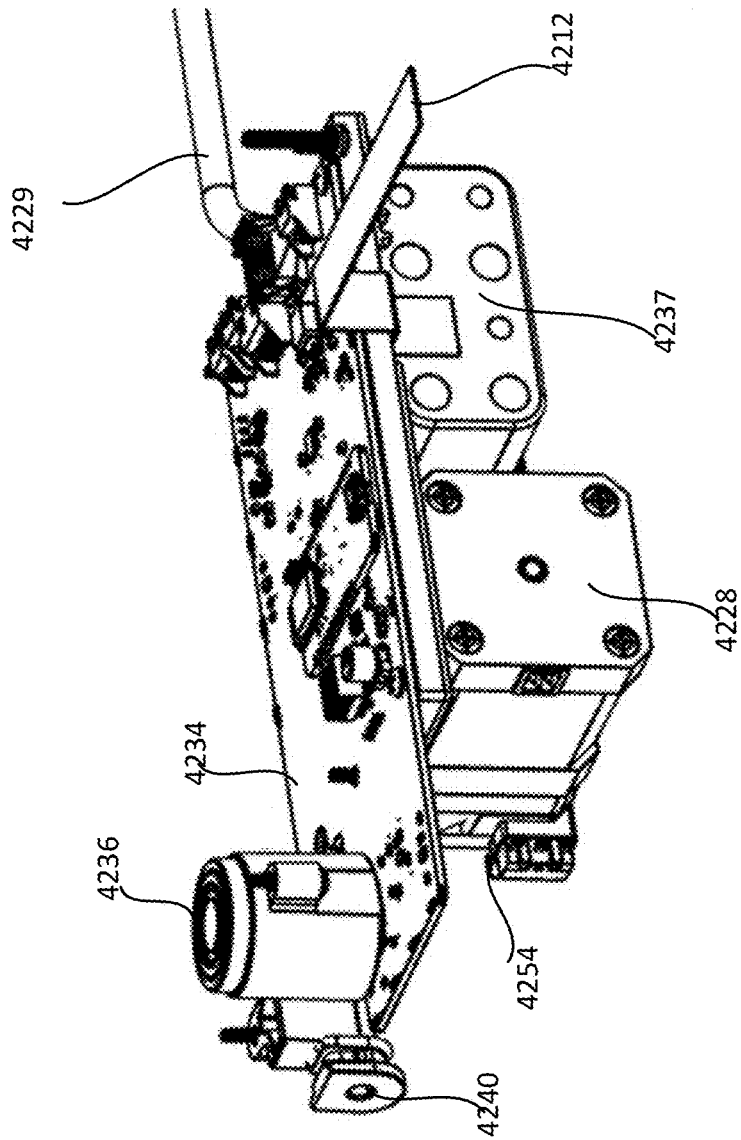
FIG. 29D is a side perspective view of the pump assembly of FIG. 26 showing an opposite side of the pump assembly.
Figure 30A:
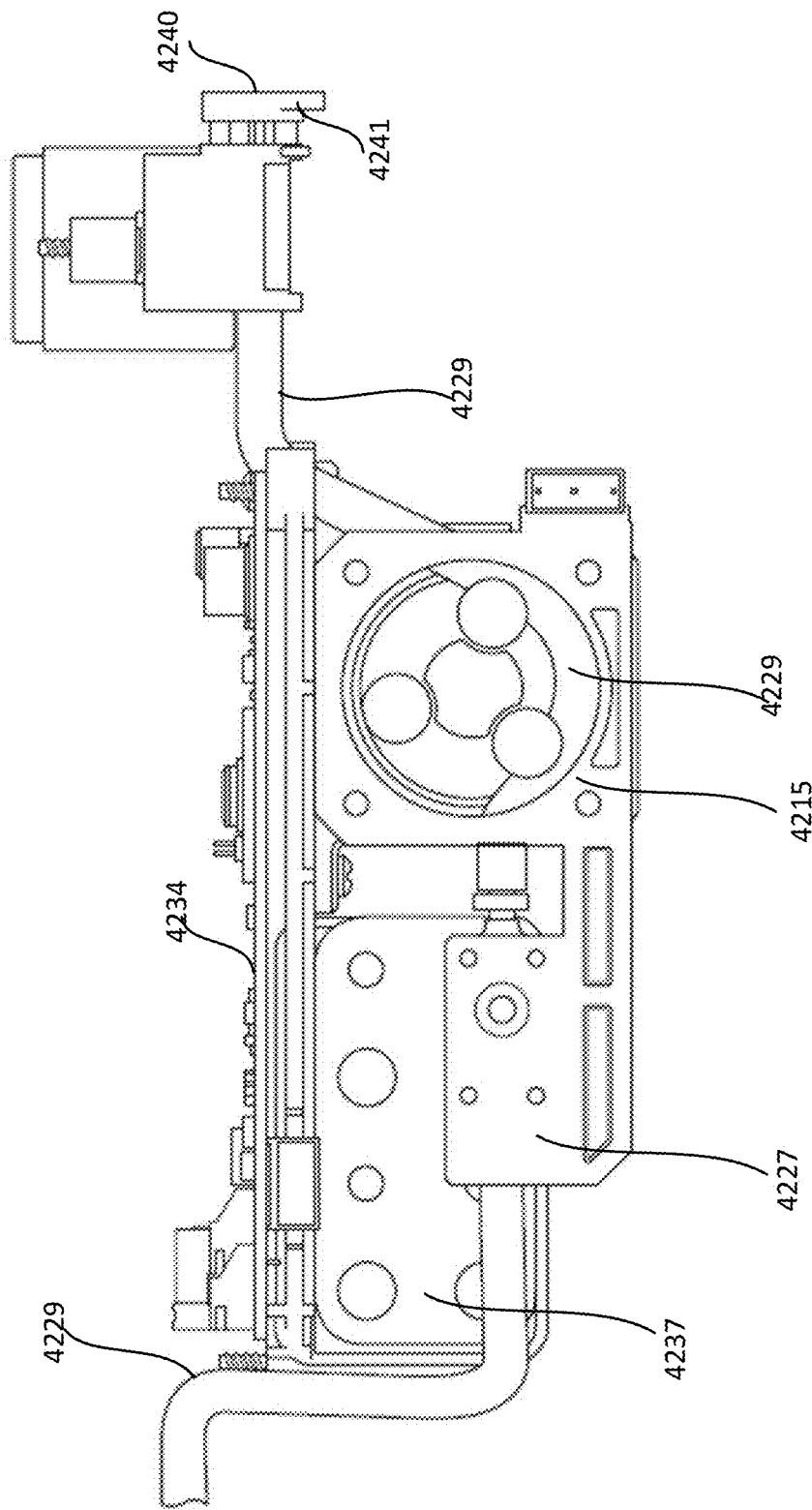
FIGS. 30A and 30B are a front cross-sectional view taken along line 30-30 in FIG. 27 and a front perspective view, respectively, of the pump assembly of FIG. 27.
Figure 30B:
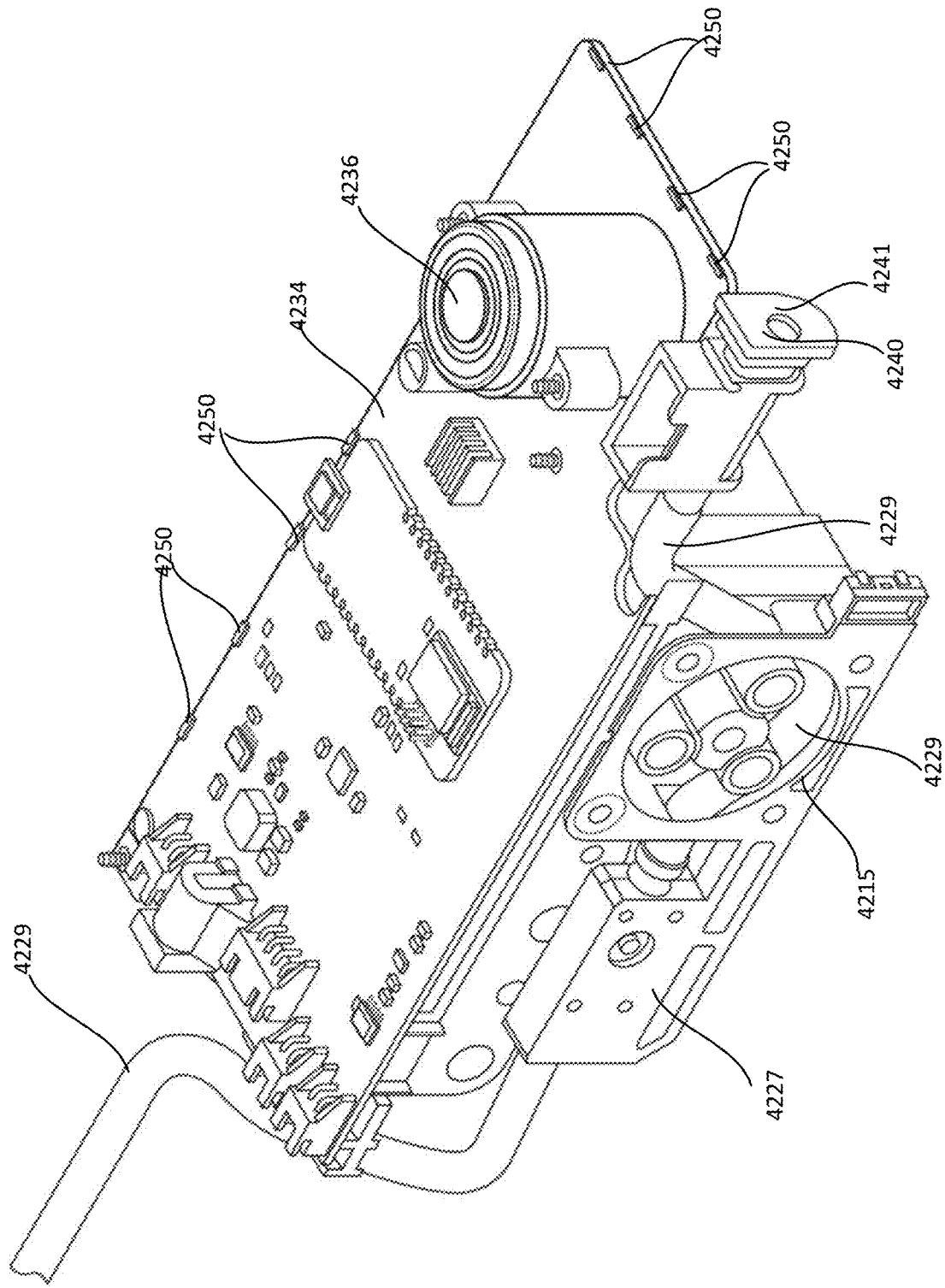
Figure 31:
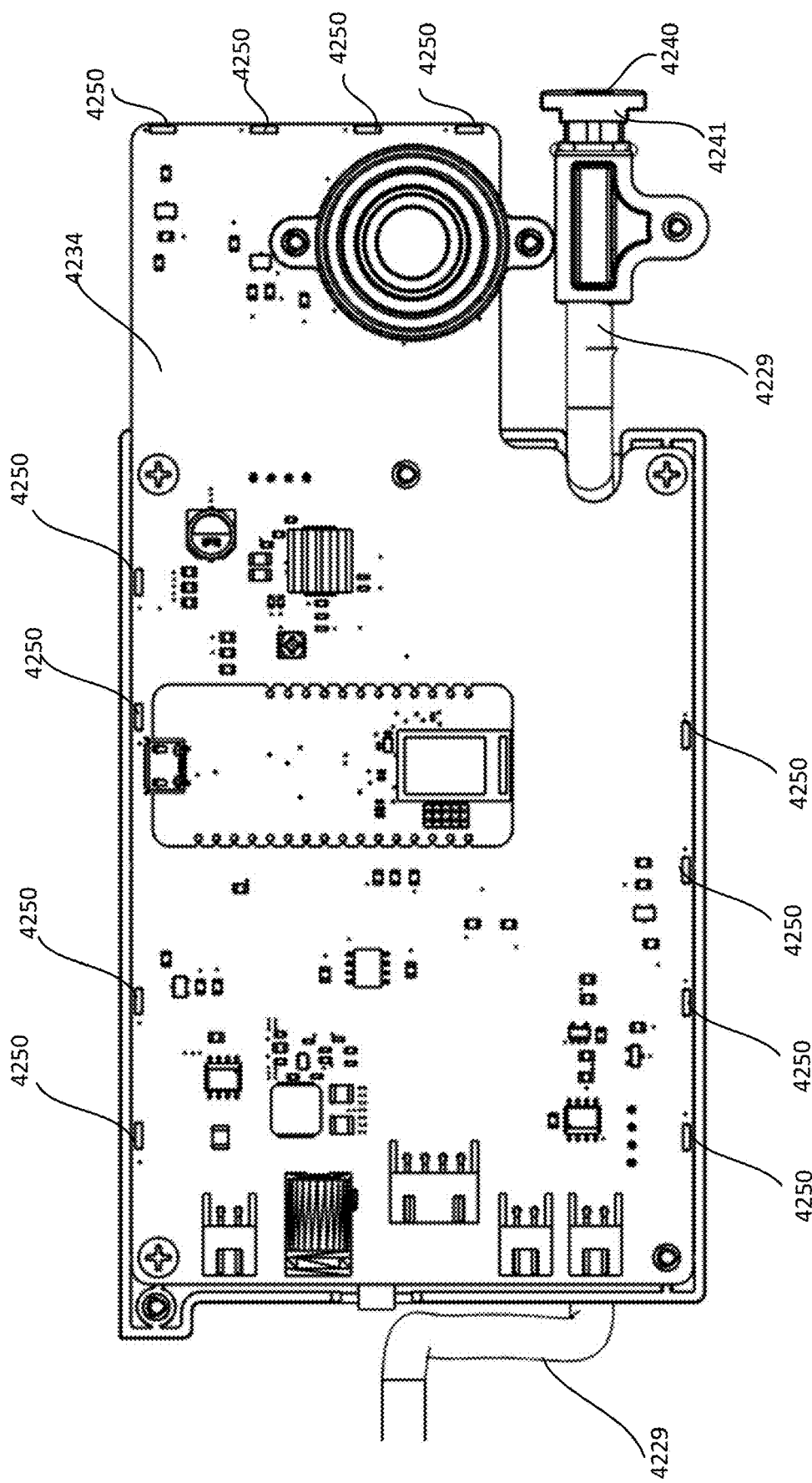
FIG. 31 is a top view of the pump assembly of FIG. 27.

The aspiration tube 4229 includes the outlet port 4240 on one end and an inlet port 4239 on an opposite end (see FIG. 29A). As shown, for example, in FIGS. 29A-30B. the aspiration tube 4229 extends from the outlet port 4240 on the tube support portion 4241, through the pump 4215, through a portion of the sensor 4227 and out an opening in the housing 4100. The catheter coupler 4230 is coupled to and in fluid communication with the inlet port 4239. The catheter coupler 4230 can be removably coupled to the catheter to be used in a thrombectomy procedure. As shown in FIGS. 29B and 29C, the catheter coupler 4230 includes a luer type coupling mechanism 4231 that is coupled to an adapter 4233. The adapter allows for the system 4000 to be coupled to different catheters (e.g., catheters with different diameters, different wall thickness, etc.). In use, a catheter is coupled to the system 4000 via the catheter coupler 4230, inserted into a blood vessel and used to remove an object (e.g., blood clot) from the blood vessel according to any of the methods described herein. The pump 4215 is actuated to provide cyclic and/or constant aspiration pressures as described herein to macerate the object and draw the macerated object into the catheter, through the inlet port 4239, through the aspiration tube 4229, and out through the outlet port 4240 and into the waste volume 4132. As described above, the clot retainer 4134 captures and filters larger biological material such as portions of a blood clot, and blood and other biological material passes through the clot retainer 4134 and into the waste volume 4132.

Figure 14C:
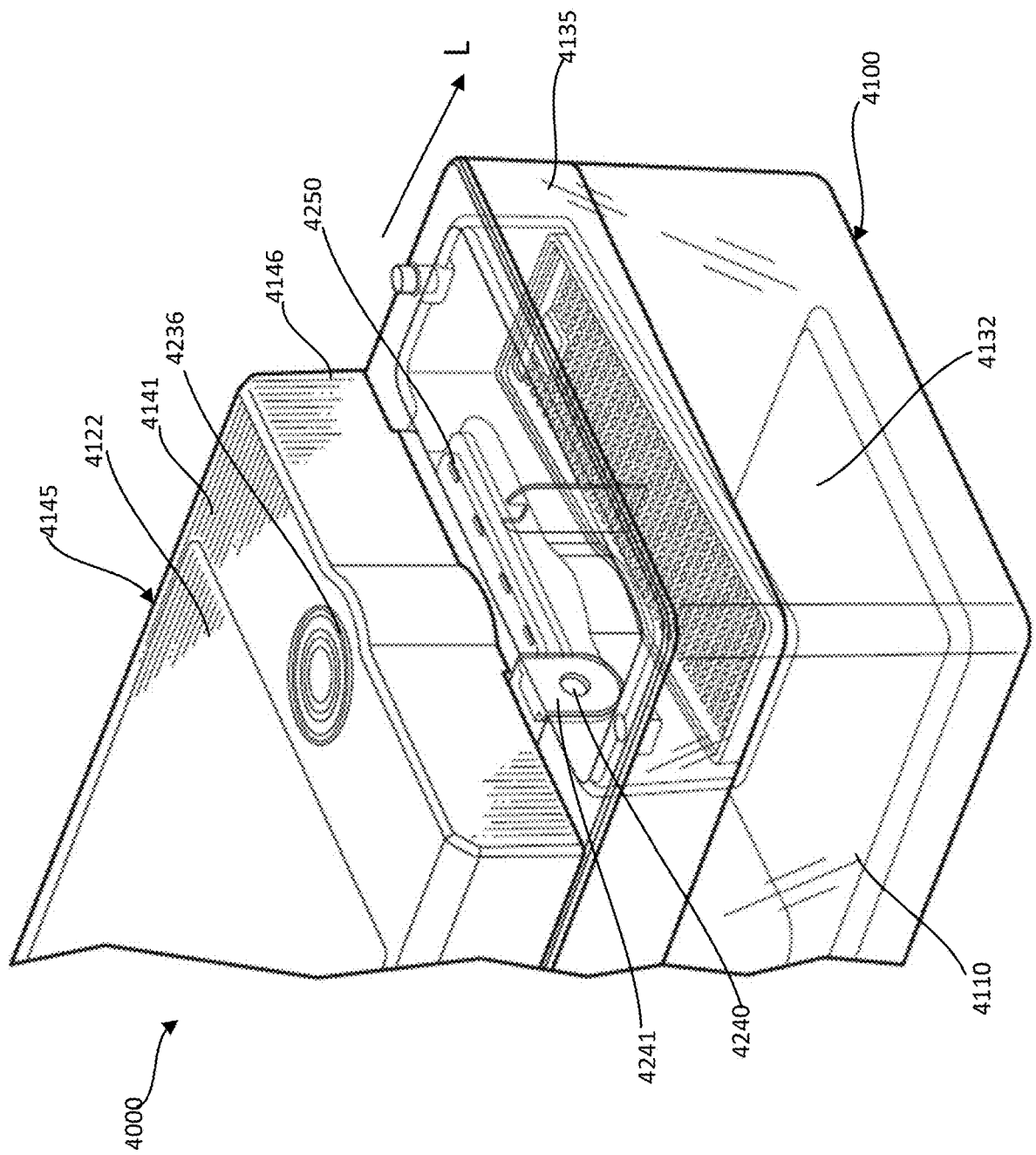
FIG. 14C is an enlarged perspective end view of a portion of the thrombectomy pump system of FIG. 7.
Figure 14D:
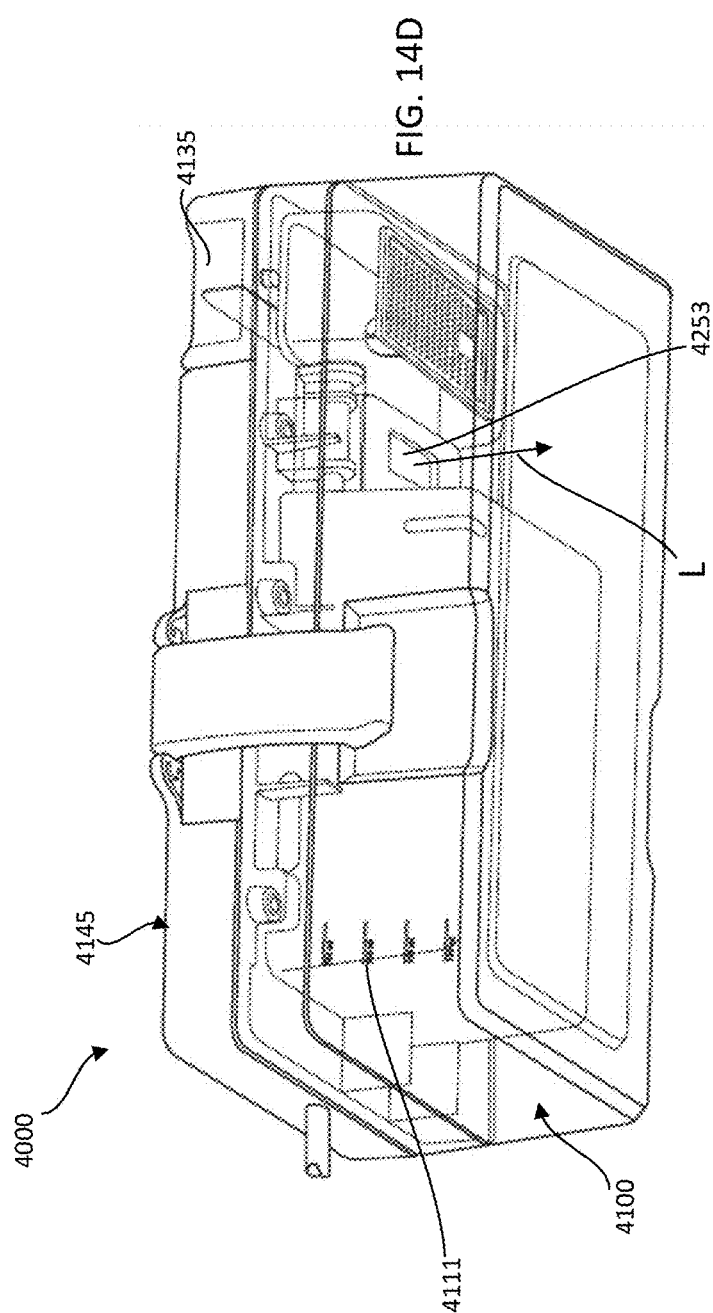
FIG. 14D and FIG. 14E are a bottom perspective view and a side view, respectively, of the thrombectomy pump system of FIG. 7 illustrating a direction of illumination of lights.
Figure 14E:
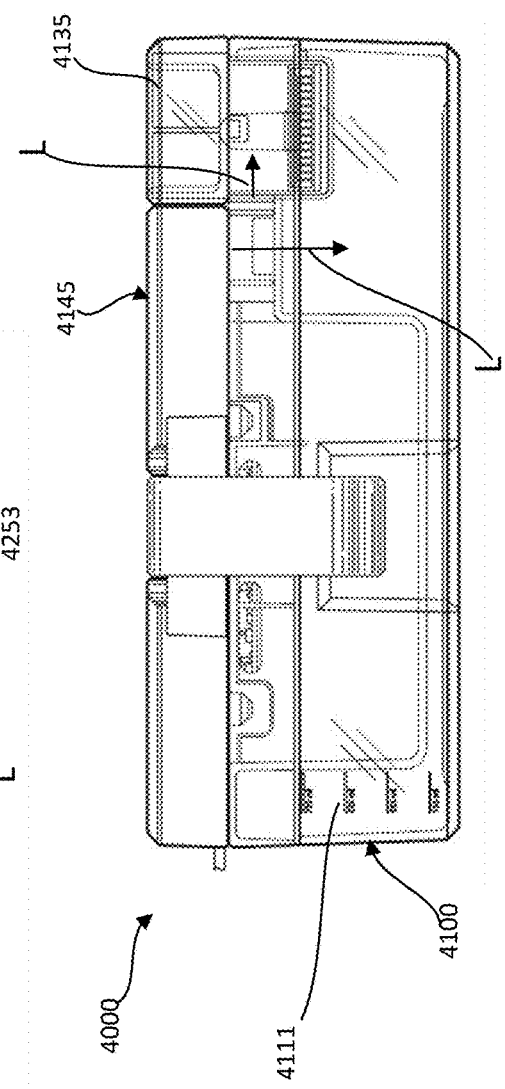
Figure 14F:
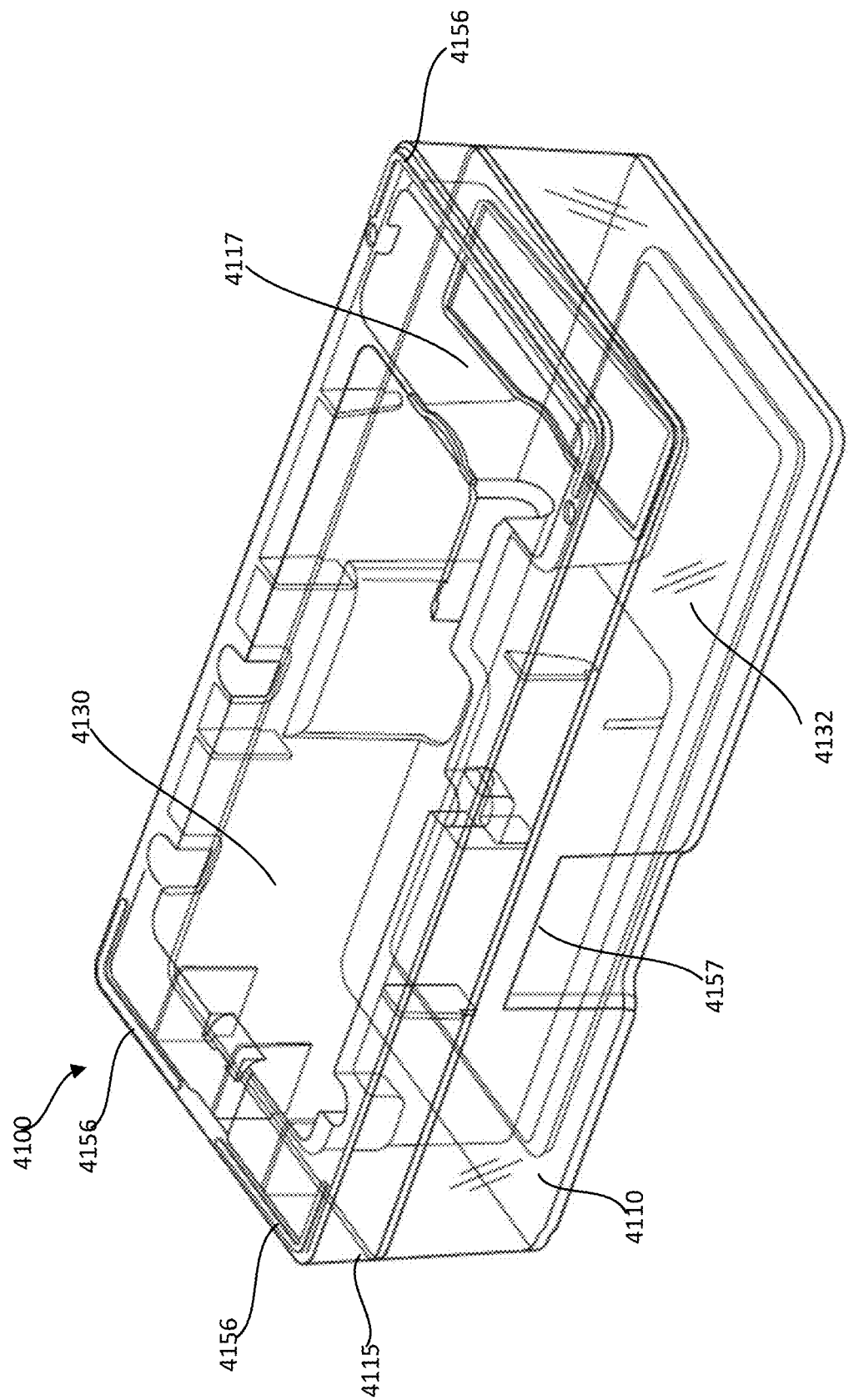
FIG. 14F is a side perspective view of a housing assembly of the thrombectomy pump system of FIG. 7.
Figure 15:
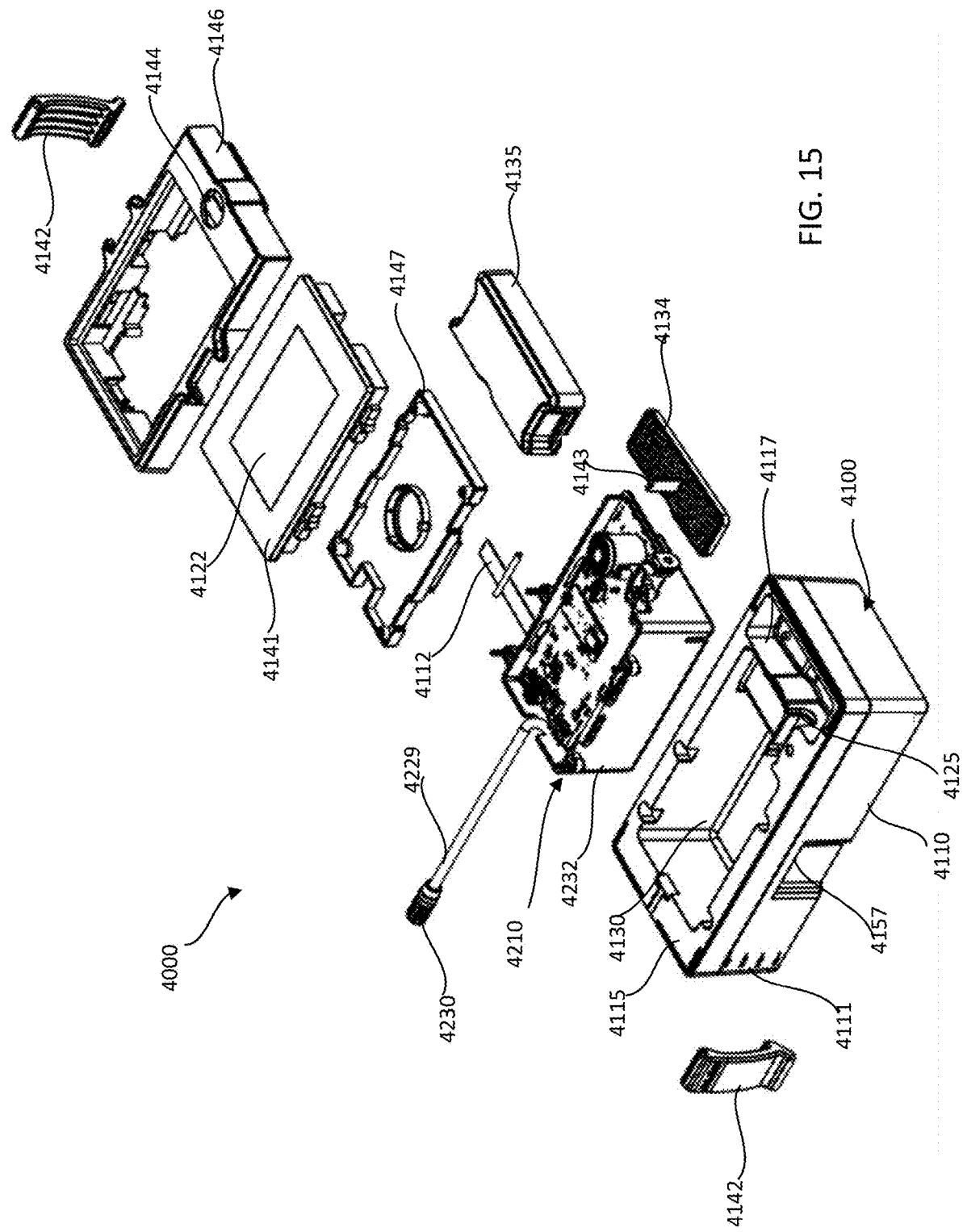
FIG. 15 is a partial exploded view of the thrombectomy pump system of FIG. 7.
Figure 16:
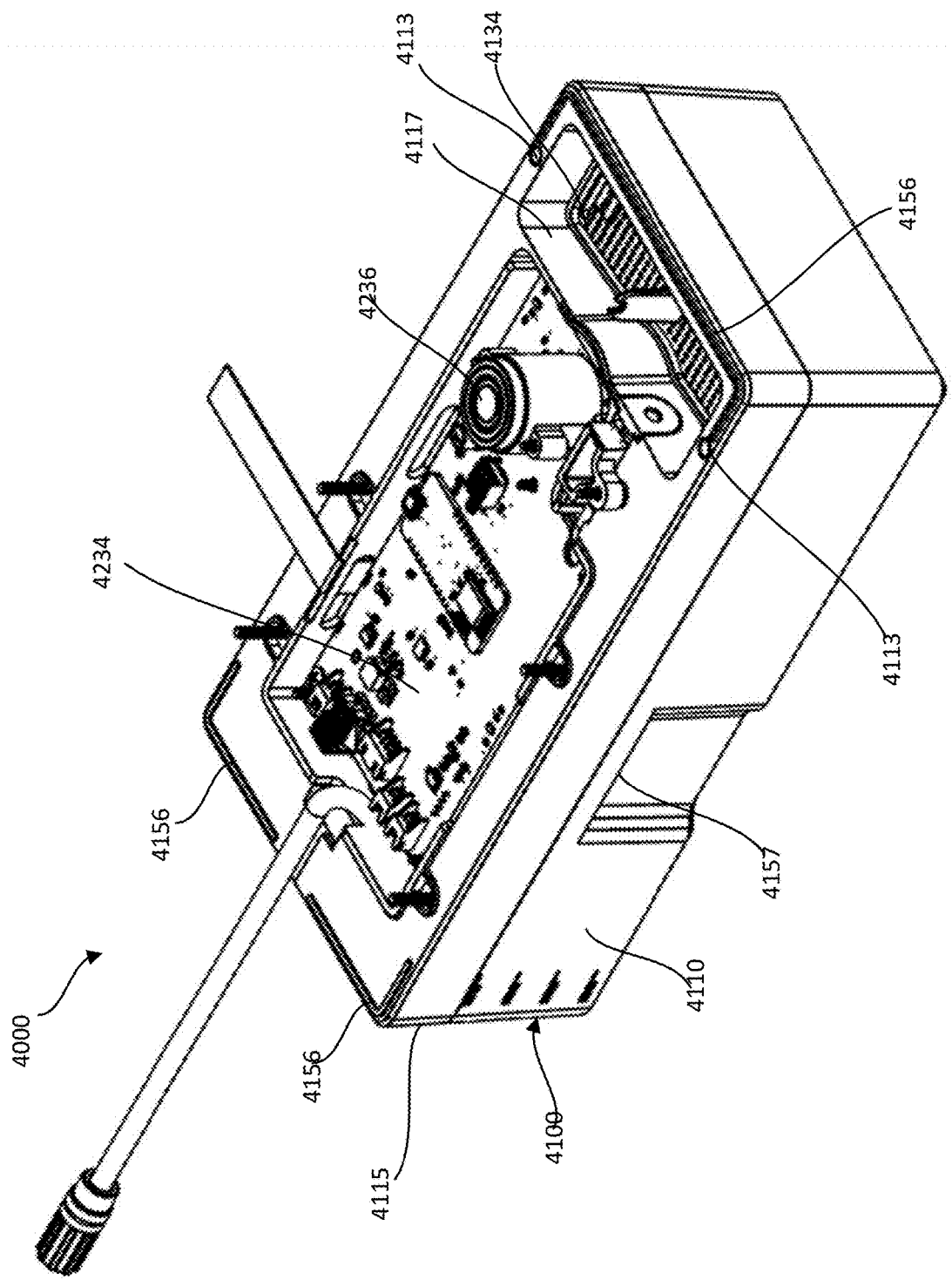
FIG. 16 is a front perspective view of the thrombectomy pump system of FIG. 7 shown with the cover assembly and lid removed for illustration purposes.
Figure 17:
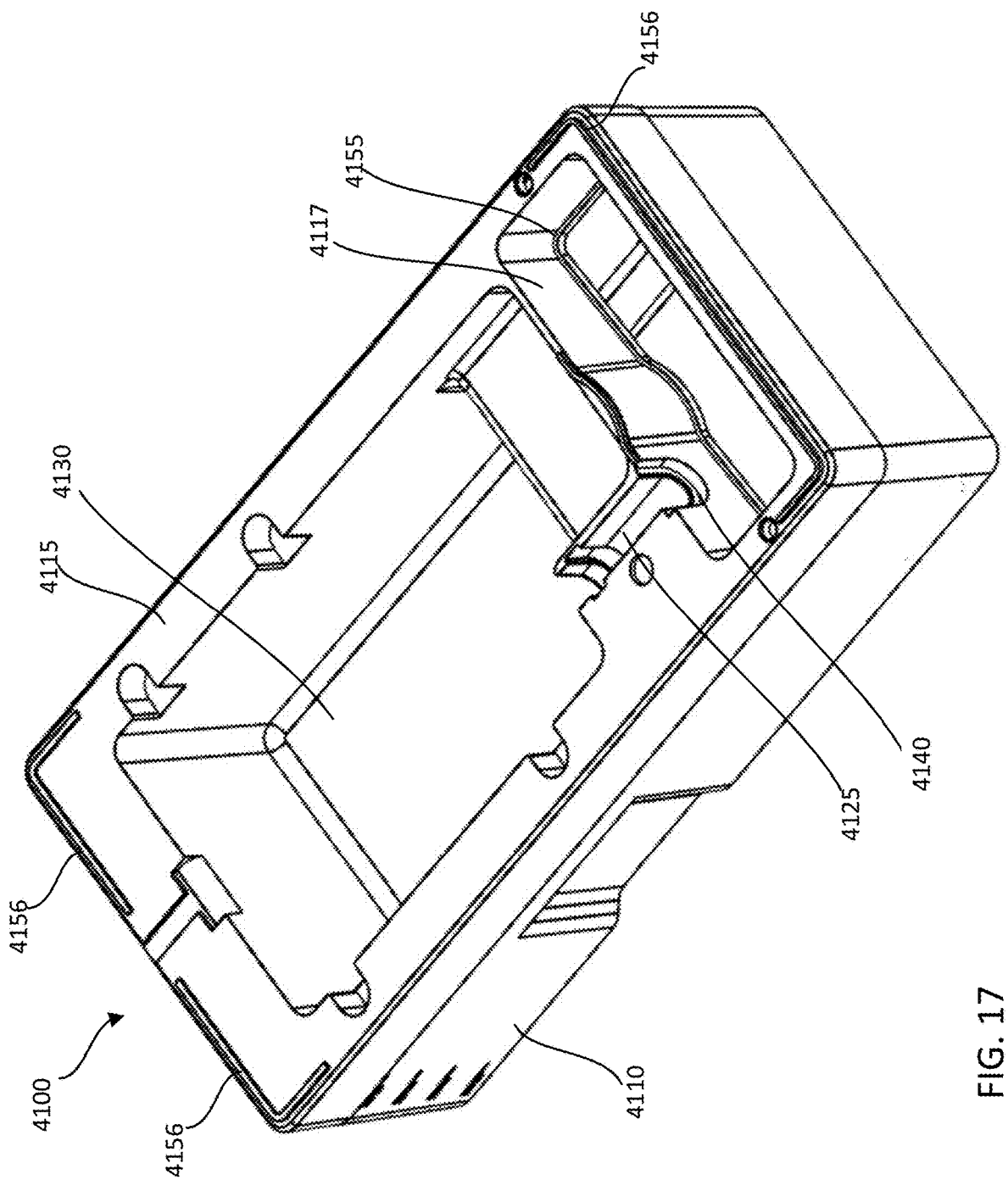
FIG. 17 is a front perspective view of the housing of the thrombectomy pump system of FIG. 7.
Figure 18:
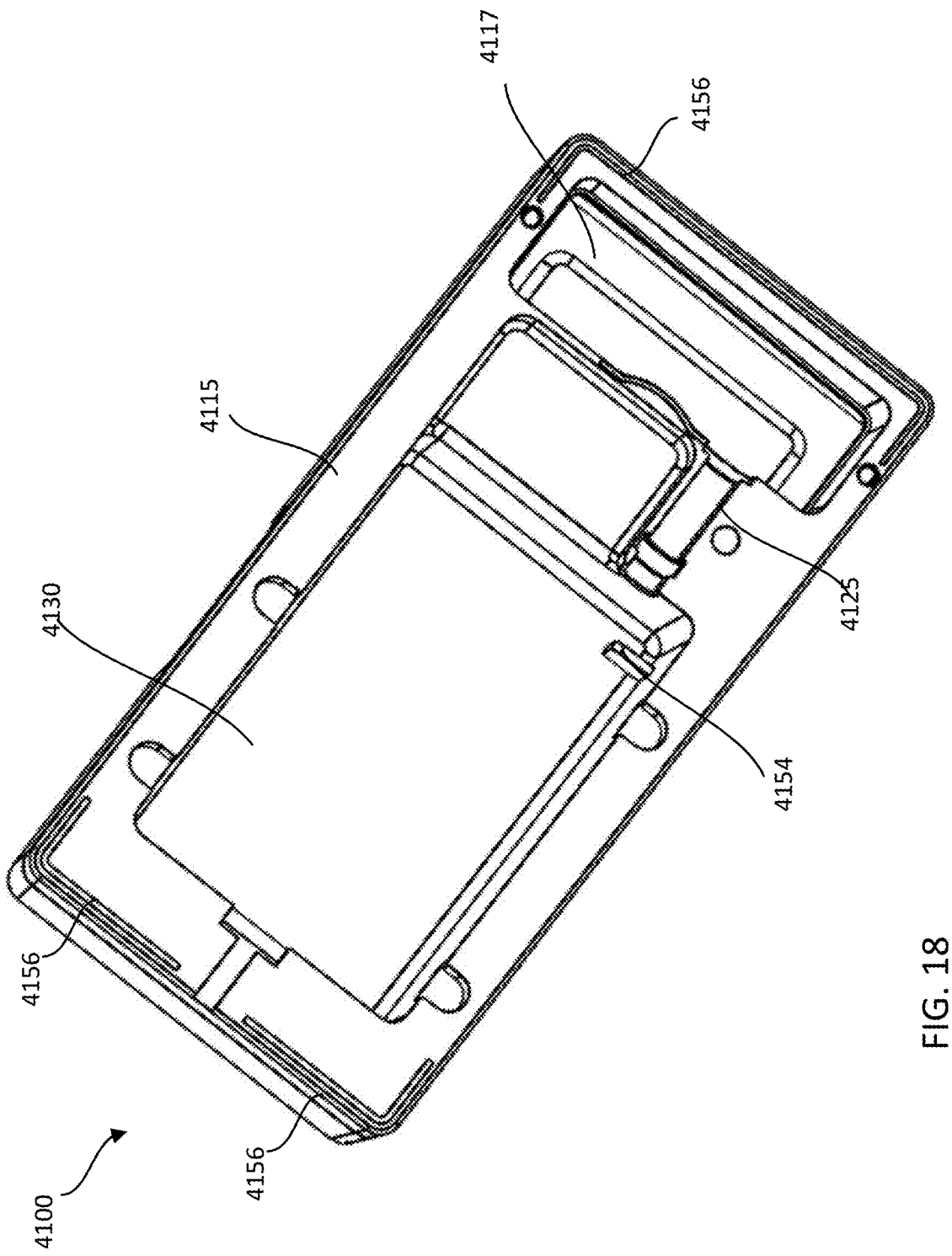
FIG. 18 is a top perspective view of the housing of FIG. 17.

To aid in the visual inspection of the contents of the waste volume 4132 during a procedure, multiple lights 4250 are provided on the pump assembly 4210 to provide illumination into the waste volume 4132. The lights 4250 can be, for example, LED lights. As shown, for example, in FIGS. 27 and 31, the lights 4250 are disposed on the circuit board 4234 and can provide illumination through openings 4252 (see FIG. 26) in the pump housing 4232 and through the transparent walls of the first housing portion 4115 defining the pump cavity 4130. As shown in FIGS. 14A and 14B, the lights 4250 can illuminate through the openings 4252 in the direction of arrows L outwardly into the waste volume 4132. As shown in FIGS. 14C and 14E, the lights 4250 can illuminate into the clot cavity 4117 of the waste volume 4132 in the direction of arrow L. As shown in FIGS. 14D and 14E, the lights 4250 can illuminate down through a window 4253 in the pump housing 4232 as shown by arrow L. In some embodiments, for example, if the first housing portion 4115 wall of the pump cavity 4130 is not transparent, corresponding windows can be provided in the wall of the first housing portion 4115 positioned aligned with the openings 4252 to provide illumination into the waste volume 4132.

The system 4000 also provides an automatic shut off feature configured to power off the system 4000 when the pump assembly 4210 is removed from the housing 4100. More specifically, the pump housing 4232 defines a slot 4253 (see FIG. 26) and the pump assembly 4210 includes a switch 4254 (see FIGS. 27 and 28) that engages a protrusion 4154 (see FIG. 18) of the housing 4100 that extends into the pump cavity 4130 and through the slot 4253. When the pump assembly 4210 is removed from the housing 4100, the protrusion 4154 disengages the switch 4254 which sends a signal to the controller to shut off the system 4000. In some embodiments, the automatic shut off can be configured to actuate immediately upon receipt of the signal. In some embodiments, the automatic shut off can be configured to actuate after a preselected time has passed since the pump assembly 4210 has been removed from the housing 4100.

In some embodiments, the controller (and any of the modules therein) can, in response to the switch 4254 being actuated, send a notification to the display 4122 or to output components of the system. The notification can be, for example, a series of flashing lights from the lights 4250, a message output by the display 4122 or an audio output from a speaker of the system. In some embodiments, the notification can include a countdown timer (e.g., a visual timer from the display 4122 or an audible timer) to alert the surgeon that the system will soon shutdown. In this manner, the surgeon can inspect or remove the contents from the waste volume 4132 before the system shuts down. After the elapsed time, the system will shut down.

In some embodiments, the system 4000 (and any of the systems described herein) can be configured to shut down after a predetermined time. In this manner, the system 4000 can be configured for only a single use and can prevent second (or other unauthorized) uses. For example, because the system is powered by the battery pack 4237, if the system is activated but then not promptly used, the battery power may diminish during storage and therefore not retain sufficient power to complete a desired procedure. Accordingly, in some embodiments, after the battery pull tab 4212 is removed the controller can be configured to shut down the system after a predetermined time period. The controller can produce a set of notifications to the user as the end of the predetermined time period nears (e.g., the 10-minute, 5-minute, and 1-minute times before the end of operation). The notifications can be any suitable type as described herein (e.g., visual warnings on the screen, a series of flashing lights from the canister lights, and audio queues to alert the surgeon).

Figure 32:
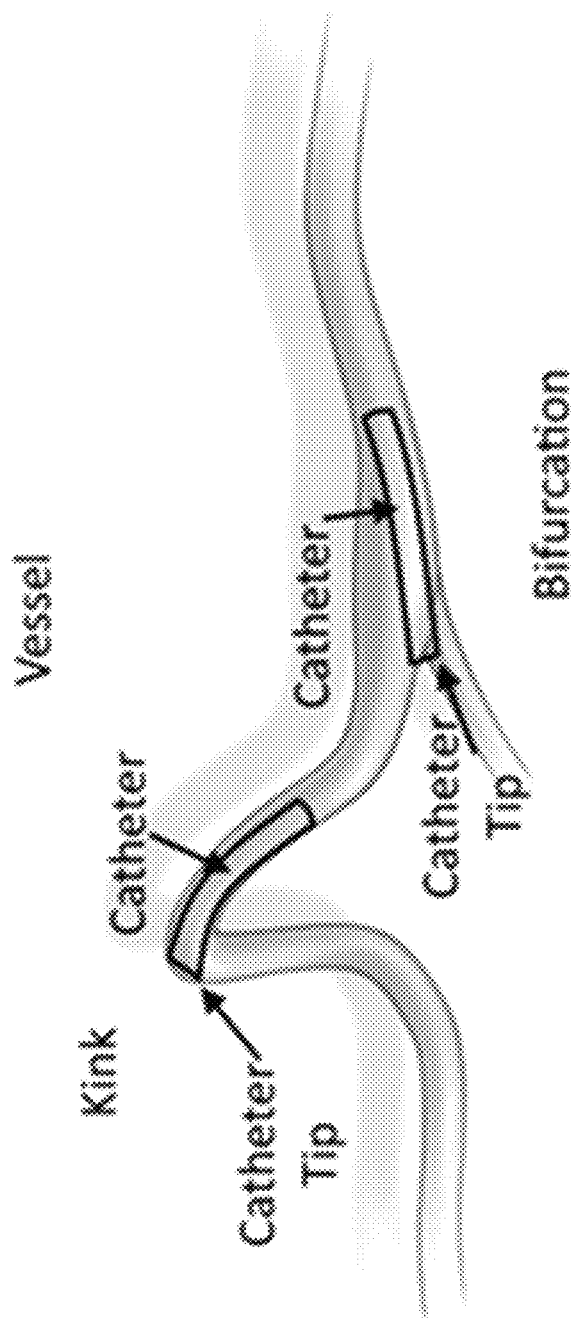
FIG. 32 is a schematic illustration showing a condition where a catheter tip is in contact with a vessel side wall.

During a clot extraction procedure, the catheter is introduced into the vessel while aspirating. FIG. 32 is a schematic illustration showing two cases where the catheter tip may contact the vessel side wall: A) contact occurring at a kink and B) contact occurring when the catheter encounters a bifurcation within the vessel. If the tip of the catheter is in close proximity to or contact with the wall of the vessel, the obstruction at the catheter tip may cause the catheter pressure to drop, which can cause the controller to operate the pump in the Smart Mode (i.e., pressure cycling). In some embodiments, any of the systems described herein can be configured to detect when the catheter tip may be in proximity to a vessel side wall and prompt the user to take corrective action. In this manner, the system can provide guidance to the user to avoid undesired aspiration when the catheter tip may be in contact with the vessel side wall. Thus, the systems and methods described herein can reduce the likelihood of damage to (e.g., perforation of) the vasculature.

Testing of a system (e.g., a system similar to the system 4000) has shown that the catheter pressure signature when the catheter tip is in proximity to or contact with a vessel wall exhibits different behaviors than when the system is macerating and aspirating a clot. Specifically, when the catheter tip contacts a vessel side wall, the occlusion at the catheter tip will result in the pump cycling between increasing and decreasing the pressure in the catheter. During the infusion portion of the cycle, the catheter tip will be separated from the vessel side wall, thus substantially clearing the obstruction. At this point, the algorithm will transition to the aspiration portion of the cycle, which can cause a repetitive behavior in the pressure cycle. Said another way, a ratio of the time during the aspiration portion of the cycle and the infusion portion of the cycle is substantially constant. In contrast, when a clot is being macerated, the pressure cycle will not be as uniform due to the change in the structural consistency of the clot.

Figure 33A:
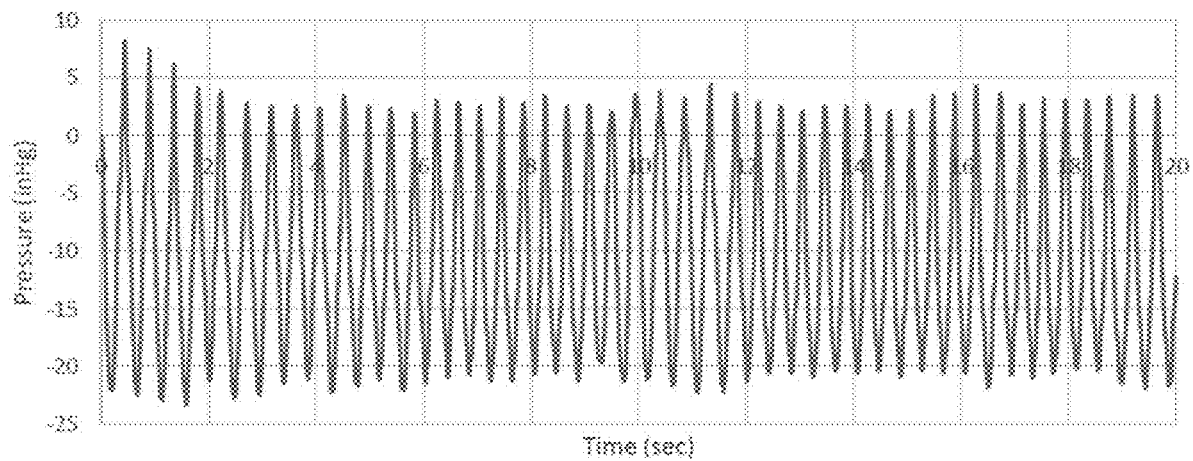
FIG. 33A is a plot showing catheter pressure as a function of time for an example operation when the catheter is in proximity to a vessel side wall.
Figure 33B:
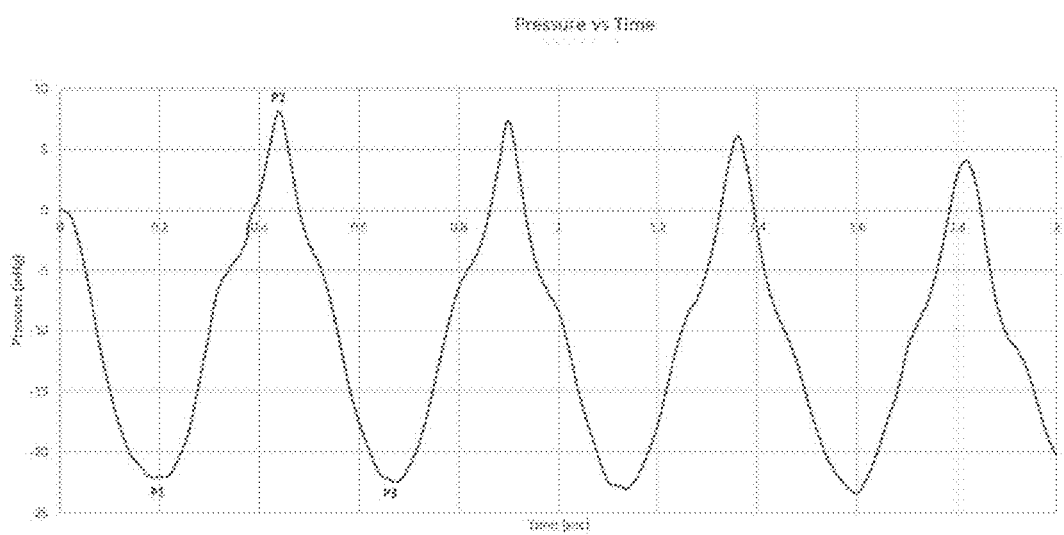
FIG. 33B is an enlarged view of a portion of the plot of FIG. 33A.
Figure 33C:
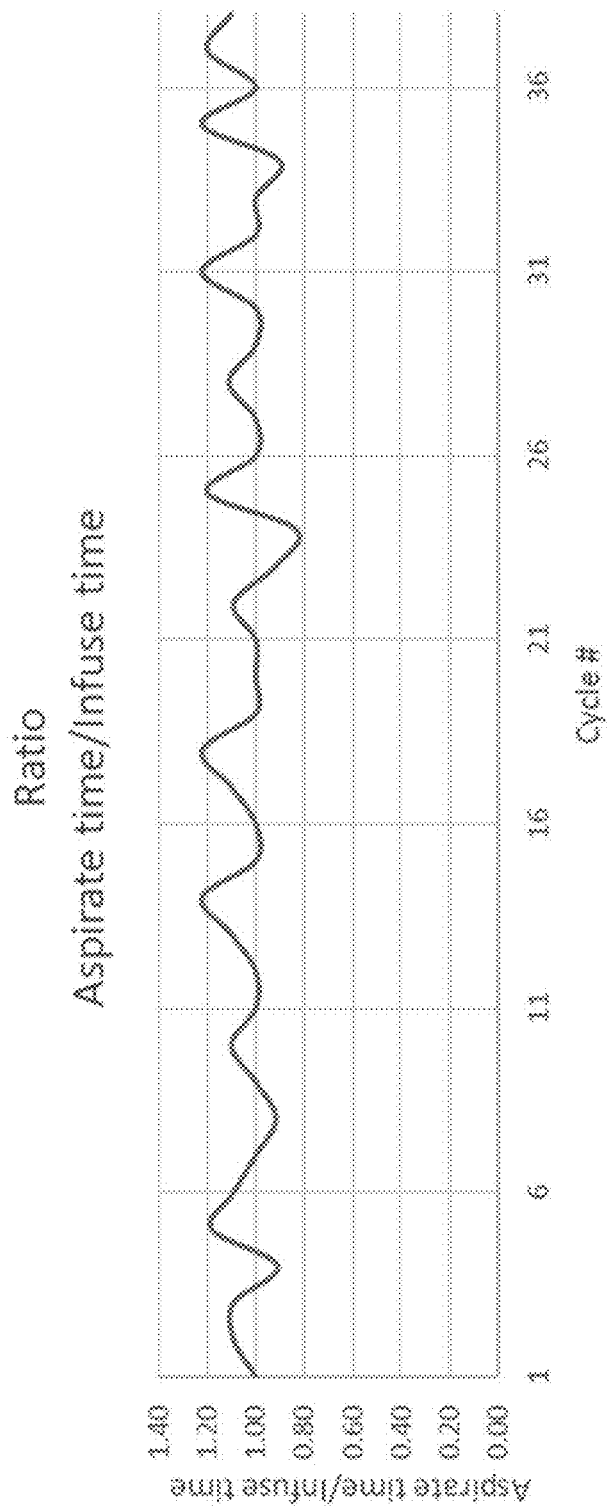
FIG. 33C is a plot showing a ratio of the aspiration time to the infusion time for an example operation when the catheter is in proximity to a vessel side wall.

FIGS. 33A and 33B are plots illustrating the catheter pressure as a function of time when the catheter tip is in contact with a vessel side wall. FIG. 33A shows the pressure cycle over about 40 cycles (approx. 20 seconds) and FIG. 33B is an enlarged view of only four cycles. As can be seen in the enlarged view, the time during aspiration (e.g., from point P2 to P3; referred to as the aspiration time) is very similar to the time during infusion (e.g., from point P1 to P2; referred to as the infusion time. FIG. 33C is a plot of the ratio of the aspiration time to the infusion time during this procedure. As shown in FIG. 33C, this ratio is substantially constant, which indicates that the catheter tip may be in contact with a vessel side wall and not macerating a clot.

Figure 33D:
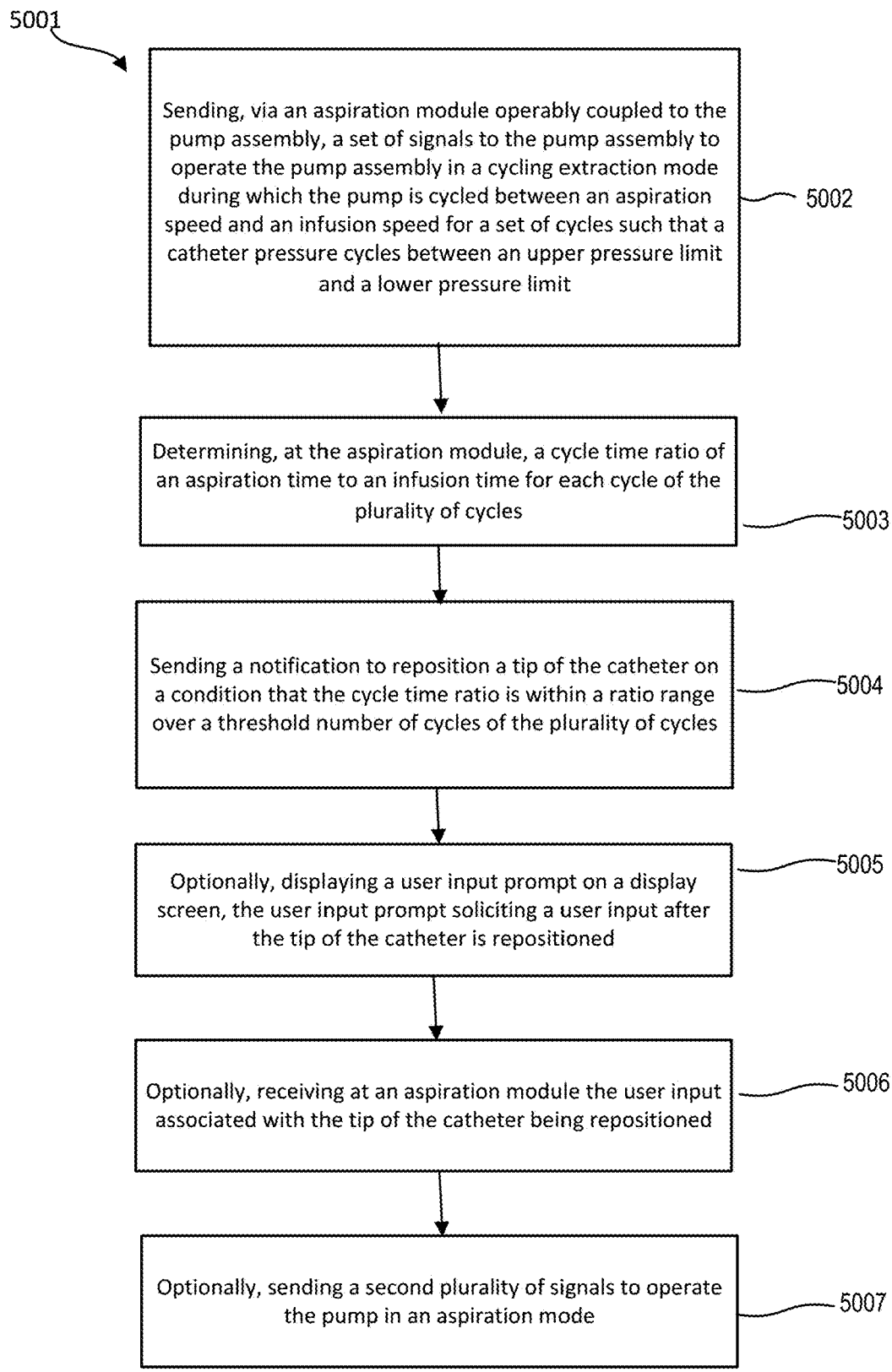
FIG. 33D is a flowchart illustrating a method of using a thrombectomy pump system to remove a thrombus from a body vessel according to an embodiment.

Because a clot that is not being macerated may exhibit similar pressure cycling behavior to that in some embodiments, a method may include producing a notification prompting the surgeon to move the catheter tip slightly. Such notification can supplement any input from angiographic visualization. In this manner, the system 4000 can limit the likelihood of undesired aspiration that could damage the vasculature. For example, FIG. 33D is a flowchart illustrating a method 5001 of removing thrombus from a body lumen via a catheter coupled to a pump assembly that includes a pump. The method can be performed by any of the pump assemblies or systems described herein, including the system 4000. The method 5001 includes sending, via an aspiration module operably coupled to the pump assembly, a set of signals to the pump assembly to operate the pump assembly in a cycling extraction mode, at 5002. During the extraction mode, the pump is cycled between an aspiration speed and an infusion speed for a set of cycles such that a catheter pressure cycles between an upper pressure limit and a lower pressure limit. Similarly stated, the pump is operated in the Smart Mode, which causes the catheter pressure to cycle between Pupper and Plower. At 5003, a cycle time ratio of an aspiration time to an infusion time for each cycle of the set of cycles is determined. The cycle time ratio can be determined at the aspiration module of the controller or any other suitable portion of the controller. At 5004, a notification to reposition a tip of the catheter is sent on a condition that the cycle time ratio is within a ratio range over a threshold number of cycles of the plurality of cycles. The notification can be any suitable format as described herein. For example, in some embodiments the notification can be sent to the display 4122. By prompting the user to reposition or move the catheter, if the catheter tip is in contact with a vessel wall, the repositioning may allow the surgeon to efficiently continue with the procedure.

In some embodiments, the ratio range is between 0.8 and 1.2. In some embodiments, the ratio range is between 0.9 and 1.1. In some embodiments, the aspiration speed is different than the infusion speed aspiration speed and the ratio range is based at least in part on a difference between the aspiration speed and the infusion speed. For example, if the infusion speed is only 90% of the aspiration speed, the ratio range may not be centered around 1, but instead may centered above 1 (e.g., the range may be from 0.9 to 1.3). In some embodiments, the threshold number of cycles is at least 20 cycles.

In some embodiments, the notification indicates that a tip of the catheter may be in contact with a side wall of the body lumen. For example, the notification may include a graphical depiction illustrating a catheter tip in contact with an animated side wall. The method can optionally include, at 5005, displaying a user input prompt on a display screen. The user input prompt solicits a user input after the tip of the catheter is repositioned. In this manner, the system can receive an indication that the catheter tip has been moved to reset the operation. For example, in some embodiments, the method can optionally include receiving at an aspiration module the user input associated with the tip of the catheter being repositioned, at 5007. The a second set of signals can then be sent to operate the pump in an aspiration mode, at 5008.

Figure 34:
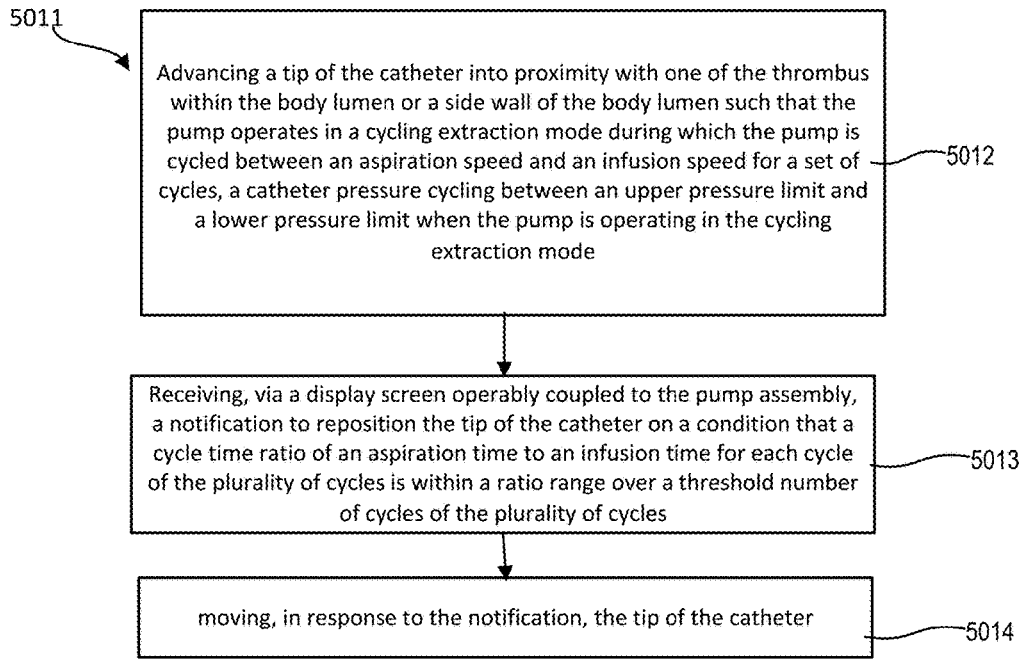
FIG. 34 is a flowchart illustrating a method of using a thrombectomy pump system to remove a thrombus from a body vessel according to an embodiment.

FIG. 34 is a flowchart illustrating a method 5011 of removing a thrombus from a body lumen via a catheter coupled to a pump assembly that includes a pump. The method can be performed by any of the pump assemblies or systems described herein, including the system 4000. The method 5011 includes advancing a tip of the catheter into proximity with one of the thrombus within the body lumen or a side wall of the body lumen such that the pump operates in a cycling extraction mode during which the pump is cycled between an aspiration speed and an infusion speed for a set of cycles, at 5012. A catheter pressure cycles between an upper pressure limit and a lower pressure limit when the pump is operating in the cycling extraction mode. At 5013, a notification to reposition the tip of the catheter is received on a condition that a cycle time ratio of an aspiration time to an infusion time for each cycle of the plurality of cycles is within a ratio range over a threshold number of cycles of the set of cycles. The method includes moving, in response to the notification, the tip of the catheter, at 5014.

Figure 35A:
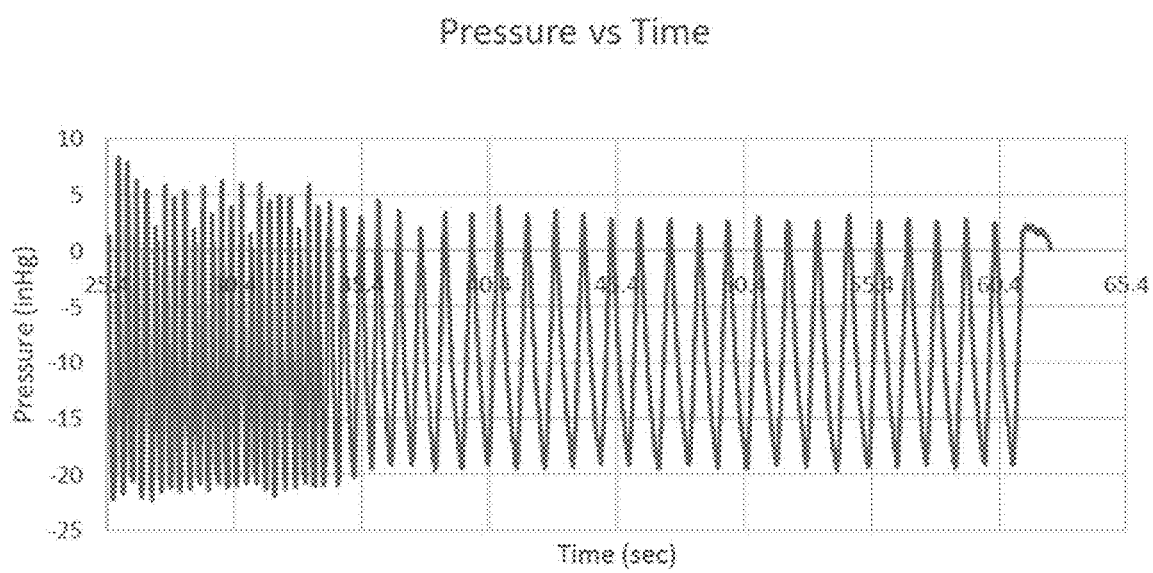
FIG. 35A is a plot showing catheter pressure as a function of time for an example operation when the catheter has air in the line.

During a clot extraction procedure, in certain circumstances air may be introduced into the system, which can reduce the efficacy of clot removal. In such situations it may be necessary to checked the system connections for leaks or otherwise reprime the catheter. Testing of a system (e.g., a system similar to the system 4000) has shown that the catheter pressure signature when the catheter tip is in proximity to or contact with a vessel wall exhibits different behaviors than when air is introduced into the system. Specifically, when the catheter line contains air, the period of cycling will increase (i.e., the cycles will occur at a lower frequency) even when the pump is operating at the same aspiration speed and infusion speed. FIG. 35A is a plot illustrating the catheter pressure as a function of time when air becomes present in the line. As shown, the cycle period increases when air is present in the line.

Figure 35B:
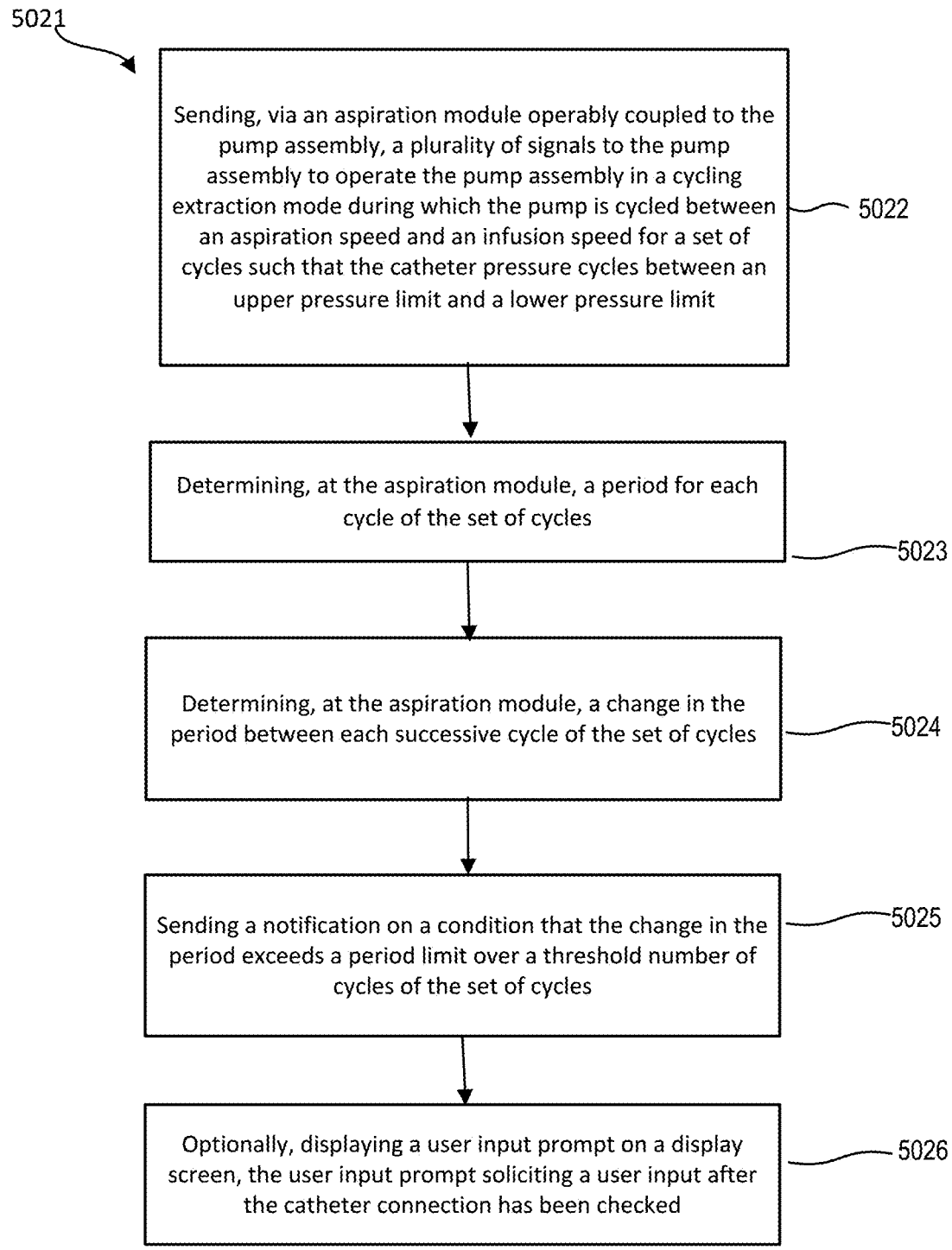
FIG. 35B is a flowchart illustrating a method of detecting air in a thrombectomy pump system during removal of a thrombus from a body vessel according to an embodiment.

FIG. 35B is a flowchart illustrating a method 5021 of removing a thrombus from a body lumen via a catheter coupled to a pump assembly that includes a pump. The method can be performed by any of the pump assemblies or systems described herein, including the system 4000. The method 5021 includes sending, via an aspiration module operably coupled to the pump assembly, a set of signals to the pump assembly to operate the pump assembly in a cycling extraction mode, at 5022. In this mode, the pump is cycled between an aspiration speed and an infusion speed for a set of cycles such that the catheter pressure cycles between an upper pressure limit and a lower pressure limit. At 5023, a period for each cycle of the set of cycles is determined at the aspiration module. A change in the period between each successive cycle of the set of cycles is then determined at the aspiration module, at 5024. The method further includes sending a notification on a condition that the change in the period exceeds a period limit over a threshold number of cycles of the set of cycles, at 5025.

In some embodiments, the notification prompts a user to check a catheter connection to the pump assembly. In such embodiments, the method optionally includes displaying a user input prompt on a display screen, the user input prompt soliciting a user input after the catheter connection has been checked at 5026.

As described herein, in some circumstances the pressure cycling may not be able to macerate the clot for aspiration within a predetermined time period. Specifically, in some circumstances, the thrombus may become plugged within the catheter. In such instances, as described herein, the system 4000 will produce notification to the user providing instructions to withdraw the catheter from the vessel to remove the thrombus. Although this technique is effective for removing the thrombus, it can take additional time to withdraw the catheter. Moreover, if additional thrombus remain in the vessel, the catheter may need to be reinserted to removal all of the blockages. To improve the efficacy of the procedure when the thrombus is removed by withdrawing the catheter, the system 4000 (and any of the systems described herein) can monitor the status of the catheter (and the thrombus plugged therein) during the catheter withdrawal procedure. In this manner, if the plugged state of the thrombus becomes compromised, the user can be notified to stop withdrawing the catheter and take additional actions. For example, if a portion of the thrombus that is plugged within the catheter fragments thereby compromising the plugged state, the system 4000 can produce a notification. Such fragmenting may be caused by the tortuous path of the catheter withdrawal or may also be caused by further maceration (and aspiration) of the thrombus due to the continued aspiration pressure. In this manner, the system 4000 can allow the user to respond rapidly to changes in the plugged state thereby saving valuable time.

Figure 36:
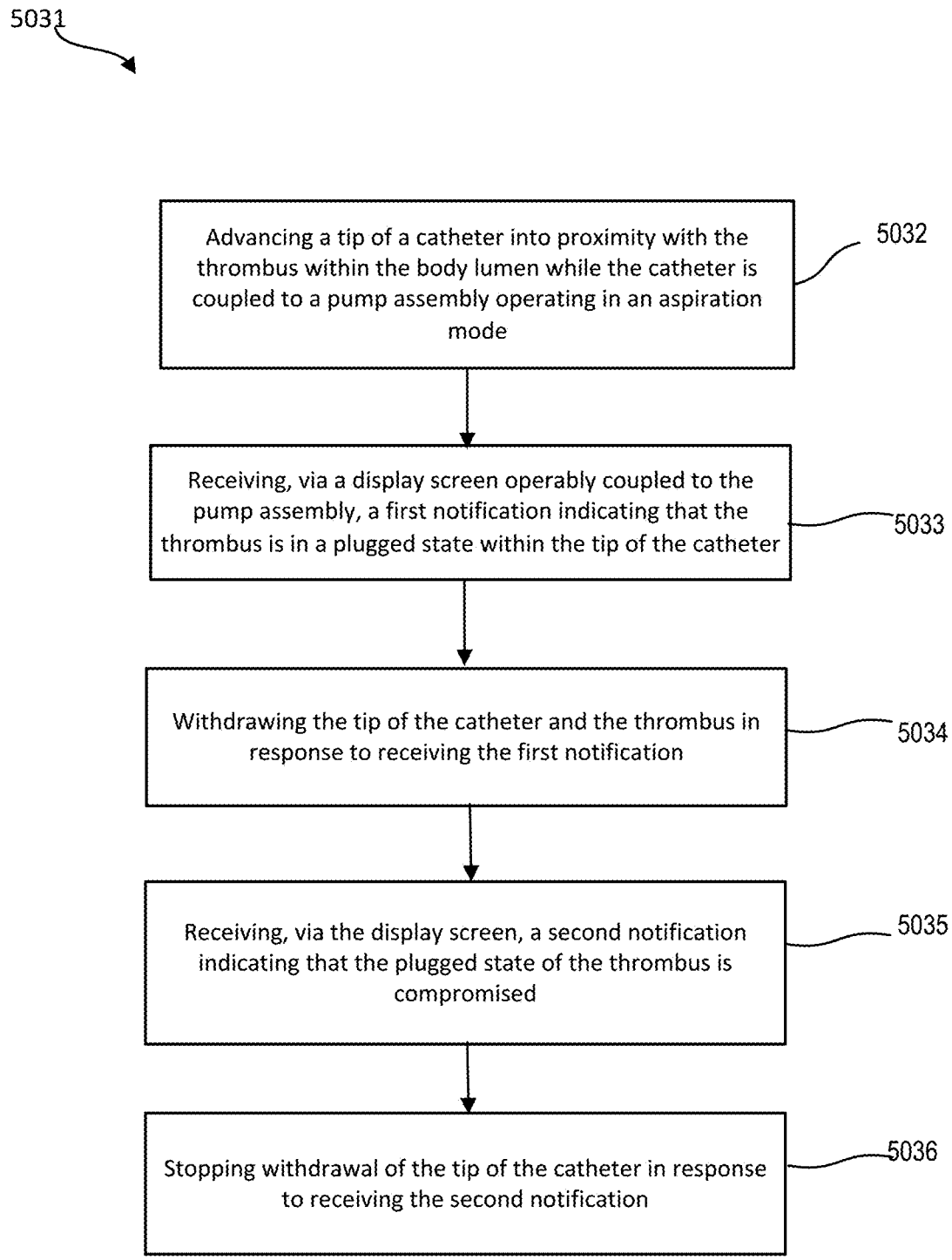
FIG. 36 is a flowchart illustrating a method of removing a thrombus from a body lumen.

FIG. 36 is a flowchart illustrating a method 5031 of removing thrombus from a body lumen. The method can be performed by any of the pump assemblies or systems described herein, including the system 4000. The method 5032 includes advancing a tip of a catheter into proximity with the thrombus within the body lumen while the catheter is coupled to a pump assembly operating in an aspiration mode. At 5033, a first notification indicating that the thrombus is in a plugged state within the tip of the catheter is received at a display screen operably coupled to the pump assembly. At 5034, the tip of the catheter and the thrombus are withdrawn in response to receiving the first notification. At 5035, a second notification indicating that the plugged state of the thrombus is compromised is received at the display screen. At 5036, the withdrawal of the tip of the catheter in response to receiving the second notification is stopped.

Figure 37:
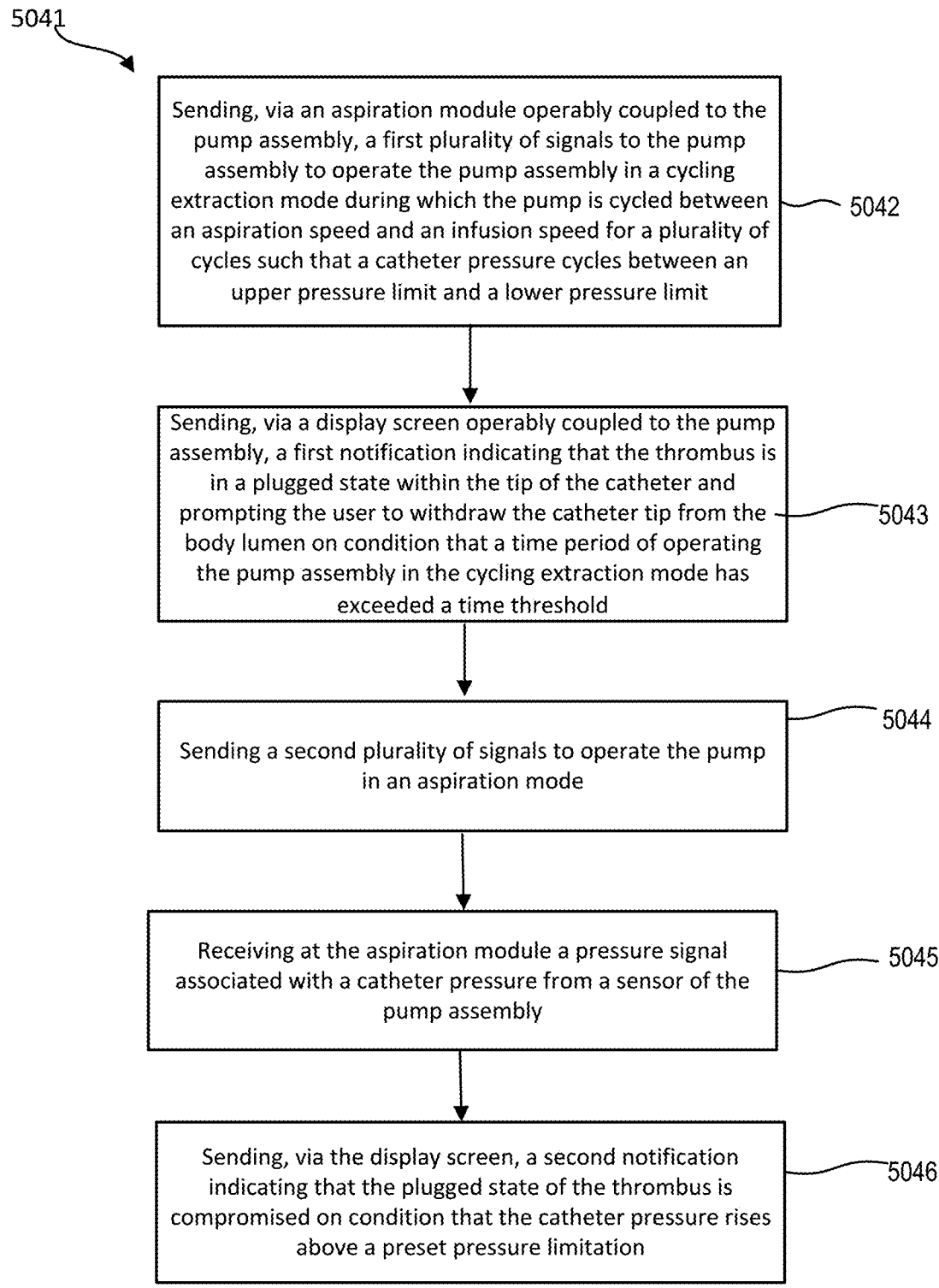
FIG. 37 is a flowchart illustrating a method of removing a thrombus from a body lumen via a catheter coupled to a pump assembly.

FIG. 37 is a flowchart illustrating a method 5041 of removing a thrombus from a body lumen. The method can be performed by any of the pump assemblies or systems described herein, including the system 4000. The method 5041 includes at 5042, sending, via an aspiration module operably coupled to the pump assembly, a first plurality of signals to the pump assembly to operate the pump assembly in a cycling extraction mode during which the pump is cycled between an aspiration speed and an infusion speed for a plurality of cycles such that a catheter pressure cycles between an upper pressure limit and a lower pressure limit. At 5043, a first notification is sent to a display screen operably coupled to the pump assembly, which indicates that the thrombus is in a plugged state within the tip of the catheter, and a user is prompted to withdraw the catheter tip from the body lumen on condition that a time period of operating the pump assembly in the cycling extraction mode has exceeded a time threshold. At 5044, a second plurality of signals to operate the pump in an aspiration mode is sent. At 5045, a pressure signal associated with a catheter pressure is received at the aspiration module from a sensor of the pump assembly. At 5046, on condition that the catheter pressure rises above a preset pressure limitation, a second notification indicating that the plugged state of the thrombus is compromised is sent to the display screen.

Figure 38A:
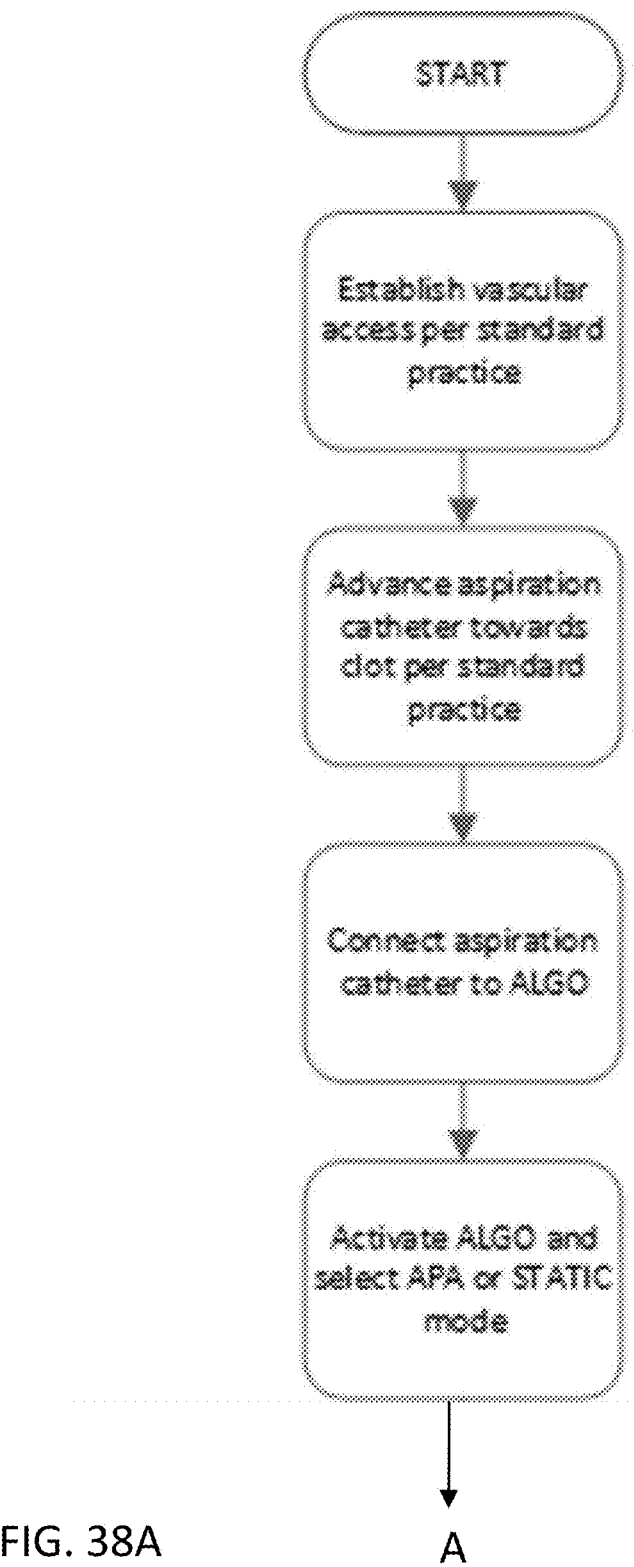
FIGS. 38A and 38B are a flowchart illustrating a method of removing a thrombus from a body lumen.
Figure 38B:
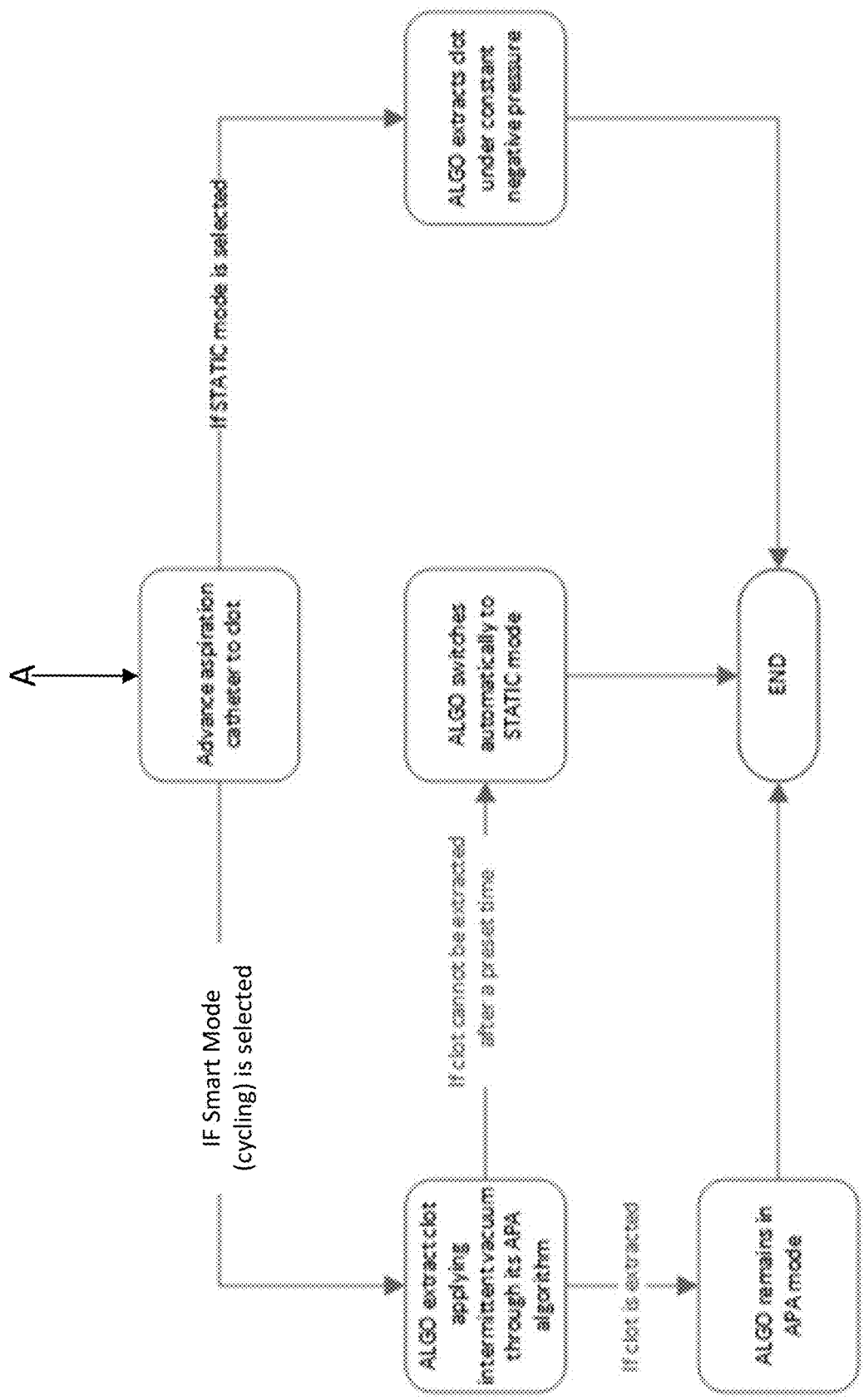

FIGS. 38A and 38B illustrate a flow chart depicting process methodologies from START to END for both Static and Smart modes. Reference to "operational state" is used to describe the pump behavior along a main loop depending on the current flow state discussed above, as controlled by a selected pump algorithm.

Figure 39A:
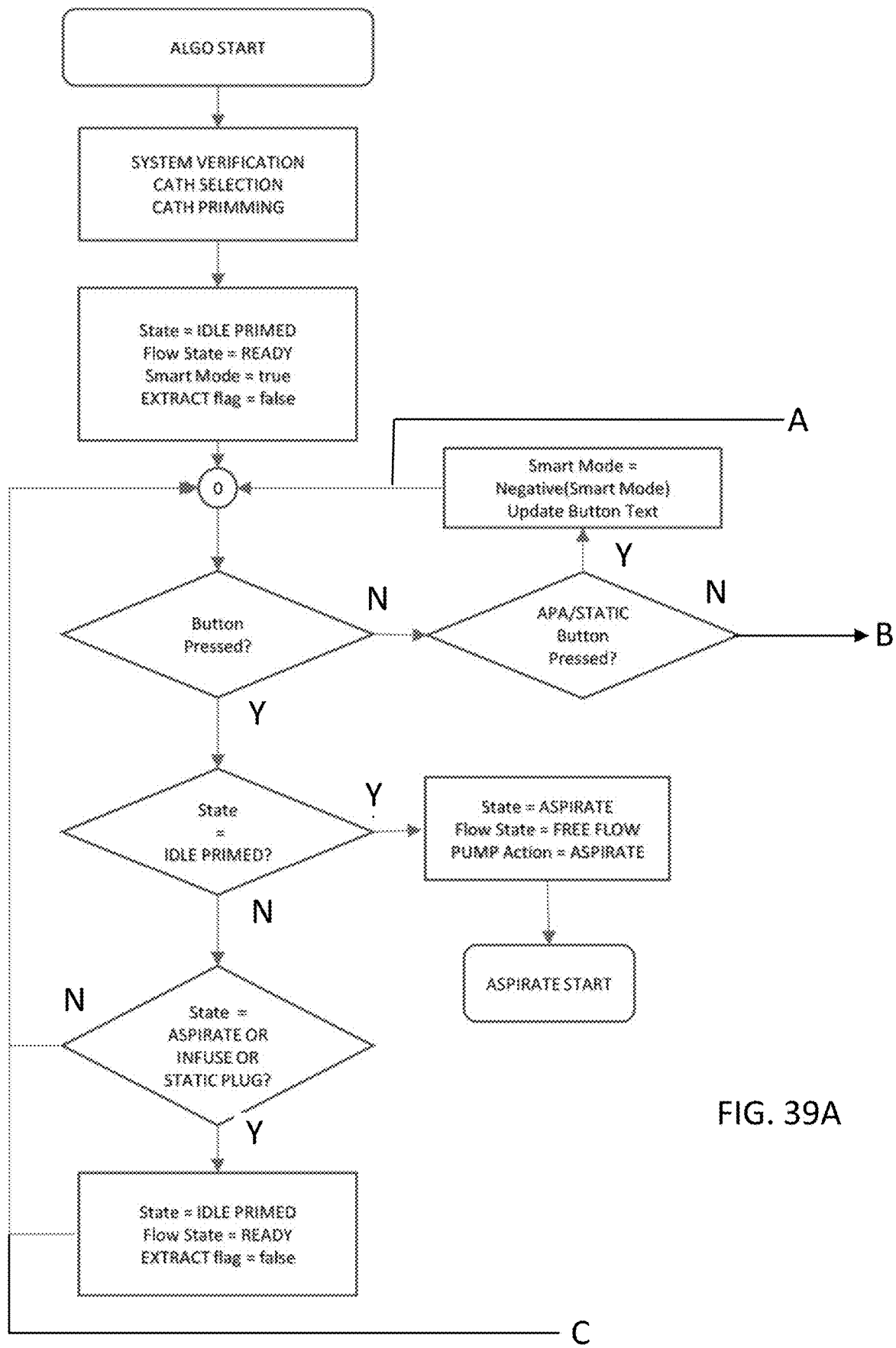
FIGS. 39A and 39B are a flowchart illustrating a method of removing a thrombus from a body lumen.
Figure 39B:
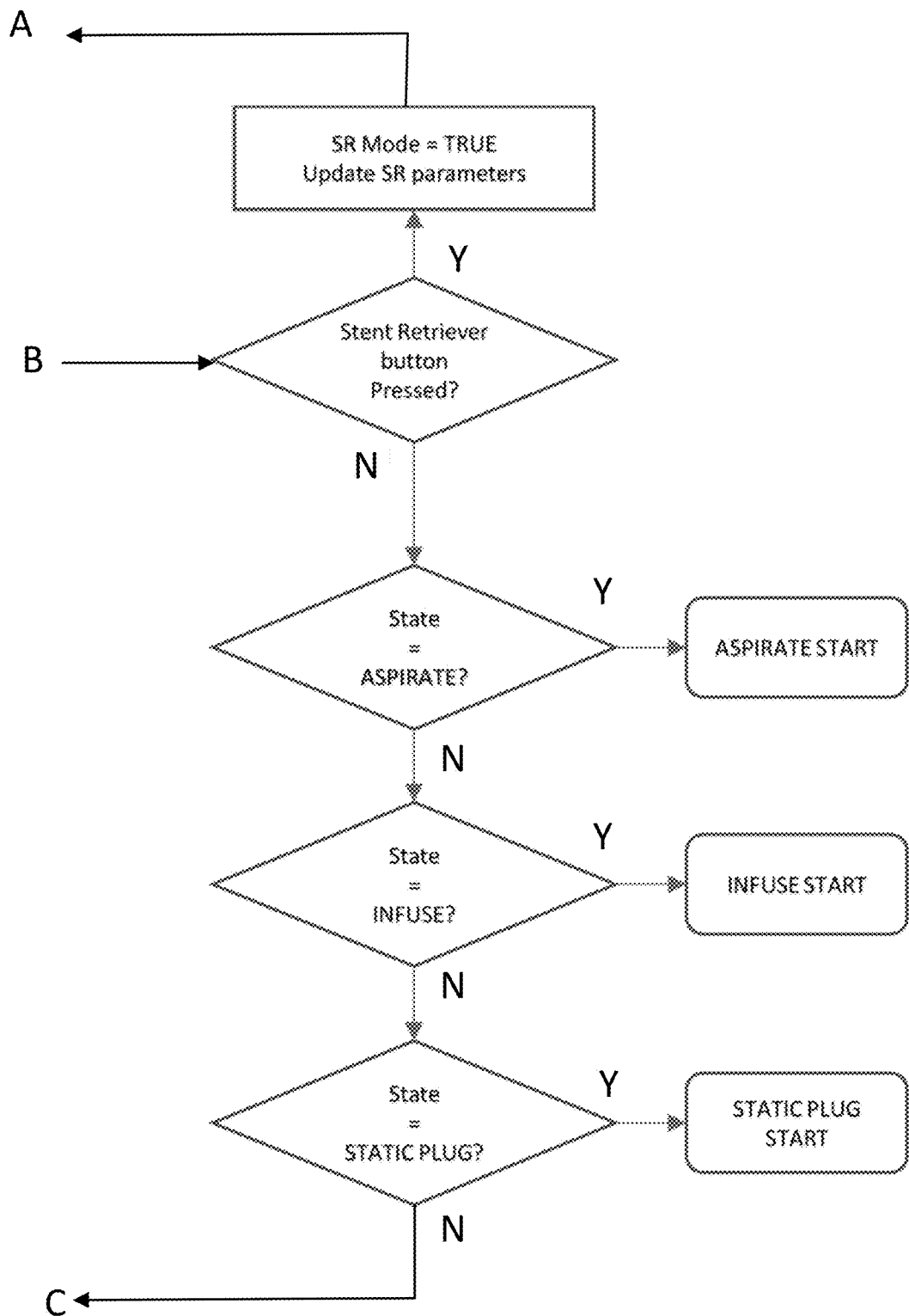

Referring now to FIGS. 39A and 39B, a main control loop is depicted in the illustrated flow chart. The flow chart begins in a start block and terminates in any of a start of ASPIRATE, INFUSE or STATIC PLUG. Each of these selections are depicted as flow charts in FIGS. 40A-41B.

Figure 40A:
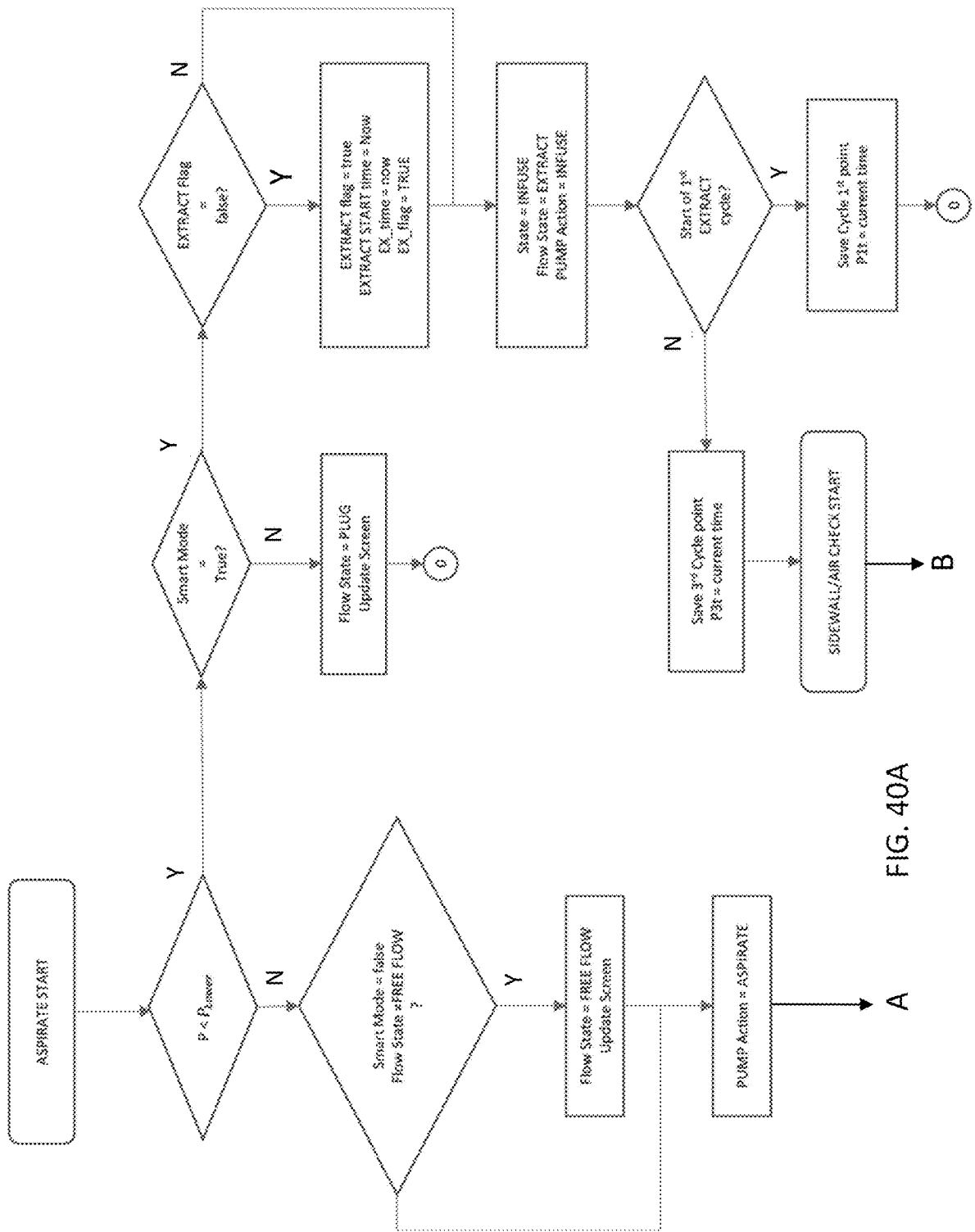
FIGS. 40A and 40B are a flowchart illustrating a method of removing a thrombus from a body lumen.
Figure 40B:
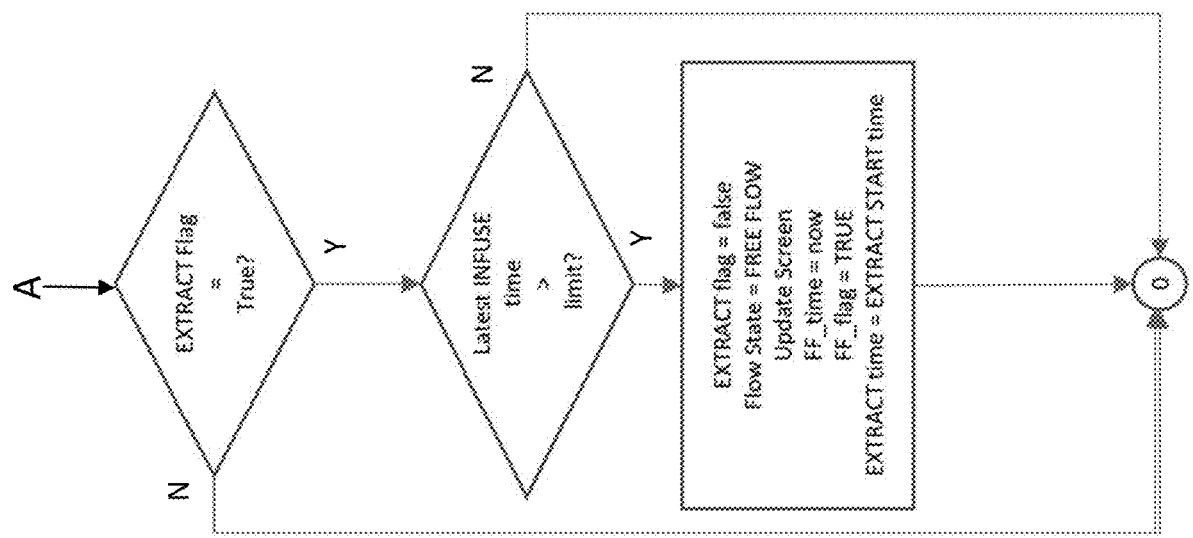

Turning now to FIGS. 40A and 40B, the depicted process begins with a start of ASPIRATE. The pump generates negative pressure creating a suction effect. If the pump is operating with the Smart Mode Off (Static mode) the aspiration will continue at a constant rate independent of the pressure sensor. If the Smart Mode is On and the APA algorithm will determine how much to aspirate based on the pressure sensor value.

Figure 40C:
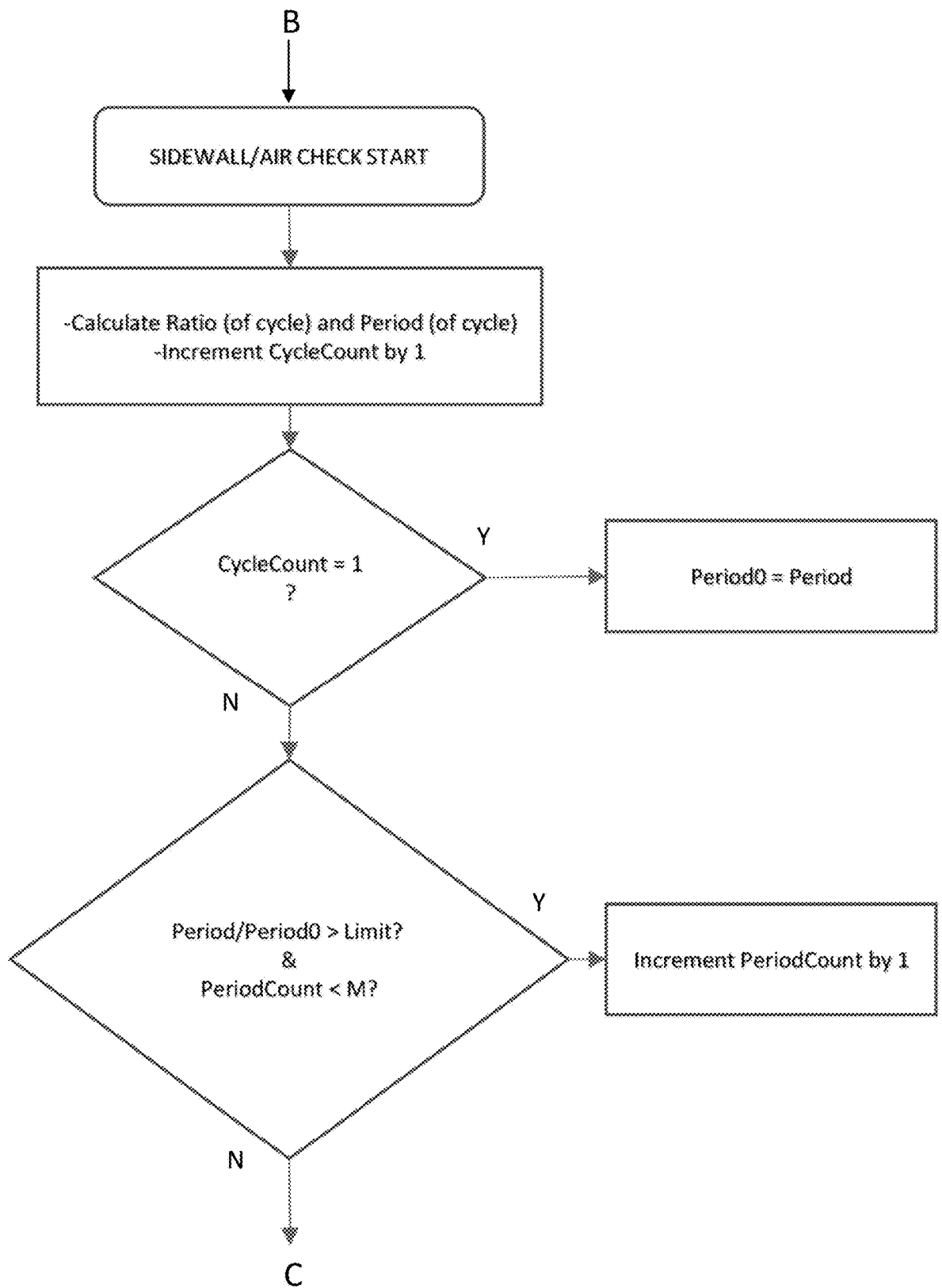
FIGS. 40C and 40D are a flowchart illustrating a method of identifying a sidewall and/or air condition during a method of removing a thrombus from a body lumen.
Figure 40D:
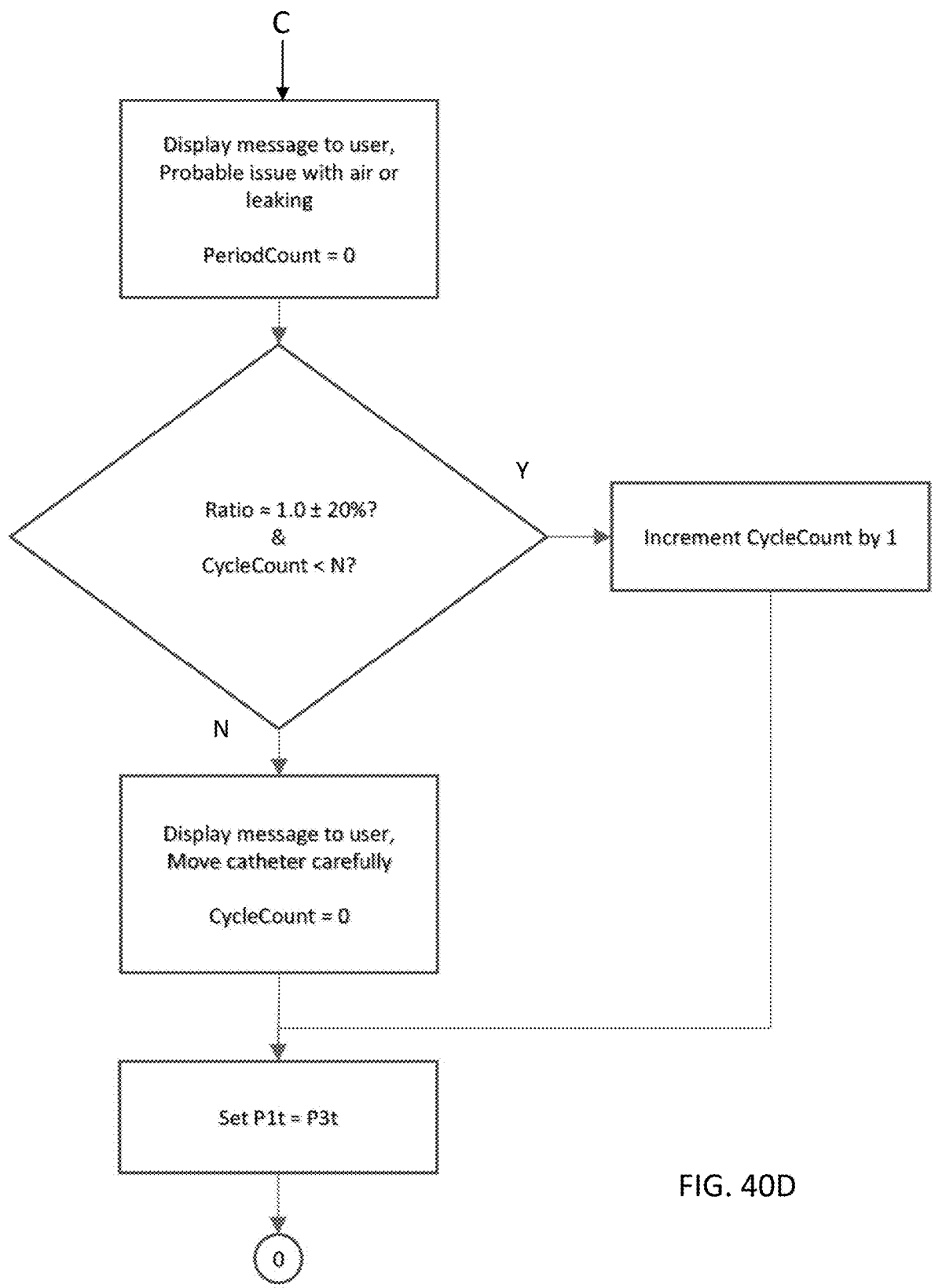

FIGS. 40C and 40D illustrate a method of identifying a side wall and/or airflow condition during a procedure to remove a thrombus of a body lumen. As shown in FIG. 40A, such a sidewall/air process begins at arrow B.

Figure 41A:
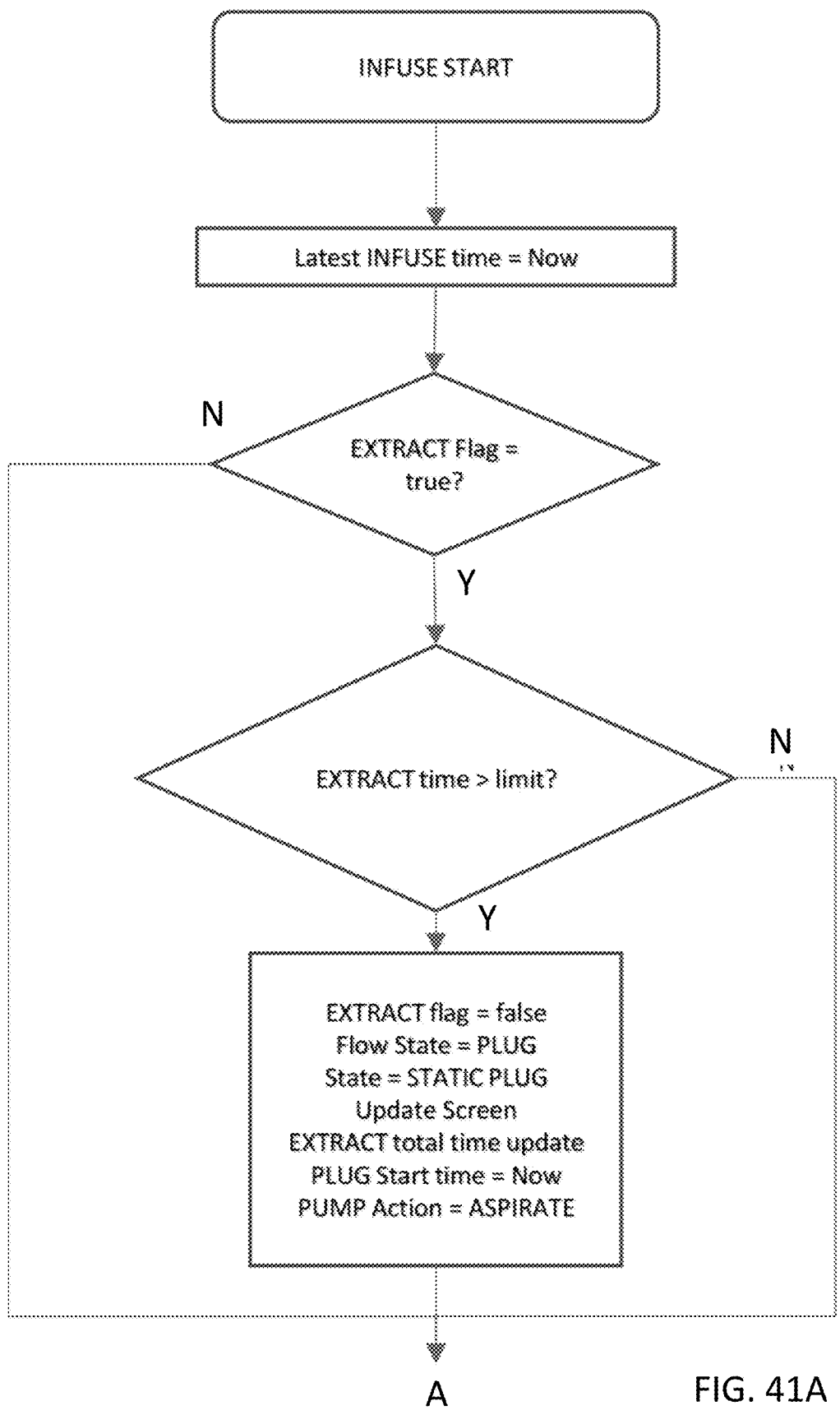
FIGS. 41A-41C are a flowchart illustrating a method of removing a thrombus from a body lumen.
Figure 41B:
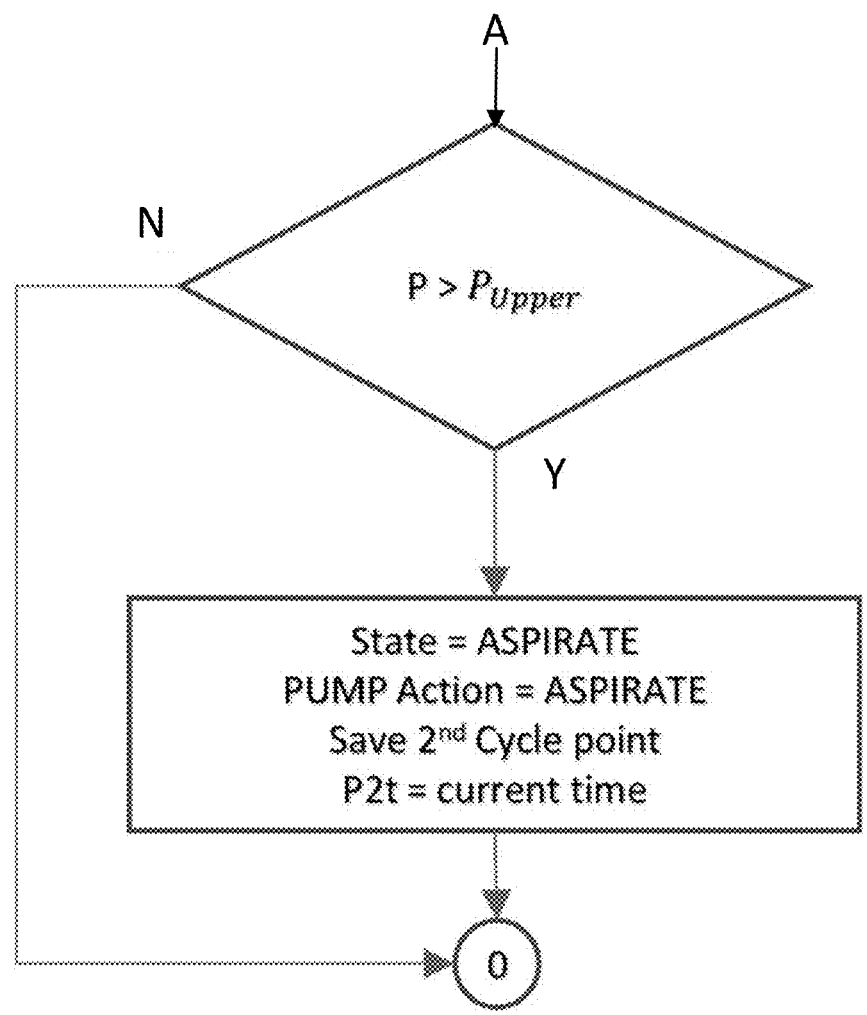
Figure 41C:
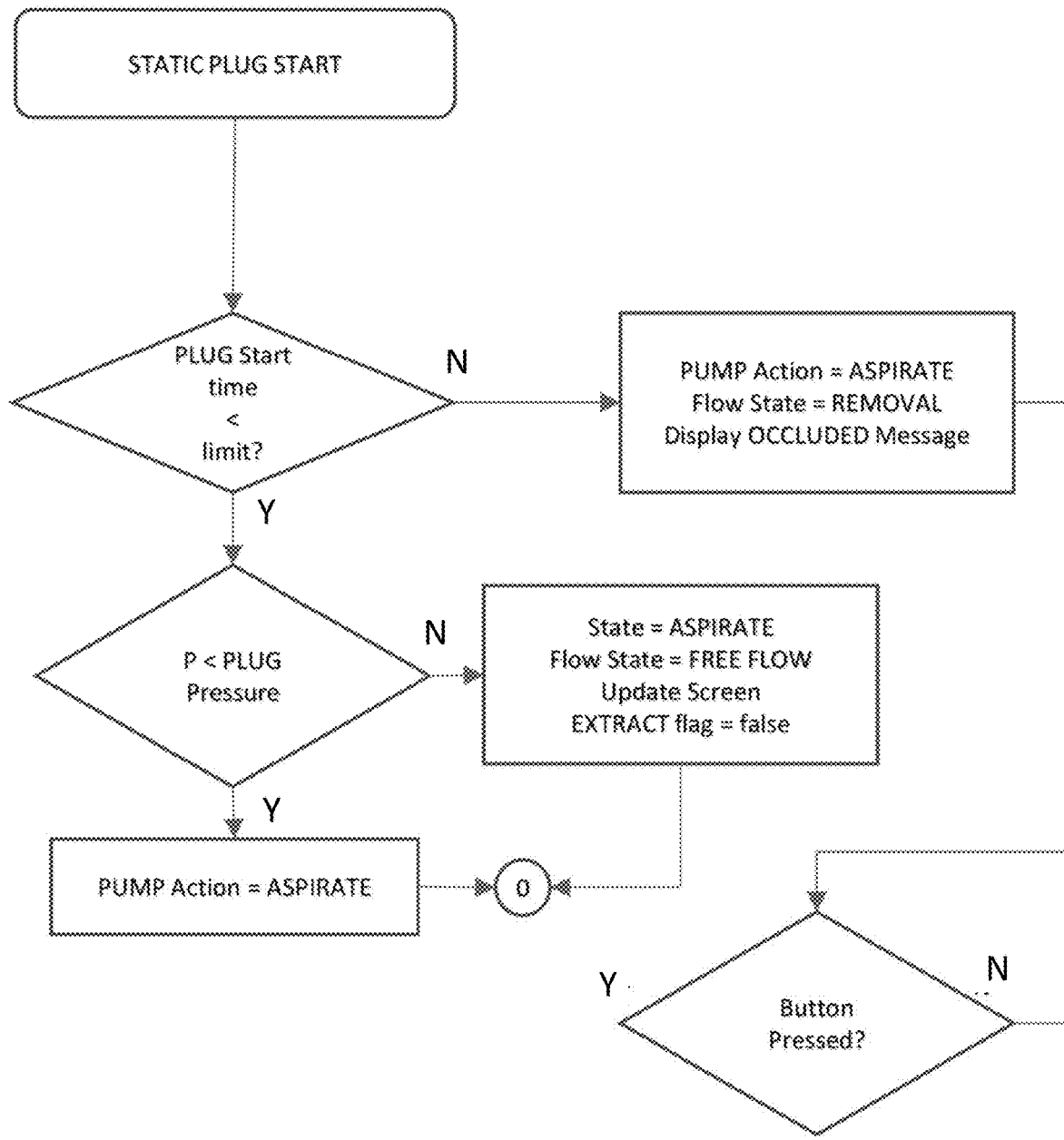

Referring to FIGS. 41A-41C, in INFUSE state, the pump generates a positive pressure on the fluid. This operational state only occurs during the EXTRACT state in Smart mode. The algorithm will determine how much to INFUSE based on the pressure sensor value.

Also in FIGS. 41A-41C, a STATIC PLUG control state is shown. During the STATIC PLUG state, the pump maintains a negative pressure for a specified time. This allows the clot to be affected by the pressure and break to thereby allow partial fluid flow or simply allow the clot to pass through the catheter. When the STATIC PLUG state has been active for less than a specified time, the Flow State is set to PLUG. If no changes occur to the clot, based on the pressure sensor values, then the Flow State switches to REMOVAL. During the PLUG Flow State, a change in the pressure can trigger a return back to the EXTRACT state. Once the Flow State has been set to REMOVAL, the algorithm maintains a static negative pressure until the start/stop button has been pressed.

The selected algorithm uses various pressure level values to control the pump operation. These include blood pressure (BP), upper positive pressure limit allowed by the pump≤BP (Pupper), lower negative pressure limit to trigger clot removal, and Atmospheric pressure (ATM).

The pump controller according to an embodiment of the invention keeps track of the total amount of time the unit has been ON and the time the current EXTRACT state has been active. These and other additional values can be stored with the processor for later retrieval.

Figure 42:
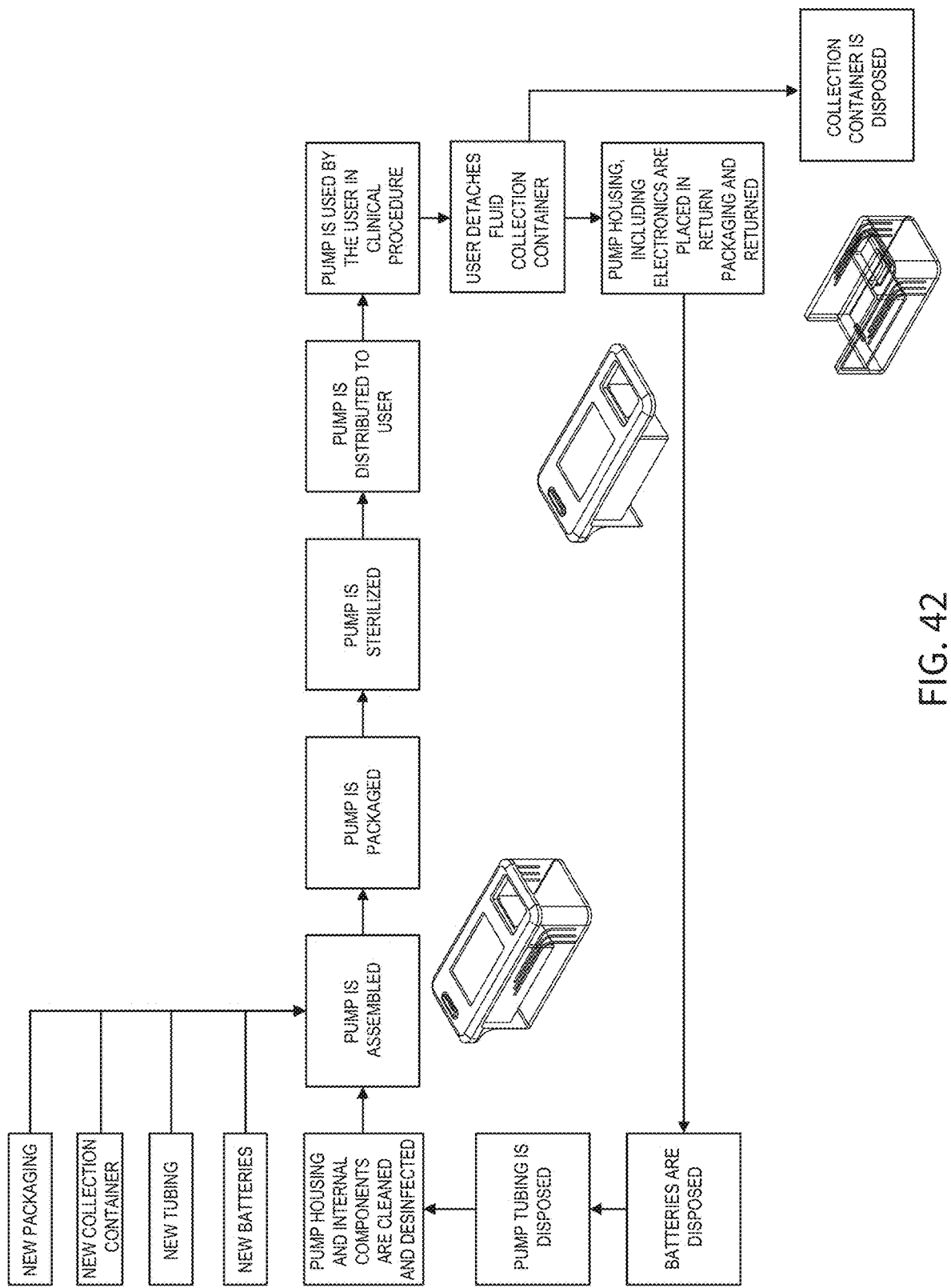
FIG. 42 is a flowchart illustrating a recycling and reprocessing process.

FIG. 42 is an annotated flowchart outlining a recycling and reprocessing model according to an exemplary embodiment of the invention, setting forth an example of recycling methodologies according to one possible example of the invention.

While various embodiments have been described above, it should be understood that the various embodiments have been presented by way of example only and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

While several embodiments of the present disclosure are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method.

Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method.

Additionally, the order in which a particular method occurs may or may not strictly adhere to the order of the corresponding steps or methodologies shown.

It should be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Various preferred embodiments are described herein with references to the drawings in which merely illustrative views are offered for consideration. Corresponding reference characters indicate corresponding components throughout the several views of the drawings. Skilled artisans will appreciate that elements in the figures are illustrated for simplicity and clarity, and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

Although various embodiments have been described as having particular features and/or combinations of components, other embodiments are possible having a combination of any features and/or components from any of embodiments as discussed above.

Further, aspects have been described in the general context of removal of a thrombus of a blood vessel, but inventive aspects are not necessarily limited to use in blood vessels. For example, the embodiments described herein may be used to remove an obstruction from other parts of a body such as within a brain.

What is claimed is:

1. An apparatus, comprising:
    a housing including a first housing portion defining a pump cavity and a second housing portion defining a waste volume, the first housing portion being integrally connected to the second housing portion, the pump cavity configured to receive a thrombectomy pump;
    a clot retainer removably coupled to the housing within the waste volume, the clot retainer having a surface, a portion of the surface of the clot retainer defining a plurality of openings sized to allow liquid to flow through the surface and into the waste volume; and
    a lid removably coupled to the housing to cover the clot retainer, the lid including a transparent portion to allow viewing of the clot retainer through the lid.

2. The apparatus of claim 1, wherein:
    the housing has a base surface; and
    the portion of the surface of the clot retainer is a first portion disposed at a first distance from the base surface of the housing, the clot retainer including a second portion of the surface of the clot retainer disposed at a second distance from the base surface of the housing, the second distance being greater than the first distance, the second portion of the surface of the clot retainer defining a bypass opening.

3. The apparatus of claim 2, wherein the housing defines an outlet port in a side wall of the housing between the pump cavity and the waste volume at a third distance from the base surface, the third distance being greater than the first distance, the outlet port being in fluid communication with the waste volume.

4. The apparatus of claim 3, further comprising:
    an aspiration tube extending from the thrombectomy pump within the pump cavity, a portion of aspiration tube extending within the outlet port and in fluid communication with the waste volume.

5. The apparatus of claim 4, further comprising:
    the thrombectomy pump disposed within the pump cavity, the thrombectomy pump coupled to the aspiration tube to provide fluid communication between the thrombectomy pump and the waste volume.

6. The apparatus of claim 5, wherein the thrombectomy pump is a positive displacement pump.

7. The apparatus of claim 1, wherein:
    the clot retainer includes a tab extending upwardly from the surface,
    the tab includes an alignment feature configured to matingly engage the lid.

8. The apparatus of claim 1, wherein:
the waste volume encircles at least a portion of the pump cavity.

9. The apparatus of claim 1, further comprising:
at least one light coupled to the housing and configured to illuminate the waste volume.

10. The apparatus of claim 1, wherein:
the portion of the surface of the clot retainer is a first portion, the clot retainer includes a second portion of the surface of the clot retainer that defines a bypass opening.

11. The apparatus of claim 10, wherein:
the housing includes a mounting shoulder within the waste volume, the clot retainer supported on the mounting shoulder,
the housing has a base surface, and
the mounting shoulder positions the clot retainer such that at least the second portion of the surface of the clot retainer is at an angle relative to the base surface of the housing.

12. An apparatus, comprising:
a housing including a first housing portion defining a pump cavity and a second housing portion defining a waste volume, the waste volume at least partially encircles the first housing portion;
a pump assembly disposed within the pump cavity, the pump assembly including an inlet port configured to be coupled to a catheter and an output port in fluid communication with the waste volume;
the pump assembly including a pump, a motor to drive the pump, and a controller;
a cover coupled to the first housing portion and enclosing the pump cavity; and
a display screen coupled to the cover and operably coupled to the controller.

13. The apparatus of claim 12, further comprising:
a lid removably coupled to the second housing portion and enclosing at least a portion of the waste volume.

14. The apparatus of claim 12, further comprising:
a switch coupled to the pump assembly;
the switch configured to send an indication to the controller when the pump assembly has been decoupled from the housing; and
the controller configured to automatically shut off the pump assembly based on receipt of the indication by the controller.

15. The apparatus of claim 12, further comprising:
a clot retainer removably coupled to the housing within the waste volume, the clot retainer having a bottom surface, a first portion of the bottom surface of the clot retainer defining a plurality of openings sized to allow liquid to flow through the bottom surface and into the waste volume, a second portion of the bottom surface of the clot retainer defining a bypass opening.

16. The apparatus of claim 15, further comprising:
a lid removably coupled to the second housing portion and enclosing at least a portion of the waste volume,
the housing has a base surface, the waste volume has a height defined between the lid and the base surface, and
the bottom surface of the clot retainer being positioned relative to the lid at a distance equal to between 5% and 25% of the height of the waste volume.

17. The apparatus of claim 15, wherein:
the housing has a base surface, an outlet port being positioned at a first distance relative to the base surface, the bottom surface of the clot retainer being disposed at a second distance from the base surface, the first distance being greater than the second distance.

18. The apparatus of claim 15, further comprising:
a lid removably coupled to the second housing portion and enclosing at least a portion of the waste volume,
the clot retainer includes a tab extending upwardly from the bottom surface, and
the tab includes an alignment feature configured to matingly engage the lid.

19. The apparatus of claim 12, further comprising:
at least one light coupled to at least one of the pump assembly or the housing and configured to illuminate the waste volume.

20. The apparatus of claim 12, wherein the cover has a top surface defining a first surface area, the display screen defines a second surface area, the second surface area being greater than 70 percent of the first surface area.

21. The apparatus of claim 12, wherein:
the pump assembly includes a switch configured to automatically shut off the pump when the second housing portion is removed from the first housing portion.

22. An apparatus, comprising:
a housing including a first housing portion defining a pump cavity and a second housing portion defining a waste volume; and
a pump assembly disposed within the pump cavity, the pump assembly including an inlet port configured to be coupled to a catheter and an output port in fluid communication with the waste volume,
the pump assembly including a pump, a motor to drive the pump, a switch, and a controller,
the switch of the pump assembly configured to engage a protrusion of the housing when the pump assembly is disposed within the pump cavity,
the switch of the pump assembly configured to send an indication to the controller when the pump assembly has been removed from the housing and the switch is disengaged from the protrusion, and
the controller configured to automatically shut off the pump assembly based on receipt of the indication.

23. The apparatus of claim 22, wherein:
the controller is configured to automatically shut off the pump assembly after a preselected time has passed after the switch has disengaged from the protrusion.

24. The apparatus of claim 22, further comprising:
a cover coupled to the first housing portion and enclosing the pump cavity; and
a display screen coupled to the cover and operably coupled to the controller.

25. The apparatus of claim 24, wherein:
in response to receipt of the indication, the controller is configured to send a notification to the display screen to provide an output indicating that the pump assembly has been removed from the housing.

26. An apparatus, comprising:
a housing including a pump cavity and a waste volume, the pump cavity configured to receive a thrombectomy pump;
a clot retainer removably coupled to the housing within the waste volume, the clot retainer having a surface, at least a portion of the surface of the clot retainer defining a plurality of openings sized to allow liquid to flow through the surface and into the waste volume; and
a lid removably coupled to the housing to cover the clot retainer, wherein the housing has a base surface and the at least a portion of the surface of the clot retainer is disposed at a first distance from the base surface of the housing, and the housing defines an outlet port in a side wall of the housing between the pump cavity and the waste volume at a second distance from the base surface, the second distance being greater than the first distance, the outlet port being in fluid communication with the waste volume.

27. The apparatus of claim 26, wherein:

the lid includes a transparent portion to allow viewing of the clot retainer through the lid.

\* \* \* \* \*